United States Patent
Kufe

(10) Patent No.: US 7,745,109 B2
(45) Date of Patent: *Jun. 29, 2010

(54) REGULATION OF CELL GROWTH BY MUC1

(75) Inventor: Donald W. Kufe, Wellesley, MA (US)

(73) Assignee: Dana-Farber Cancer Insitute, Inc., Boston, MA (US)

( * ) Notice: Subject to any disclaimer, the term of this patent is extended or adjusted under 35 U.S.C. 154(b) by 555 days.

This patent is subject to a terminal disclaimer.

(21) Appl. No.: 10/733,212

(22) Filed: Dec. 11, 2003

(65) Prior Publication Data

US 2004/0166543 A1 Aug. 26, 2004

(51) Int. Cl.
C12Q 1/00 (2006.01)
C07K 2/00 (2006.01)
G01N 33/48 (2006.01)

(52) U.S. Cl. ............... 435/4; 435/7.2; 435/7.72; 435/7.8; 435/29

(58) Field of Classification Search ............... 435/4, 435/7.2, 7.72, 7.8, 29
See application file for complete search history.

(56) References Cited

U.S. PATENT DOCUMENTS

| 4,497,796 A | 2/1985 | Salser et al. ............ 514/44 |
| 4,675,382 A | 6/1987 | Murphy ............ 260/112 |
| 4,894,227 A | 1/1990 | Stevens et al. ........ 424/85.2 |
| 4,963,484 A | 10/1990 | Kufe ............ 435/69.3 |
| 5,053,489 A | 10/1991 | Kufe ............ 530/350 |
| 5,080,898 A | 1/1992 | Murphy ............ 424/94.1 |
| 5,380,712 A | 1/1995 | Ballance et al. ........ 514/12 |
| 5,506,343 A | 4/1996 | Kufe ............ 530/387.7 |
| 5,530,101 A | 6/1996 | Queen et al. ......... 530/387.3 |
| 5,565,334 A | 10/1996 | Kufe et al. .......... 435/69.1 |
| 5,612,895 A | 3/1997 | Balaji et al. .......... 702/19 |
| 5,766,833 A | 6/1998 | Suematsu et al. ...... 435/69.7 |
| 5,776,427 A | 7/1998 | Thorpe et al. ........ 424/1.49 |
| 5,801,154 A | 9/1998 | Baracchini et al. ...... 514/44 |
| 5,851,775 A * | 12/1998 | Barker et al. ........... 435/6 |
| 5,861,381 A | 1/1999 | Chambon et al. ........ 514/44 |
| 5,965,386 A | 10/1999 | Kerry-Williams et al. .. 435/69.1 |
| 5,998,148 A | 12/1999 | Bennett et al. .......... 435/6 |
| 6,004,746 A * | 12/1999 | Brent et al. ............ 435/6 |
| 6,020,363 A | 2/2000 | Hirano et al. ........... 514/456 |
| 6,054,438 A | 4/2000 | Taylor-Papadimitriou et al. ......... 514/44 |
| 6,074,841 A | 6/2000 | Gearing et al. .......... 435/69.1 |
| 6,222,020 B1 | 4/2001 | Taylor-Papadimitriou et al. ......... 530/395 |
| 6,589,921 B2 | 7/2003 | Herrmann et al. ........ 514/456 |
| 6,716,627 B2 | 4/2004 | Dobie ............ 435/375 |
| 2002/0110841 A1 | 8/2002 | Kufe ............ 435/7.23 |
| 2003/0148969 A1 | 8/2003 | Dobie et al. ........... 514/44 |
| 2004/0018181 A1 | 1/2004 | Kufe et al. ........... 424/93.21 |
| 2004/0166543 A1 | 8/2004 | Kufe ............ 435/7.23 |
| 2004/0209832 A1 | 10/2004 | McSwiggen .......... 514/44 |
| 2005/0053606 A1 | 3/2005 | Kufe et al. ............ 424/155.1 |

FOREIGN PATENT DOCUMENTS

| DE | 19909251 | 8/1999 |
| EP | 1103623 | 7/1998 |
| WO | WO 93/20841 | 10/1993 |
| WO | WO 96/03502 A2 | 2/1996 |
| WO | WO 99/23114 | 5/1999 |
| WO | WO 91/09867 | 7/1999 |
| WO | WO 00/25827 | 5/2000 |
| WO | WO 00/34468 | 6/2000 |
| WO | WO 00/77031 | 12/2000 |
| WO | WO 01/12217 | 2/2001 |
| WO | WO 01/18035 | 3/2001 |
| WO | WO 01/57068 | 8/2001 |
| WO | WO 02/22685 A2 | 3/2002 |
| WO | WO 02/31512 | 4/2002 |
| WO | WO 02/058450 | 8/2002 |
| WO | WO 03/014303 | 2/2003 |
| WO | WO 03/088995 | 10/2003 |
| WO | WO 2004/044160 | 5/2004 |
| WO | WO 2004/092339 | 10/2004 |

OTHER PUBLICATIONS

Yamamoto et al, J. Biol. Chem. 272(19): 12492-12494, 1997.*
Li et al, Mol. Cell Biol. 18(12): 7216-7224, 1998.* of record in IDS.*
Zrihan-Licht et al, FEBS Letters 356(1):130-136, 1994.*
Hanks et al, FASEB J. 9:576-596, 1995.*
Batra et al., "Transfection of the Human MUC-1 Mucin Gene into a Poorly Differentiated Human Pancreatic Tumor-Cell Line, Panc1: Integration, Expression, and Ultrastructural-Changes", J. Cell Sci., (1991) 100(4):841-849 (Abstract).
Burton et al., "Epithelial Mucin-1 (MUC1) Expression and MA5 Anti-MUC1 Monoclonal Antibody Targeting in Multiple Myeloma", Clin. Can. Res. (1999) 5 (10S):3065s-3072s (Abstract).
Hartman et al., "MUC1 Isoform Specific Monoclonal Antibody 6E6/2 Detects Preferential Expression of the Novel MUC1/Y Protein in Breast and Ovarian Cancer", Int. J. Can. (1999) 82:256-267.
Kam et al., "MUC1 Synthetic Peptide Inhibition of Intracellular Adhesion Molecule-1 and MUC1 Binding Requires Six Tandem Repeats", Can. Res. (1998) 58 (23):5577-5581 (Abstract).
Kondo et al., "Decreased MUC1 Expression Induces E-Cadherin-Mediated Cell-Adhesion of Breast Cancer Cell Lines", Can. Res. (1998) 58 (9):2014-2019 (Abstract).
Li et al., "Interaction of Glycogen synthase kinase 3 Beta with the DF3/MUC1 Carcinoma-Associated Antigen and Beta-Catenin", Mol. Cell Biol., (1998) 18 (12):7216-7224.

(Continued)

Primary Examiner—Kevin K. Hill
(74) Attorney, Agent, or Firm—Fulbright & Jaworski LLP

(57) ABSTRACT

The invention features a method of identifying a compound that inhibits (a) the physical interaction (binding) between MUC1 and tumor progressors (e.g., β-catenin, c-Src, EGF-R, p120$^{ctn}$, or PKCδ) and/or (b) phosphorylation of MUC1 by tumor progressors with kinase activity (e.g., c-Src, EGF-R, or PKCδ). The invention also includes a method of inhibiting an interaction between MUC1 and β-catenin and a method of inhibiting expression of MUC1 or a tumor progressor in a cell.

23 Claims, 24 Drawing Sheets

OTHER PUBLICATIONS

U.S. Appl. No. 60/308,307, filed Jul. 27, 2001, Kufe.
U.S. Appl. No. 60/502,111, filed Sep. 11, 2003, Jecminek et al.
European Search Report, issued in European Application No. 08005820.9, dated Jul. 22, 2008.
"MUC-1/X mucin short variant," GenBank Accession No. AAD10856, dated Jun. 5, 2001.
"MUC-1/Z mucin short variant," GenBank Accession No. AAD10858, dated Jun. 5, 2001.
"Mucin 1 precursor, non-repetitive splice from Y [validated]—human," GenBank Accession No. S48146, dated Apr. 20, 2000.
Abe et al., "Characterization of cis-acting elements regulating transcription of the human DF3 breat carcinoma-associated antigen (MUC1) gene," *Proc. Natl. Acad. Sci. USA.*, 90:282-286, 1993.
Abe et al., "Identification of a family of high molecular weight tumor-associated glycoproteins," *J. Immun.*, 139:257-261, 1987.
Abe et al., "Sequence Anaylsis of the 5' region of the human DF3 breast carcinoma-associated antigen gene," *Bio. Biophys. Research Comm.*, 165:664-649, 1989.
Abe et al., "Sodium butyrate induction of milk-related antigens in human MCF-7 breast carcinoma cells," *Cancer Res.*, 44:4574-4577, 1984.
Abe et al., "Structural analysis of the DF3 human breat carcinoma-associated protein," *Cancer Res.*, 49:2834-2839, 1989.
Abe et al., "Transcriptional regulation of DF3 gene expression in human MCF-7 breast carcinoma cells," *J. Cell. Physio.*, 143:226-231, 1990.
Adams and Cory, "The Bcl-2 Protein Family: Arbiters of Cell Survival," *Science*, 281:1322-1326, 1998.
Agrawal and Kandimalla, "Antisense therapeutics: is it as simple as complementary base recognition?" *Molecular Medicine Today*, 6:72-81, 2000.
Akagi et al., "CA19-9 epitope a possible marker for MUC-1/Y protein," *Int. J. Oncol.*, 18:1085-1091, 2001.
Apostolopoulos et al., "Production of anti-breast cancer monoclonal antibodies using a glutathione-S-transferase-MUC1 bacterial fusion protein," *British J. Cancer.*, 67:713-720, 1993.
Arklie et al., "Differentiation antigens expressed by epithelial cells in the lactating breast are also detectable in breast cancers," *Int. J. Cancer*, 28:23-29, 1981.
Ashkenazi and Dixit, "Apoptosis control by death and decoy receptors," *Curr. Opin. Cell Biol.*, 11:255-260, 1999.
Ashkenazi and Dixit, "Death Receptors: Signaling and Modulation," *Science*, 281:1305-1308, 1998.
Ashkenazi et al., "Safety and antitumor activity of recombinant soluble Apo2 ligand," *J. Clin. Invest.*, 104:155-162, 1999.
Backstom et al., "Recombinant MUC1 mucin with a breast cancer-like O-glycosylation produced in large amounts in Chinese-hamster ovary cells," *Biochemical Journal*, 376:677-686, 2003.
Banerjee, "Omega amino acids in peptide design: incorporation into helices," *Biopolymers*, 39:769-77, 1996.
Barrett et al., "PLU-1 nuclear protein, which is upregulated in breast cancer, shows restricted expression in normal human adult tissues: a new cancer/testis antigen?," *Int. J. Cancer*, 101:581-588, 2002.
Barry and Sharkey, "Observer reproducibility during computer-assisted planimetric measurements of nuclear features," *Hum. Pathol.*, 16:225-7, 1985.
Barry et al., "Activation of programmed cell death (apoptosis) by cisplatin, other anticancer drugs, toxins and hyperthermia," *Biochemical Pharmacology*, 40:2353-2362, 1990.
Baruch et al., "Preferential expression of novel MUC1 tumor antigen isoforms in human epithelial tumors and their tumor-potentiating function," *Int. J. Cancer*, 71:741-749, 1997.
Baruch et al., "The breast cancer-associated MUC1 gene generates both a receptor and its cognate binding protein," *Cancer Res.*, 59:1552-1561, 1999.
Bass, "The short answer," *Nature*, 411:428-429, 2001.
Bellgrau et al., "A role for CD95 ligand in preventing graft rejection," *Nature*, 377:630-632, 1995.
Berger et al., "Respiratory carcinoma cell lines: MUC genes and glycoconjugates," *American Journal of Respiratory Cell and Molecular Biology*, 20:500-510, 1999.
Bergeron et al., "MAUB is a new mucin antigen associated with bladder cancer," *J. Biol. Chem.*, 271:6933-6940, 1996.
Beusen et al., "Conformational mimicry: synthesis and solution conformation of a cyclic somatostatin hexapeptide containing a tetrazole cis amide bond surrogate," *Biopolymers*, 36:181-200, 1995.
Bird et al., "Single-chain antigen-binding proteins," *Science*, 242:423-6, 1988.
Bodmer et al., "Cysteine 230 is essential for the structure and activity of the cytotoxic ligand TRAIL," *J. Biol. Chem.*, 275:20632-20637, 2000.
Boldin et al., "Involvement of MACH, a novel MORT1/FADD-interacting protease, in Fas/APO-1- and TNF receptor-induced cell death," *Cell*, 85:803-815, 1996.
Brossart et al., "Identification of HLA-A2-restricted T-cell epitopes derived from MUC1 tumor antigen for broadly applicable vaccine therapies," *Blood*, 93:4309-4317, 1999.
Brunner et al.,"*pangolin*encodes a Lef-1 homologue that acts downstream of Armadillo to transduce the Wingless signal in *Drosophila*," *Nature*, 385:829-33, 1997.
Bunz, "Cell death and cancer therapy," *Curr. Opin. Pharmacol.*, 1:337-341, 2001.
Burchell et al., "A short sequence, within the amino acid tandem repeat of a cancer-associated mucin, contains immunodominant epitopes," *Int J. Cancer*, 44:691-696, 1989.
Burchell et al., "Development and characterization of breast cancer reactive monoclonal antibodies directed to the core protein of the human milk mucin," *Cancer Res.*, 47:5476-5482, 1987.
Burns and El-Deiry, "Identification of inhibitors of TRAIL-induced death (ITIDs) in the TRAIL-sensitive colon carcinoma cell line SW480 using a genetic approach," *J. Biol. Chem.*, 276:37879-37886, 2001.
Busfield et al., "Characterization of a neuregulin-related gene, *Don-*1, that is highly expressed in restricted regions of the cerebellum and hippocampus," *Mol. Cell. Biol.*, 17:4007-4014, 1997.
Cawley et al., "Epidermal growth factor-toxin A chain conjugates: EGF-Ricin A is a potent toxin while EGF-Diphtheria fragment A is nontoxic," *Cell*, 22:563-570, 1980.
Chang et al., "Artificial hybrid protein containing a toxic protein fragment and a cell membrane receptor-binding moiety in a disulfide conjugate," *J. Biol. Chem.*, 252:1515-1522, 1977.
Chang et al., "Ligands for ErbB-family receptors encoded by a neuregulin-like gene," *Nature*, 387:509-512, 1997.
Chaudhary et al., "A rapid method of cloning functional variable-region antibody genes in *Escherichia coli* as single-chain immunotoxins," *Proc. Natl. Acad. Sci. U.S.A.*, 87:1066-70, 1990.
Chaudhary et al., "Activity of a recombinant fusion protein between transforming growth factor type alpha and Pseudomonas toxin," *Proc. Natl. Acad. Sci. USA*, 84:4538-4542, 1987.
Ciborowski et al., "Screening of anti-MUC1 antibodies for reactivity with native (ascites) and recombinant (baculovirus) MUC1 and for blocking MUC1 specific cytotoxic T-lymphocytes," *Tumor Biology*, 19:147-151, 1998.
Console et al., "Antennapedia and HIV transactivator of transcription (TAT) "protein transduction domains" promote endocytosis of high molecular weight cargo upon binding to cell surface glycosaminoglycans," *J. Biol. Chem.*, 278 :35109-14, 2003.
Creagan et al., "Phase III clinical trial of the combination of cisplatin, dacarbazine, and carmustine with or without tamoxifen in patients with advanced malignant melanoma," *J. Clin. Oncol.*, 17:1884-1890, 1999.
Croghan et al., "Tissue distribution of an epithelial and tumor-associated antigen recognized by monoclonal antibody F36/22," *Cancer Res.*, 43:4980-4988, 1983.
Cunningham et al., "Calreticulin binding and other biological activities of survival peptide Y-P30 including effects of systemic treatment of rats," *Exp. Neurol.*, 163:457-468, 2000.
Cunningham et al., "Identification of a survival-promoting peptide in medium conditioned by oxidatively stressed cell lines of nervous system origin," *J. Neurosci.*, 18:7047-7060, 1998.

Cunningham et al., "Identification of the human cDNA for new survival/evasion peptide (DSEP): studies in vitro and in vivo of overexpression by neural cells," *Exp. Neurol.*, 177:32-39, 2002.

Daniel and Reynolds, "The catenin p120(ctn) interacts with Kaiso, a novel BTB/POZ domain zinc finger transcription factor," *Mol. Cell. Biol.*, 19:3614-23, 1999.

Datta et al., "Overexpression of Bcl-XL by cytotoxic drug exposure confers resistance to ionizing radiation-induced internucleosomal DNA fragmentation," *Cell Growth Differ*, 6:363-370, 1995.

Dawson et al., "Synthesis of proteins by native chemical ligation," *Science*, 266:776-779, 1994.

Deng et al., "TRAIL-induced apoptosis requires Bax-dependent mitochondrial release of Smac/DIABLO," *Genes Dev.*, 16:33-45, 2002.

Derossi et al., "Cell internalization of the third helix of the Antennapedia homeodomain is receptor-independent," *J Biol. Chem.*, 271:18188-93, 1996.

Derossi et al., "The third helix of the Antennapedia homeodomain translocates through biological membranes," *J Biol. Chem.*, 269:10444-50, 1994.

Deveraux and Reed, "IAP family proteins—suppressors of apoptosis," *Genes Dev.*, 13:239-52, 1999.

Dillman, "Antibodies as cytotoxic therapy," *J. Clin. Oncology*, 12:1497-1515, 1994.

Doyle, "Crystal structures of a complexed and peptide-free membrane protein-binding domain: molecular basis of peptide recognition by PDZ," *Cell*, 85:1067-76, 1996.

Drucker et al., "Tamoxifen enhances apoptotic effect of cisplatin on primary endometrial cell cultures," *Anticancer Research*, 23:1549-1554, 2003.

Du et al., "Smac, a Mitochondrial Protein that Promotes Cytochrome c-Dependent Caspase Activation by Eliminating IAP Inhibition," *Cell*, 102:33-42, 2000.

Elbashir et al., "Analysis of gene function in somatic mammalian cells using small interfering RNAs," *Methods*, 26:199-213, 2002.

Elbashir et al., "Functional anatomy of siRNAs for mediating efficient RNAi in *Drosophila melanogaster* embryo lysate," *EMBO Journal*, 20:6877-6888, 2001.

Elbashir et al., "RNA interference is mediated by 21-and 22-nucleotide RNAs," *Genes & Development*, 15:188-200, 2001.

Elliot and O'Hare, "Intercellular trafficking and protein delivery by a herpesvirus structural protein," *Cell*, 88:223-33, 1997.

Elmquist et al., "VE-cadherin-derived cell-penetrating peptide, pVEC, with carrier functions," *Exp. Cell Res.*, 269:237-44, 2001.

Emoto et al., "Proteolytic activation of protein kinase C delta by an ICE-like protease in apoptotic cells," *EMBO J.*, 14:6148-6156, 1995.

Faivre et al., "Supraadditive effect of 2',2'difluorodeoxycytidine (gemcitabine) in combination with oxaliplatin in human cancer cell lines," *Cancer Chemother. Pharmacol.*, 44:117-123, 1999.

Feigl, "2,8-Dimethyl-4-(carboxymethyl)-6-(aminomethyl)phenoxathiin S-Dioxide: An Organic Substitute for the beta-Turn in Peptides," *J. Amer. Chem. Soc.*, 108:181-2, 1986.

Finn et al., "MUC-1 Epithelial Tumor Mucin-Based Immunity and Cancer Vaccines," *Immunol. Rev.*, 145:61-89, 1995.

Fontenot et al., "Biophysical characterization of one-, two-, and three-tandem repeats of human musin (muc-1) protein core," *Cancer Research*, 53:5386-5394, 1993.

Frankel and Pabo, "Cellular uptake of the tat protein from human immunodeficiency virus," *Cell*, 55:1189-93, 1989.

French and Tschopp, "Inhibition of Death Receptor Signaling by FLICE-inhibitory Protein as a Mechanism for Immune Escape of Tumors," *J. Exp. Med.*, 190:891-893, 1999.

Futaki et al., "Arginine-rich peptides. An abundant source of membrane-permeable peptides having potential as carriers for intracellular protein delivery," *J. Biol. Chem.*, 276 :5836-40, 2001.

Gendler et al., "A highly immunogenic region of a human polymorphic epithelial mucin expressed by carcinomas is made up of tandem repeats," *J. Biol. Chem.*, 263:12820-12823, 1988.

Gendler et al., "Molecular cloning and expression of human tumor-associated polymorphic epithelial mucin," *J. Biol. Chem.*, 265:15286-15293, 1990.

George, D.G. et al., "Chapter 12. Current Methods in Sequence Comparison and Analysis," in: Macromolecular Sequencing and Synthesis. Selected Methods and Applications, Alan R. Liss, Inc., pp. 127-149 (1988).

Gopalakrishnan et al., "Application of Micro Arrayed Compound Screening (microARCS) to identify inhibitors of caspase-3," *J. Biomol. Screen*, 7:317-23, 2002.

Green and Loewenstein, "Autonomous functional domains of chemically synthesized human immunodeficiency virus tat trans-activator protein," *Cell*, 55:1179-88, 1989.

Griffith et al., "CD95-Induced Apoptosis of Lymphocytes in an Immune Privileged Site Induces Immunological Tolerance," *Immunity*, 5:7-16, 1996.

Gross et al., "Caspase cleaved BID targets mitochondria and is required for cytochrome c release, while BCL-XL prevents this release but not tumor necrosis factor-Rl/Fas death," *J. Biol. Chem.*, 274:1156-1163, 1999.

Gutierrez et al., "Gene therapy for cancer," *The Lancet*, 339:715-721, 1992.

Haim et al., "Dexamethasone, cytarabine, ifosfamide, and cisplatin as salvage therapy in Non-Hodgkin lymphoma," *Am. J. Clin. Oncol.*, 22:47-50, 1999.

Hammond et al., "Post-transcriptional gene silencing by double-stranded RNA," *Nature Genetics*, 2:110-119, 2001.

Hanson et al.,"MUC1 expression in primary breast cancer: the effect of tamoxifen treatment," *Breast Cancer Research and Treatment*, 67:215-222, 2001.

Harborth et al., "Identification of essential genes in cultured mammalian cells using small interfering RNAs," *J. Cell Science*, 114:4557-4565,2001.

Harlow and Lane, "Antibodies, A Lab Manual," Cold Spring Harbor, 1988.

Harris et al., "Therapeutic antibodies—the coming of age," Tibtech, 11:12-44, 1993.

Harrison, "Peptide-surface association: the case of PDZ and PTB domains," *Cell*, 86:341-343, 1996.

Hayes et al., "Comparison of circulating CA15-3 and carcinembryonic antigen levels in patients with breast cancer," *J. Clin. Oncol.*, 4:1542-1550, 1986.

Hayes et al., "Genetically determined polymorphism of the circulating human breast cancer-associated DF3 antigen," *Blood*, 71:436-440, 1998.

Herr and Debatin, "Cellular stress response and apoptosis in cancer therapy," *Blood*, 98:2603-2614, 2001.

Higashiyama et al., "A novel brain-derived member of the epidermal growth factor family that interacts with ErbB3 and ErbB4," *J. Biochem.*, 122:675-680, 1997.

Higgins, "Comparison of the solution conformations of a human immunodeficiency virus peptidomimetic and its retro-inverso isomer using 1H NMR spectroscopy," *J. Pept. Res.*, 50:421-35, 1997.

Hilkens et al., "Biosynthesis of MAM-6, an epithelial sialomucin," *J. Biol. Chem.*, 263:4215-4222, 1988.

Hilkens et al., "Complexity of MAM-6, an epithelial sialomucin associated with carcinomas," *Cancer Res.*, 49:786-793, 1989.

Hilkens et al., "Monoclonal antibodies against human milk-fat globulte membranes detecting differentiation antigens of the mammary gland and its tumors," *Int. J. Cancer*, 34:197-206, 1984.

Hird et al., "Adjuvant therapy of ovarian cancer with radioactive monoclonal antibody," *Br. J. Cancer*, 68:403-406, 1993.

Hopp, "Protein surface analysis. Methods for identifying antigenic determinants and other interaction sites," *J. Immunol. Methods*, 88:1-18, 1986.

Houghton et al., "Monoclonal antibodies: potential applications to the treatment of cancer," *Seminars in Oncology*, 13:165-179, 1986.

Hruby et al., "Design of peptides, proteins, and peptidomimetics in chi space," *Biopolymers*, 43:219-66, 1997.

Hug et al., "Liposomes for the transformation of eukaryotic cells," *Biochem. Biophys. Acta*, 1097:1-17, 1991.

Hull et al., "Oligosaccharide differences in the DF3 sialomucin antigen from normal human milk and the BT-20 human breast carcinomas cell line," *Cancer Commun.*, 1:261-267, 1989.

Hunt and Evans, "Till Death Us Do Part," *Science*, 293:1784-1785, 2001.

Huston et al., "Protein engineering of antibody binding sites: recovery of specific activity in an anti-digoxin single-chain Fv analogue produced in *Escherichia coli*," *Proc. Natl. Acad. Sci U.S.A.*, 85:5879-83, 1988.

Hymowitz et al., "Triggering cell death: the crystal structure of Apo2L/TRAIL in a complex with death receptor 5," *Mol. Cell.*, 4:563-571, 1999.

Irmler et al., "Inhibition of death receptor signals by cellular FLIP," *Nature*, 388:190-195, 1997.

Itzkowitz et al., "Sialosyl-Tn. A novel mucin antigen associated with prognosis in colorectal cancer patients," *Cancer*, 66:1960-6, 1990.

Jaattela et al., "Bcl-x and Bcl-2 inhibit TNF and Fas-induced apoptosis and activation of phospholipase A2 in breast carcinoma cells," *Oncogene*, 10:2297-2305, 1995.

Jawhari et al., "Up-regulated cytoplasmic expression, with reduced membranous distribution, of the src substrate p120(ctn) in gastric carcinoma," *J. Pathol.* 189:180-5, 1999.

Jen et al., "Suppression of gene expression by targeted disruption of messenger RNA: available options and current strategies," *Stem Cells*, 18:307-319, 2000.

Jin et al., "CIAP1 and the serine protease HTRA2 are involved in a novel p53-dependent apoptosis pathway in mammals," *Genes Dev.*, 17:359-67, 2003.

Julian and Carson, "Formation of MUC1 metabolic complex is conserved in tumor-derived and normal epithelial cells," *Biochem. Biophys. Res. Commun.*, 293:1183-1190, 2002.

Kahn et al., "Nonpeptide Mimetics of beta-Turns: A Facile Oxidative Intramolecular Cycloaddition of an Azodicarbonyl System," *J. Amer. Chem. Soc.*, 110:1638-9, 1988.

Kahn, "The design and synthesis of mimetics of peptide beta-turns," *J. Molec. Recognition*, 1:75-9, 1988.

Kalofonos et al., "Kinetics, quantitative analysis and radioimmunolocalisation using indium-111-HMFG1 monoclonal antibody in patients with breast cancer," *Cr. J. Cancer*, 59:939-942, 1989.

Kalofonos et al., "Radioimmunoschintigraphy in patients with ovarian cancer," *Acta Oncologica*, 38:629-634, 1999.

Karlsson et al., "A genetic polymorphism of a human urinary mucin," *Ann. Hum. Genet.*, 47:263, 1983.

Karvinen et al., "Homogeneous time-resolved fluorescence quenching assay (LANCE) for caspase-3," *J. Biomol. Screen.*, 7:223-31, 2002.

Kataoka et al., "FLIP prevents apoptosis induced by death receptors but not by perforin/granzyme B, chemotherapeutic drugs, and gamma irradiation," *J. Immunol.*, 161:3936-3942, 1998.

Kayagaki et al., "Metalloproteinase-mediated release of human Fas ligand," *J. Exp. Med.*, 182:1777-1783, 1995.

Kemp and Stites, "A convenient preparation of derivatives of 3(s)-amino-109(r)-carboxy-1,6-diazacyclodeca-2,7-dione the dilactam of L-alph,gamma-diaminobutyric acid and d-glutamic acid: a beta-turn template," *Tet. Lett.*, 29:5057-60, 1988.

Kennerdell et al., "Heritable gene silencing in *Drosophila* using double-stranded RNA," *Nature Biotechnology*, 17:896-898, 2000.

Kharbanda et al., "Nuclear signaling induced by ionizing radiation involves colocalization of the activated p56/p53lyn tyrosine kinase with p34cdc2," *Cancer Res.*, 56:3617-3621, 1996.

Kischkel et al., "Cytotoxicity-dependent APO-1 (Fas/CD95)-associated proteins form a death-inducing signaling complex (DISC) with the receptor," *EMBO J.*, 14:5579-5588, 1995.

Kluck et al., "The Release of Cytochrome c from Mitochondria: A Primary Site for BCL-2 Regulation of Apoptosis," *Science*, 275:1132-1136, 1997.

Kotera et al., "Humoral immunity against a tandem repeat epitope of human mucin MUC-1 in Ser from breat, pancreatic, and colon cancer patients," *Cancer Research*, 54:2856-2860, 1994.

Kroemer and Reed, "Mitochondrial control of cell death," *Nat. Med.*, 6:513-519, 2000.

Kufe et al., "Differential reactivity of a novel monoclonal antibody (DF3) with human malignant versus benign breast tumors," *Hybridoma*, 3:223-232, 1984.

Kumar et al., "Abrogation of the cell death response to oxidative stress by the c-Abl tyrosine kinase inhibitor STI571," *Mol. Pharmacol.*, 63:276-282, 2003.

Kuppuswamy et al., "Multiple functional domains of Tat, the trans-activator of HIV-1, defined by mutational analysis," *Nucl. Acids Res.*, 17:3551-61, 1989.

Lancaster et al., "Structure and expression of the human polymorphic epithelial mucin cenge: an expressed VNTR unit," *Biochm. Biophys. Res. Comm.*, 173:1019-1029, 1990.

LaVallee et al., "2-Methoxyestradiol up-regulates death receptor 5 and induces apoptosis through activation of the extrinsic pathway," *Cancer Research*, 63:468-475, 2003.

LeBlanc et al., "Tumor-cell resistance to death receptor—induced apoptosis through mutational inactivation of the proapoptotic Bcl-2 homolog Bax," *Nat. Med.*, 8:274-281, 2002.

Lewis et al., "Efficient delivery of siRNA for inhibition of gene expression in postnatal mice," *Nature Genetics*, 32:107-108, 2002.

Li et al., "Cleavage of BID by Caspase 8 Mediates the Mitochondrial Damage in the FAS Pathway of Apoptosis," *Cell*, 94:491-501, 1998.

Li et al., "Cytochrome c and dATP-Dependent Formation of Apaf-1/Caspase-9 Complex initiates and Apoptotic Protease Cascade," *Cell*, 91:479-489, 1997.

Li et al., "DF3/MUC1 signaling in multiple myeloma cells is regulated by interleukin-7," *Cancer Biol. Ther.*, 2:187-193, 2003.

Li et al., "Heregulin targets gamma-catenin to the nucleolus by a mechanism dependent on the DF3/MUC1 oncoprotein," *Mol. Cancer Res.*, 1:765-775, 2003.

Li et al., "Human DF3/MUC1 carcinoma-associated protein functions as an oncogene," *Oncogene*, 22:6107-6110, 2003.

Li et al., "The EGF receptor regulates interaction of the human DF3/MUC1 carcinoma antigen with c-SRC and β-catenin," *JBC Papers in Press*, manuscript C100359200, Aug. 1, 2001.

Ligtenberg et al., "Cell associated episialin is a complex containing two proteins derived from a common precurso," *J. Biol. Chem.*, 267:6171-6177, 1992.

Ligtenberg et al., "Suppression of Cellular Aggregation by High Levels of Episialin," *Cancer Res.*, 52:2318-2324, 1992.

Lin et al., "Inhibition of nuclear translocation of transcription factor NF-kappa B by a synthetic peptide containing a cell membrane-permeable motif and nuclear localization sequence," *J. Biol. Chem.*, 270:14255-8, 1995.

Liu et al., "Identification of a functionally important sequence in the cytoplasmic tail of integrin beta 3 by using cell-permeable peptide analogs," *Proc. Natl Acad. Sci. U.S.A.*, 93:11819-24, 1996.

Liu et al., "Induction of Apoptotic Program in Cell-Free Extracts: Requirement of dATP and Cyochrome c," *Cell*, 86:147-157, 1996.

Lundy et al., "Monoclonal antibody DF3 correlates with tumor differentiation and hormone receptor status in breast cancer patients," *Breast Cancer Res. Treat.*, 5:269-276, 1985.

Luo et al., "Bid, a Bcl2 Interacting Protein, Mediates Cytochrome c Release from Mitochondria in Response to Activation of Cell Surface Death Receptors," *Cell*, 94:481-490, 1998.

Makimura et al., "Reducing hypothalamic AGRP by RNA interference increases metabolic rate and decreases body weight without influencing food intake," *BMC Neuroscience*, 3:18, 2002.

Manome et al., "Enhancer sequences of the DF3 gene regulate expression of the herpes simplex virus thymidine kinase gene and confer sensitivity of human breast cancer cells to ganciclovir," *Cancer Research*, 54:5408-5413, 1994.

Maraveyas et al., "Pharmacokinetics and toxicity of an Yttrium-90-CITC-DTPA-HMFG1 radioimmunoconjugate for intraperitoneal radioimmunotherapy of ovarian cancer," *Cancer*, 73:1067-1075, 1994.

Maraveyas et al., "Pharmacokinetics, biodistribution, and dosimetry of specific and control radiolabeled monoclonal antibodies in patients with primary head and neck squamous cell carcinoma," *Cancer Research*, 55:1060-1069, 1995.

Mariani et al., "Regulation of cell surface APO-1/Fas (CD95) ligand expression by metalloproteases," *Eur. J. Immunol.*, 25:2303-2307, 1995.

Marsters et al., "A novel receptor for Apo2L/TRAIL contains a truncated death domain," *Curr. Biol.*, 7:1003-1006, 1997.

Martinez et al., "Single-stranded antisense siRNAs guide target RNA cleavage in RNAi," *Cell*, 110:563-574, 2002.

Martins, "The serine protease Omi/HtrA2: a second mammalian protein with a Reaper-like function," *Cell Death Diff.*, 9:699-701, 2002.

McGrath et al., "The Yeast STE6 gene encodes a homologue of the mammalian mulitdrug resistance P-Glycoprotein," *Nature.*, 340:400, 1989.

McGuckin et al., "Prognostic significance of MUC1 epithelial mucin expression in breast cancer," *Human Pathology*, 26:432-439, 1995.

Melani et al., "Inhibition of proliferation by c-myb antisense oligodeoxynucleoides in colon adenocarcinoma cell lines that express c-myb," *Cancer Research*, 51:2897-2901, 1991.

Mi et al., "Characterization of a class of cationic peptides able to facilitate efficient protein transduction in vitro and in vivo," *Mol. Ther.*, 2:339-47, 2000.

Milik et al., "Lung lymphocyte elimination by apoptosis in the murine response to intratracheal particulate antigen," *J. Clin. Invest.*, 99:1082-1091, 1997.

Molenaar et al., "XTcf-3 transcription factor mediates beta-catenin-induced axis formation in Xenopus embryos," *Cell*, 86:391-9, 1996.

Morris et al., "A new peptide vector for efficient delivery of oligonucleotides into mammalian cells," *Nucleic Acid Res.*, 25:2730-6, 1997.

Muzio et al., "FLICE, A Novel FADD-Homologous ICE/CED-3-like Protease, Is Recruited to the CD95 (fas/APO-1) Death-Inducing Signaling Complex," *Cell*, 85:817-827, 1996.

Nagai and Sato, "Synthesis of a bicylic dipeptide with the shape of beta-turn central part," *Tet. Lett.*, 26:647-50, 1985.

Nagata, "Apoptosis by Death Factor," *Cell*, 88:355-365, 1997.

Nakashima et al., "Inhibition of angiogenesis by a new isocoumarin, NM-3,"*J. Antibiotics*, 52:426-428, 1999.

Neyfakh et al., "Efflux-mediated multidrug resistance in *Bacillus subtilis*: similarities and dissimilarities with the mammalian system," *Proc. Natl. Acad. Sci. USA*, 88:4781-4785, 1991.

Nicholson et al., "Radioimmunotherapy after chemotherapy compared to chemotherapy alone in the treatment of advanced ovarian cancer: a matched analysis," *Oncology Reports* 5:223-226, 1998.

Niethammer et al., "CRIPT, a novel postsynaptic protein that binds to the third PDZ domain of PSD-95/SAP90," *Neuron*, 20:693-707, 1989.

Novak and Dedhar, "Signaling through beta-catenin and Lef/Tcf," *Cell Mol. Life Sci.*, 523-37, 1999.

Obermair et al., "Expression of MUC1 splice variants in benign and malignant ovarian tumours," *Int. J. Cancer*, 100:166-171, 2002.

Oehlke et al., "Cellular uptake of an alpha-helical amphipathic model peptide with the potential to deliver polar compounds into the cell interior non-endocytically," *Biochim. Biophys. Acta.*, 1414: 127-39, 1998.

Okazaki et al., "Downregulation of gastric mucin gene expression and its biosynthesis by dexamethasone in the human," *J. Clin. Gastroenterl.*, 27(suppl. 1):S91-S92, 1998.

Oosterkamp et al., "Comparison of MUC-1 mucin expression in epithelial and non-epithelial cancer cell lines and demonstration of a new short variant form (MUC-1/Z)," *Int. J. Cancer*, 72:87-94, 1997.

Opalinska et al., "Nucleic-acid therapeutics: basic principles and recent applications," *Nature Reviews Drug Discovery*, 1:503-514, 2002.

Orkin Report & Recommendations of The Panel to Assess the NIH Investment in Research on Gene Therapy, 1995.

Padrón et al., "Selective cell kill of the combination of gemcitabine and cisplatin in multilayered postconfluent tumor cell cultures," *Anti-Cancer Drugs*, 10:445-452, 1999.

Pan et al., "An Antagonist Decoy Receptor and a Death Domain-Containing Receptor for TRAIL," *Science*, 277:815-818, 1997.

Pan et al., "The Receptor for the Cytotoxic Ligand TRAIL," *Science*, 276:111-113, 1997.

Parrish et al., "Functional anatomy of a dsRNA trigger: differential requirement for the two trigger strands in RNA interference," *Molecular Cell*, 8:1077-1087, 2000.

Parry et al., "Identification of MUC1 proteolytic cleavage sites in vivo," *Biochem. Biophys. Res. Commun.*, 283:715-720, 2001.

Paszkiewicz-Gadek et al., "Biosynthesis of MUC1 mucin in human endometrial adenocarcinoma is modulated by estradiol and tamoxifen," *Gynecol. Endocrinol.*, 17:37-44, 2003.

Pavlovic et al., "Targeting of non-small cell lung cancer using HMFG1-$^{99m}$TC monoclonal antibodies," *Med Pregl.*, 46 Suppl 1:26-28, 1993.

Perey et al., "Tumor selective reactivity of a monoclonal antibody prepared against a recombinant peptide derived from the DF3 human breast carcinoma-associated antigen," *Cancer Research*, 52:2563-2568, 1992.

Perez et al., "Antennapedia homeobox as a signal for the cellular internalization and nuclear addressing of a small exogenous peptide," *J. Cell. Sci.*, 102:717-22, 1992.

Pescarolo et al., "A retro-inverso peptide homologous to helix 1 of c-Myc is a potent and specific inhibitor of proliferation in different cellular systems," *FASEB J.*, 15:31-3, 2001.

Pitti et al., "Induction of Apoptosis by Apo-2 Ligand, a New Member of the Tumor Necrosis Factor Cytokine Family," *J. Biol. Chem.*, 271:12687-12690, 1996.

Pooga et al., "Cell penetrating PNA constructs regulate galanin receptor levels and modify pain transmission in vivo," *Nature Biotech.*, 16 :857-61, 1998.

Porowska et al. ,"MUC1 expression in human breast cancer cells is altered by the factors affecting cell proliferation," *Neoplasma*, 49:104-109, 2002.

Porter et al., "A neural survival factor is a candidate oncogene in breast cancer," *Proc. Natl. Acad. Sci. USA*, 100:10931-10936, 2003.

Price et al., "Immunological and structural features of the protein core of human polymorphic epithelial mucin," *Molecular Immunology*, 27:795-802, 1990.

Price et al., "Summary report on the ISOBM TD-4 workshop: analysis of 56 monoclonal antibodies against the MUC1 mucin," San Diego, California, Nov. 17-23, 1996, *Tumor Biol.*, 19:sup. 1:1-20, 1998.

Reddish et al., "Pre-immunotherapy serum CA27.29 (MUC-1) mucin level and CD69+ lymphocytes correlate with effects of Theratope sialyl-Tn-KLH cancer vaccine in active specific immunotherapy," *Cancer Immunol. Immunother.*, 42:303-9, 1996.

Reich et al., "Small interfering RNA (siRNA) targeting VEGF effectively inhibits ocular neovascularization in a mouse model," *Molecular Vision*, 9:210-216, 2003.

Ren et al., "Protein kinase C delta regulates function of the DF3/MUC1 carcinoma antigen in beta-catenin signaling," *J. Biol. Chem.*, 277:17616-17622, 2002.

Reynolds et al., "Identification of a new catenin: the tyrosine kinase substrate p120cas associates with E-cadherin complexes," *Mol. Cell. Biol.*, 14:8333-42, 1994.

Reynolds et al., "Transformation-specific tyrosine phosphorylation of a novel cellular protein in chicken cells expressing oncogenic variants of the avian cellular src gene," *Mol. Cell. Biol.*, 9:629-38, 1989.

Rousselle et al., "New advances in the transport of doxorubicin through the blood-brain barrier by a peptide vector-mediated strategy," *Mol. Pharmacol.*, 57 :679-86, 2000.

Ruben et al., "Structural and functional characterization of human immunodeficiency virus tat protein,"*J. Virol.*, 63(1):1-8, 1989.

Sato et al., "FAP-1: A Protein Tyrosine Phosphatase That Associates with Fas," *Science*, 268:411-415, 1995.

Scaffidi et al., "Differential Modulation of Apoptosis Sensitivity in CD95 Type I and Type II Cells," *J. Biol. Chem.*, 274:22532-22538, 1999.

Schneider et al., "Mutagenesis and selection of PDZ domains that bind new protein targets," *Nat. Biotech.*, 17:170-5, 1998.

Schroeder et al., "Transgenic MUC1 interacts with epidermal growth factor receptor and correlates with mitogen-activated protein kinase activation in the mouse mammary gland," *J. Biol Chem*, 276:13057-13064, 2001.

Schultz et al., "Specific interactions between the syntrophin PDZ domain and voltage-gated sodium channels," *Nat. Struct. Biol.*, 5:19-24, 1998.

Schumacher et al., "Immunoscintigraphy with positron emission tomography: Gallium-68 chelate imaging of breast cancer pretargeted with bispecific anti-MUC1/anti-Ga chelate antibodies," *Cancer Research*, 61:3712-3717, 2001.

Sekine et al., "Purification and characterization of a high molecular weight glycoprotein detectable in human milk and breast carcinomas," *J. Immunol.*, 135:3610-3615, 1985.

Sherman et al., "Ionizing radiation regulates expression of the c-jun protooncogene," *Proc. Natl. Acad. Sci. USA*, 87:5663-5666, 1990.

Shimazui et al., "Prognostic value of cadherin-associated molecules (alpha-, beta-, and gammacatenins and p120cas) in bladder tumors," *Cancer Res.*, 56:4154-8, 1996.

Siddiqui et al., "Isolation and sequencing of a cDNA coding for the human DF3 breast carcinoma-associated antigen," *Proc. Natl. Acad. Sci. USA*, 85:2320-2323, 1988.

Sloan et al., Distribution of epithelial membrane antigen in normal and neoplastic tissues and its value in diagnostic tumor pathology, *Cancer*, 47:1786-1795, 1981.

Smith and Waterman, "Comparison of Biosequences," *Adv. Appl. Math.*, 2:482-9, 1981.

Smith, "Design, Synthesis, and Crystal Structure of a Pyrrolinon-Based Peptidomimetic Possessing the Conformation of a beta-Strand: Potential Application to the Design of Novel Inhibitors of Proteolytic Enzymes," *J. Amer. Chem. Soc.*, 114:10672-4, 1992.

Songyang et al., "Recognition of unique carboxyl-terminal motifs by distinct PDZ domains," *Science*, 275:73-7, 1997.

Soomets et al., "Deletion analogues of transportan," *Biochim. Biophys. Acta*, 1467:165-176, 2000.

Spatola, "A Peptide Backbone Modifications," In: Chemistry and Biochemistry of Amino Acids, Peptides and Proteins, 7:267-357, Marcell Dekker, NY, 1983.

Srinivasan et al., "Bcl-xL functions downstream of caspase-8 to inhibit Fas- and tumor necrosis factor receptor 1-induced apoptosis of MCF7 breast carcinoma cells," *J. Biol. Chem.*, 273:4523-4529, 1998.

Srinivasula et al., "Autoactivation of procaspase-9 by Apaf-1-mediated oligomerization," *Mol. Cell.*, 1:949-957, 1998.

Stennicke et al., "Pro-caspase-3 is a major physiologic target of caspase-8," *J. Biol. Chem.*, 273:27084-27090, 1998.

Strous and Decker, "Mucin-Type Glycoproteins," *Crit. Rev. Biochem., Mol. Biol.*, 27:57-92, 1992.

Struhl, "Delection mapping a eukaryotic promoter," *Proc. Natl. Acad. Sci. USA*, 78:4461-4465, 1981.

Subbarao et al., "pH-dependent bilayer destabilization by an amphipathic peptide," *Biochemistry*, 26:2964-2972, 1987.

Swallow et al., "The human tumour-associated epithelial mucins are coded by an expressed hypervariable gene locus PUM," *Nature*, 328:82-84, 1987.

Takeichi, "Cadherins: a molecular family important in selective cell-cell adhesion," *Annu. Rev. Biochem.*, 59:237-52, 1990.

Taylor et al., "Antisense oligonucleotides: a systematic high-throughput approach to target validation and gene function determination," *Drug Discovery Today*, 4:562-567, 1999.

Timmer et al., "Fas receptor-mediated apoptosis: a clinical application?" *J. Pathol.*, 196:125-134, 2002.

Tondini et al., "Comparison of CA15-3 and carcinoembryonic antigen in monitoring the clinical course of patients with metastatic breast cancer," *Cancer Res.*, 48:4107-4112, 1988.

Tondini et al., "Evaluation of monoclonal antibody DF3 conjugated with ricin as a specific immunotoxin for in Vitro purging of human bone marrow," *Cancer Research*, 50:1170-1175, 1990.

Topp et al., "MUC-1 specific T-cells are present in multiple myeloma patients at high frequency after allogeneic transplantation buy may not mediated the graft versus myeloma effect," *Blood*, 100: page Abstract No. 5191, 2002.

Torchilin and Levchenko, "TAT-liposomes: a novel intracellular drug carrier," *Curr. Protein Pept. Sci.*, 4:133-40, 2003.

Tseng et al., "Translocation of liposomes into cancer cells by cell-penetrating peptides penetratin and tat: a kinetic and efficacy study," *Mol. Pharmacol.*, 62:864-72, 2002.

van Hof et al., "Biodistribution of 111Indium-labeled engineered human antibody CTMO1 in ovarian cancer patients: influence of protein dose," *Cancer Research*, 56:5179-5185, 1996.

Verhagen et al., "Identifcation of DIABLO, a Mammalian Protein that Promotes Apoptosis by Binding to and Antagonizing IAP Proteins," *Cell*, 102:43-53, 2000.

Vermeer et al., "Segregation of receptor and ligand regulates activation of epithelial growth factor receptor," *Nature*, 422:322-326, 2003.

Vives et al., "A truncated HIV-1 Tat protein basic domain rapidly translocates through the plasma membrane and accumulates in the cell nucleus," *J. Biol. Chem.*, 272 :16010-7, 1997.

Vleck et al., "Pseudorabies virus immediate-early gene overlaps with an oppositely oriented open reading frame: Characterization of their promoter and enhancer regions," *Virology*, 179:365,337, 1990.

Von Zonneveld et al., "Type 1 plasminogen activator inhibitor gene: Functional analysis and glucocorticoid regulation of its promoter," *Proc. Natl. Acad. Sci. USA*, 85:5525-5529, 1988.

Walczak et al., "TRAIL-R2: a novel apoptosis-mediating receptor for TRAIL," *EMBO J.*, 16:5386-5397, 1997.

Walczak et al., "Tumoricidal activity of tumor necrosis factor-related apoptosis-inducing ligand in vivo," *Nat. Med.*, 5:157-163, 1999.

Waldmann, "Monoclonal antibodies in diagnosis and therapy," *Science* 252:1657-1662, 1991.

Walsh et al., "Heterogeneity of MUC1 expression by human breast carcinoma cell lines in vivo and in vitro," *Breast Cancer Research and Treatment*, 58:255-266, 2000.

Wang and El-Deiry, "TRAIL and apoptosis induction by TNF-family death receptors," *Oncogene*, 24:8628-8633, 2003.

Wender et al., "The design, synthesis, and evaluation of molecules that enable or enhance cellular uptake: peptoid molecular transporters," *Proc. Natl. Acad. Sci., U.S.A.*, 97:13003-8, 2000.

Williams et al., "Selective inhibition of growth factor-stimulated mitogenesis by a cell-permeable Grb2-binding peptide," *J. Biol. Chem.*, 272:22349-54, 1997.

Wreschner et al., "Does a novel form of the breast cancer marker protein MUC1, act as receptor molecule that modulates signal transduction," In: *Antigen and Antibody Molecular Engineering in Breast Cancer Diagnosis and Treatment*, Ed. Ceriani Plenum Press, New York, pp. 17-26, 1994.

Xia et al., "siRNA-mediated gene silencing in vitro and invivo," *Nature Biotechnology*, 20:1006-1010, 2002.

Xing et al, "Synthetic peptides reactive with anti-human milk fat globule membrane monoclonal antibodies," *Cancer Research*, 50:89-96, 1990.

Xing et al., "Effect of variations in peptide sequence on anti-human milk fat globule membrane antibody reactions," *Immunology*, 72:304-311, 1991.

Xing et al., "Epitope mapping of anti-breast and anti-ovarian mucin monoclonal antibodies," *Molecular Immunology*, 29:641-650, 1992.

Xing et al., "Monoclonal antibodies reactive with mucin expressed in breast cancer," *Immunol. Cell. Biol.*, 67:183-195, 1989.

Xing et al., Second generation anti-MUC1 peptide monoclonal antibodies, *Cancer Research*, 52:2310-2317, 1992.

Yang et al., "Prevention of Apoptosis by Bcl-2: Release of Cytochrome c from Mitochondria Blocked," *Science*, 275:1129-1132, 1997.

Yeh et al., "Design of yeast-secreted albumin derivatives for human therapy: biological and antiviral properties of a serum albumin-CD4 genetic conjugate," *Proc. Natl. Acad. Sci. USA*, 89:1904-1908, 1992.

Zrihan-Licht et al., "Characterization and molecular cloning of a novel MUC1 protein, devoid of tandem repeats, expressed in human breast cancer tissue," *Eur. J. Biochem.*, 224:787-795, 1994.

Office Communication, issued in U.S. Appl. No. 10/032,786, dated Feb. 26, 2003.

Office Communication, issued in U.S. Appl. No. 10/032,786, dated Jul. 2, 2003.

Alexander et al., "Beta-catenin—A linchpin in colorectal carcinogenesis," *American Journal of Pathology*, 160:389-401, 2003.

Anderson, "Human Gene Therapy," *Nature*, 392(6679 Suppl.):25-30, 1998.

Anderson, "The current status of clinical gene therapy," *Human Gene Therapy*, 13:1261-1262, 2002.

Behrens et al., "Functional interaction of Beta-catenin with the transcription factor LEF-1," *Letter to Nature*, 382:638-342, 1996.

Branch, "A good antisense molecule is hard to find," *TIBS*, 23:45-50, 1998.

Crooke, "Basic principles of antisense therapeutics," Springer-Verlag, NY, pp. 1-50, 1998.

Crystal, "Transfer of genes to humans: Early lessons and obstacles to success," *Science*, 270:404-410, 1995.

Friedmann, "Overcoming the obstacles to gene therapy," *Scientific American*, 96-101, 1997.

Huber et al., "Nuclear localization of Beta-catenin by interaction with transcription factor LEF-1," *Mech. Develop.*, 59:3-10, 1996.

Songyang et al., "SH2 domains recognize specific phosphopetide sequencesc" *Cell*, 72:767-778, 1993.

Verma et al., "Gene therapy—promises, problems and prospects," *Nature*, 389:239-242, 389.

Office Communication, issued in Canadian Patent Application No. 2,432,276, dated Jul. 3, 2003.

Gewirtz et al., "Nucleic acid therapies: State of the art and future prospects," *Blood*, 3: 712-726, 1998.

Gay et al,, "Selective BRB2 SH2 Inhibitors as Anti-RAS Therapy", Int. J. Cancer, 83(2):235-241 (1999).

Li et al., "The Epidermal Growth Factor Receptor Regulates Interaction of the Human DF3/MUC1 Carcinoma Antigen with c-Src and β-Catenin", J. Biol. Chem., 276(38): 35239-35242 (2001).

Li et al., "The c-Src Tyrosine Kinase Regulates Signaling of the Human DF3/MUC1 Carcinoma-associated antigen with GSK3β and β-Catenin", J Biol. Chem., 276(9): 6061-6084 (2001).

Li et al., "The Human DF3/MUC1 Carcinoma-Associated Antigen Signals Nuclear Localization of the Catenin p120$^{ctn}$", Biochem. Biophys. Res. Comnunun., 281:440-443 (2001).

Pandy et al., "Association of the DF3/MUC1 Breast Cancer Antigen with Grb2 and the Sos/Ras Exchange Protein", Can. Res., 55:4000-4003 (1995).

Rawcastle et al., "Tyrosine Kinase Inhibitors. 14. Structure-Activity Relationships for Methyl-amino-substituted Derivatives of 4-[(3-Bromophenyl)amino]-6-(methylamino)-pyrido [3,4-*d*] pyrimidine (PD 158780), a Potent and Specific Inhibitor of the Tyrosine Kinase Activity of Receptors for the EGF Family of Growth Factors", J. Med. Chem., 41:742-751 (1998).

\* cited by examiner

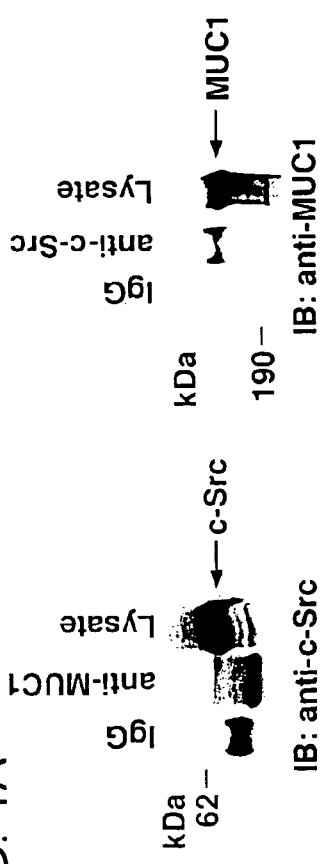
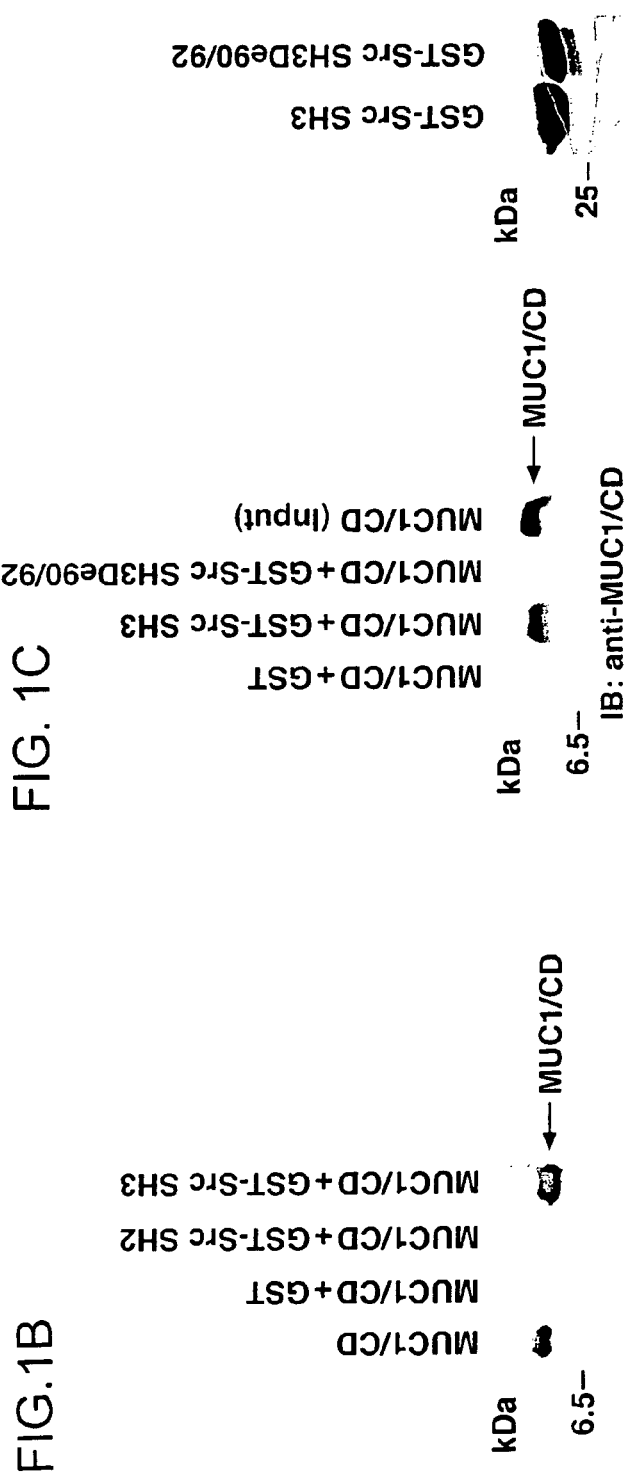
FIG. 1A
FIG. 1B
FIG. 1C

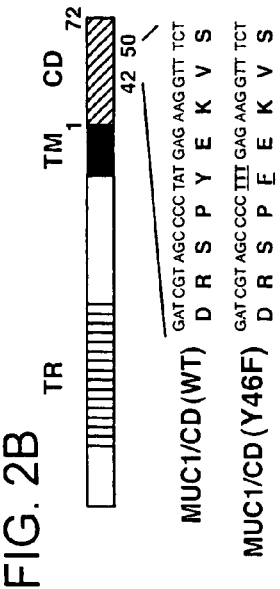
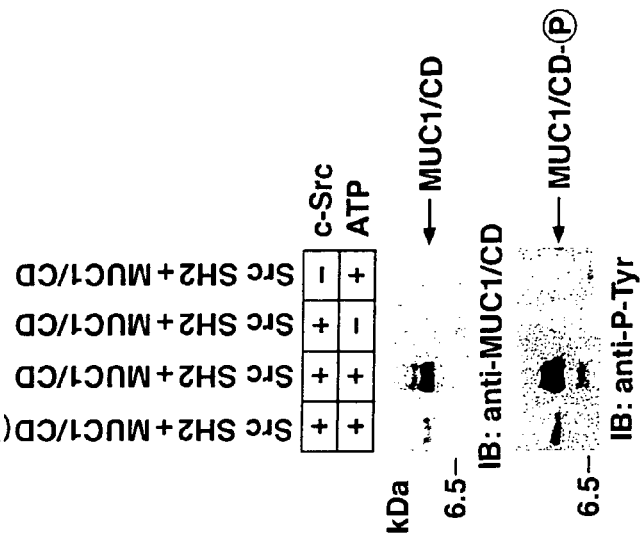
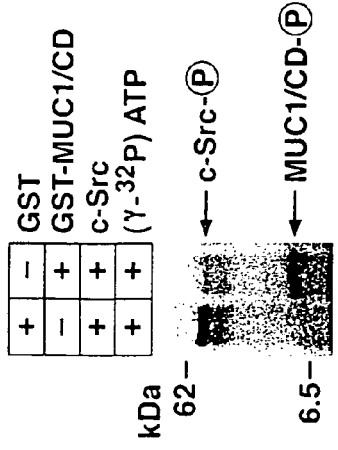
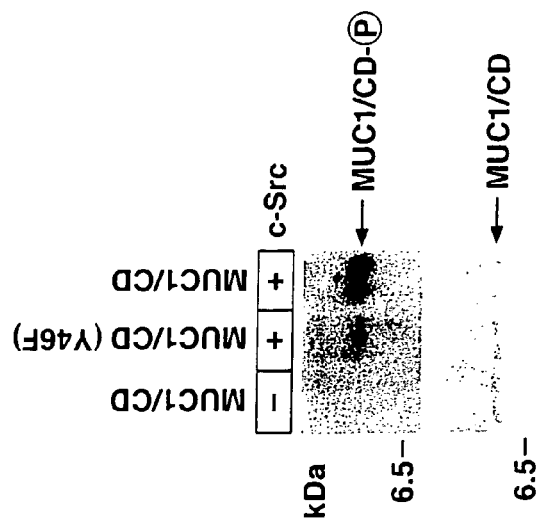
FIG. 2A
FIG. 2B
FIG. 2C
FIG. 2D

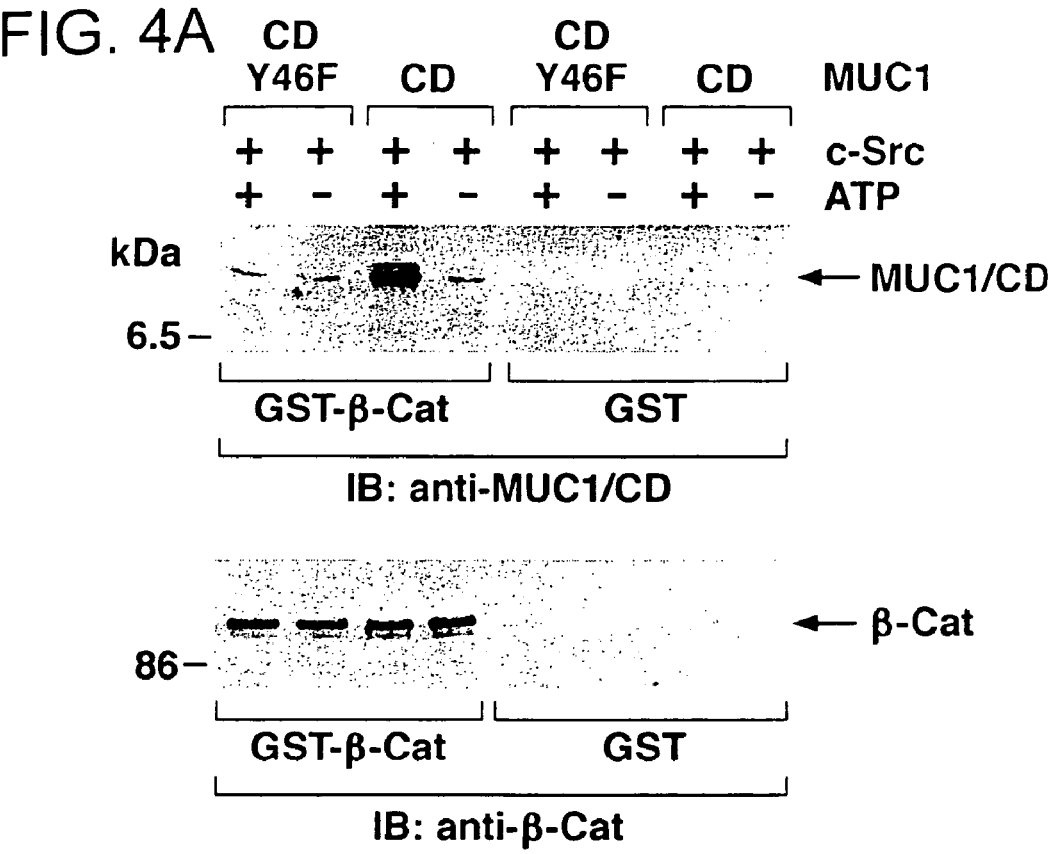

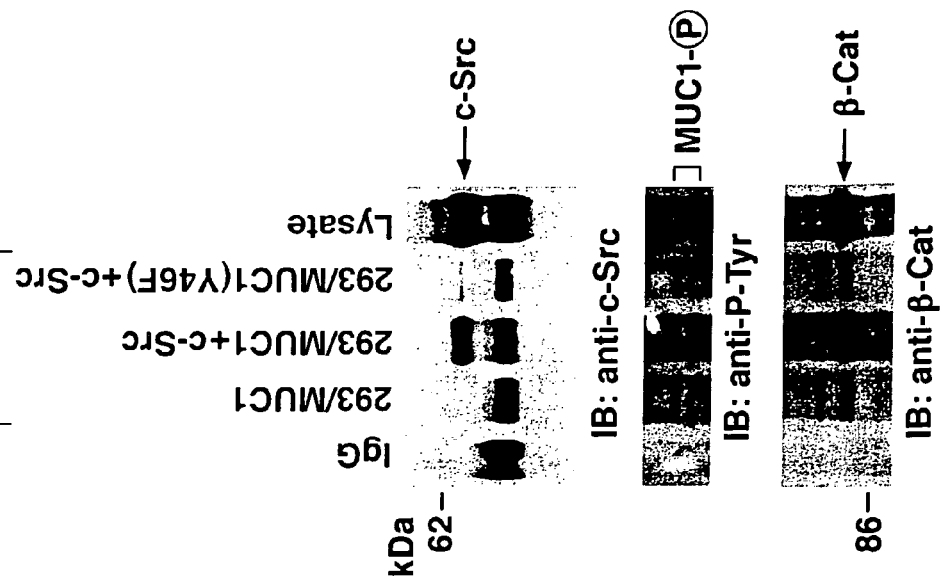
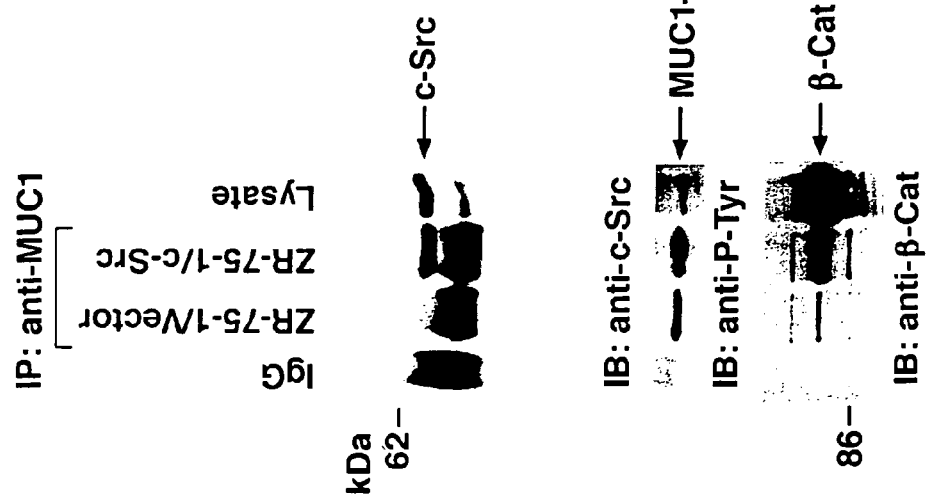

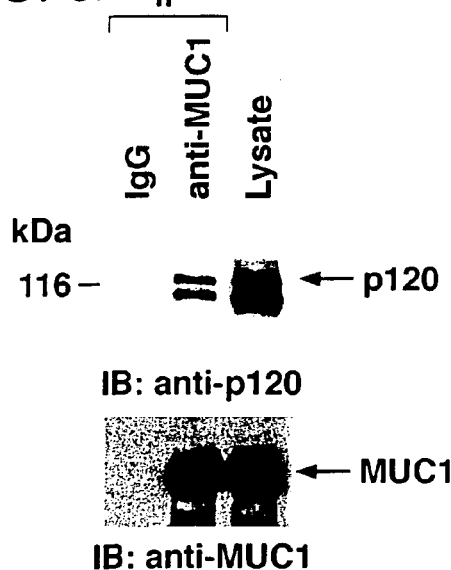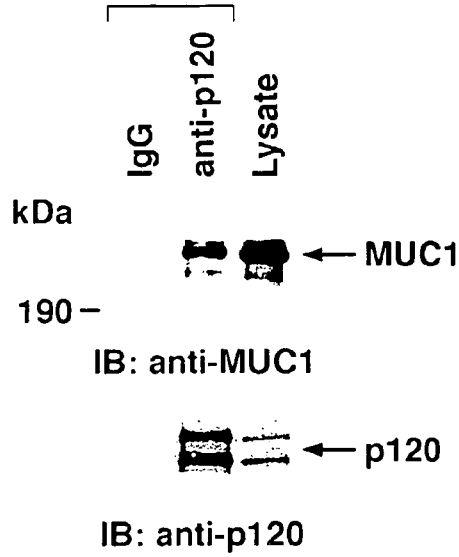

FIG. 6A
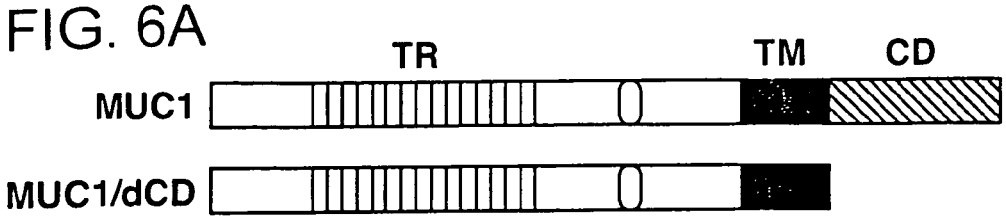
FIG. 6B
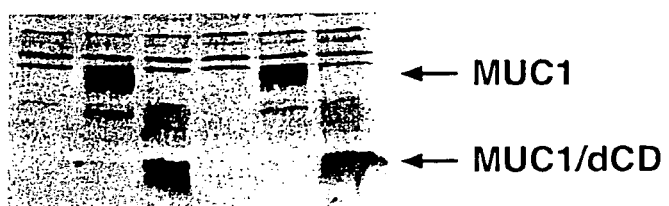
IP: anti-MUC1
IB: anti-p120
IB: anti-DF3-E
IB: anti-p120
FIG. 6C

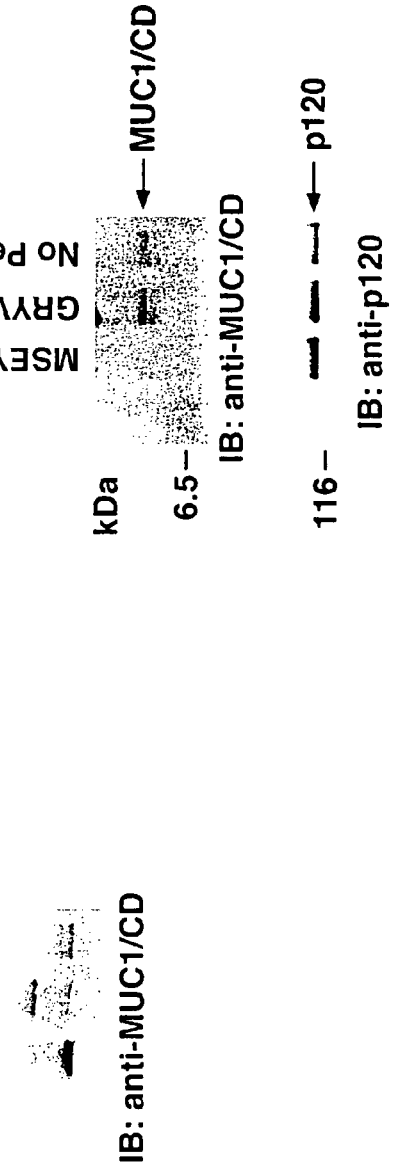

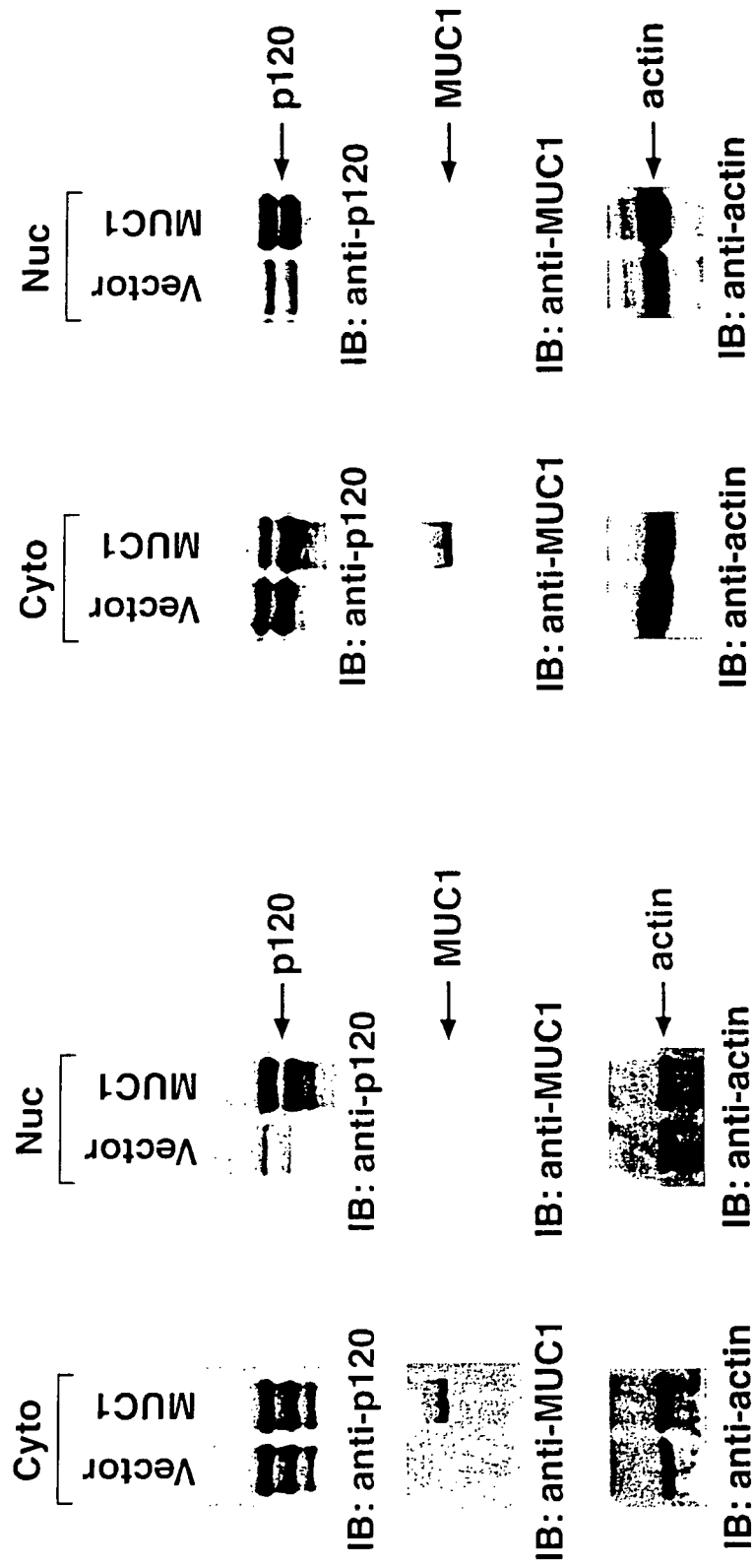

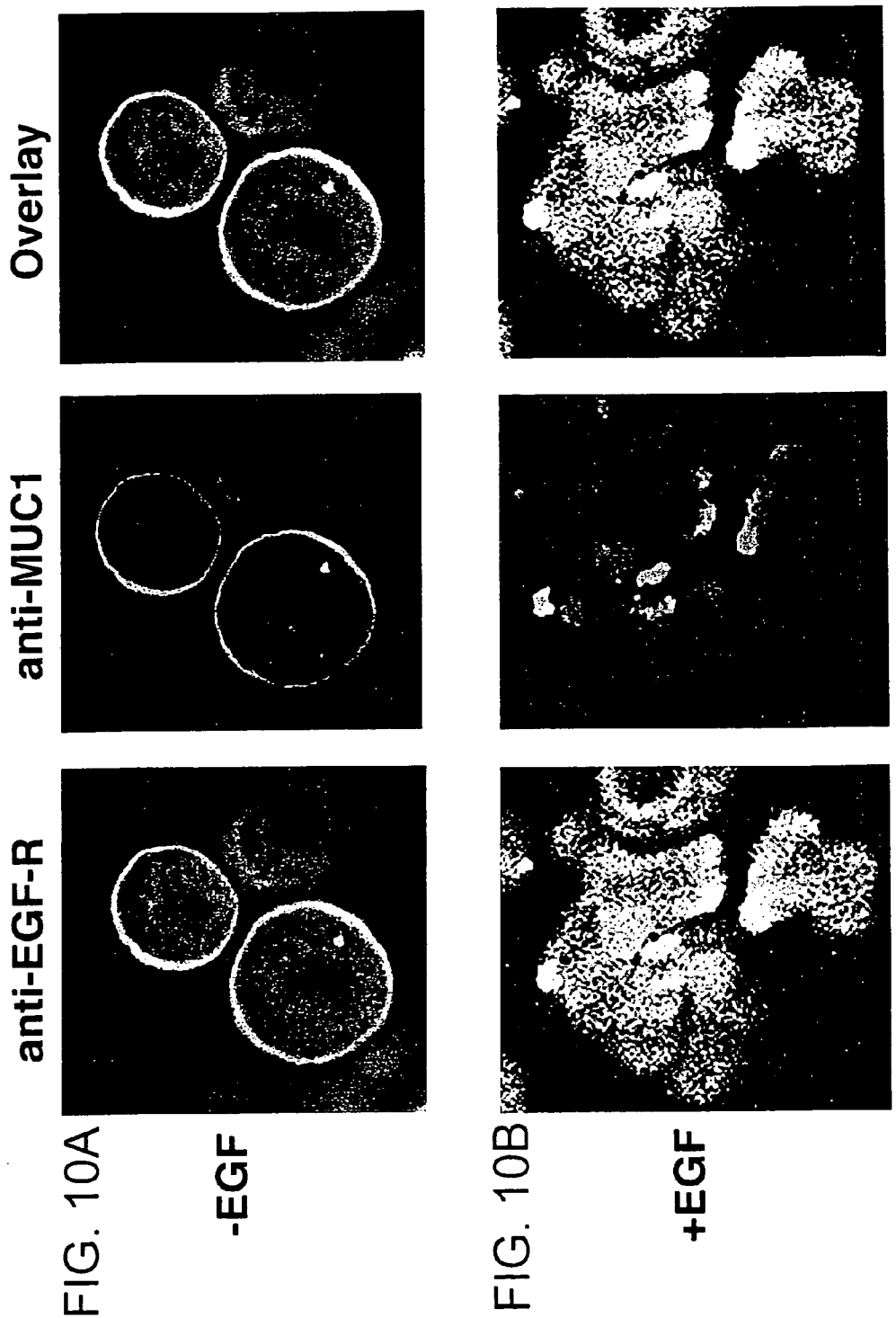

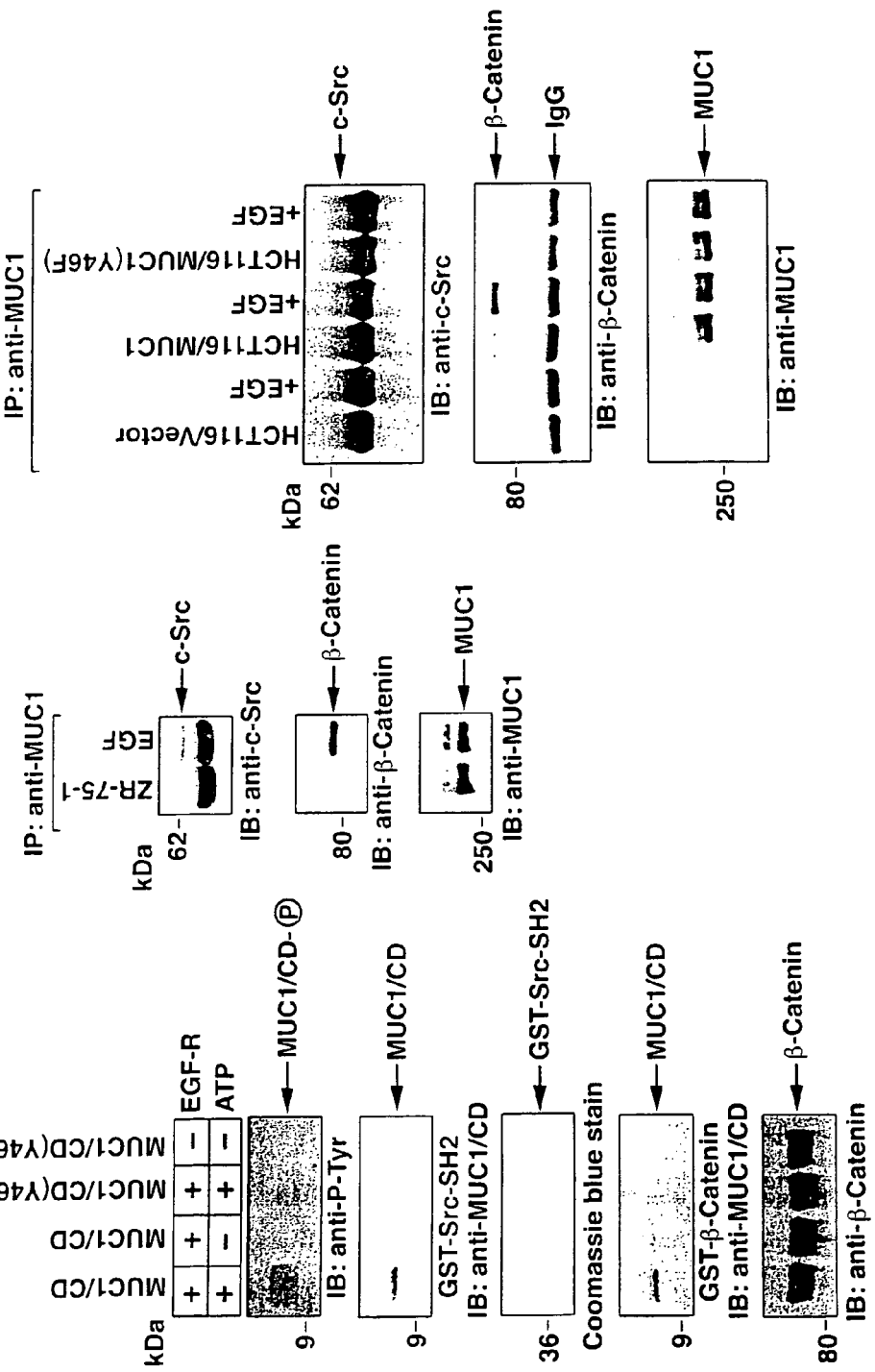

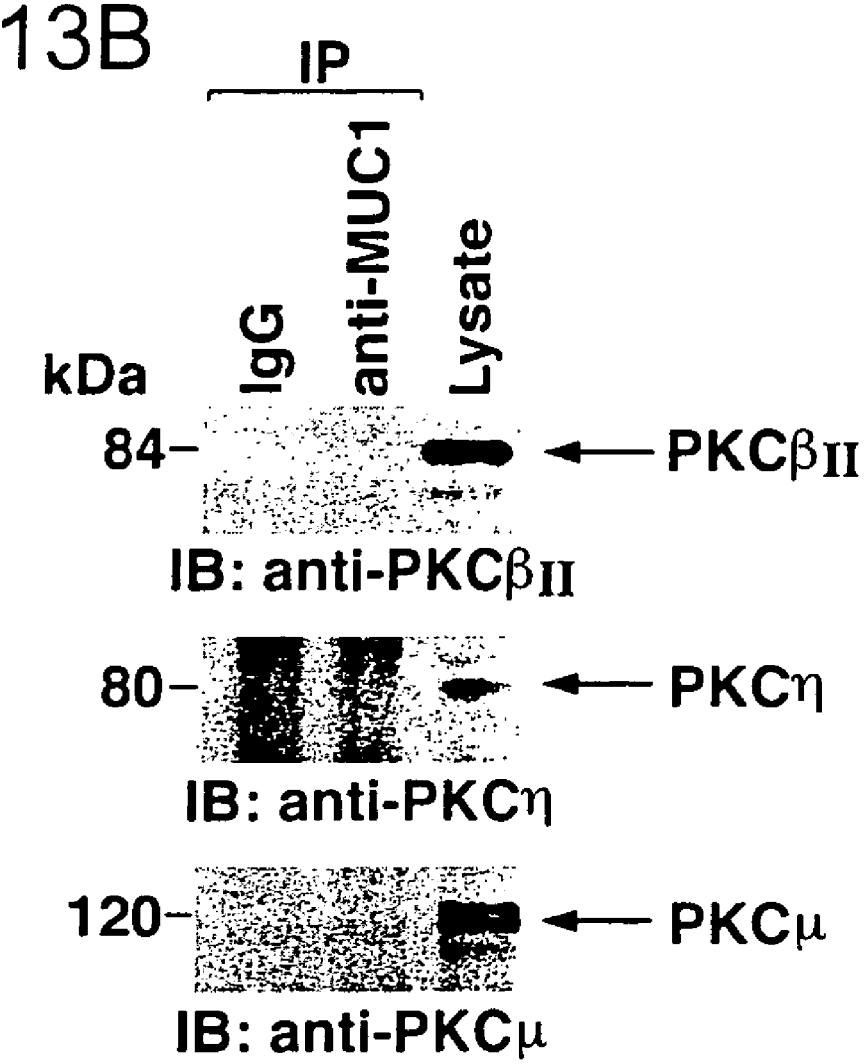

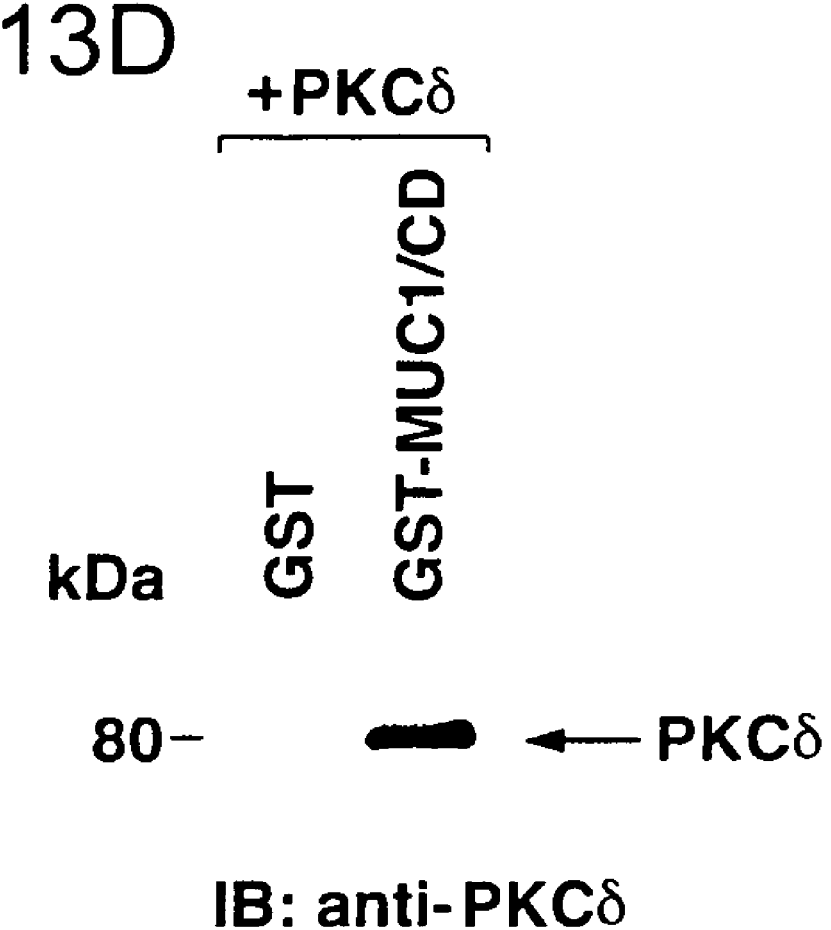

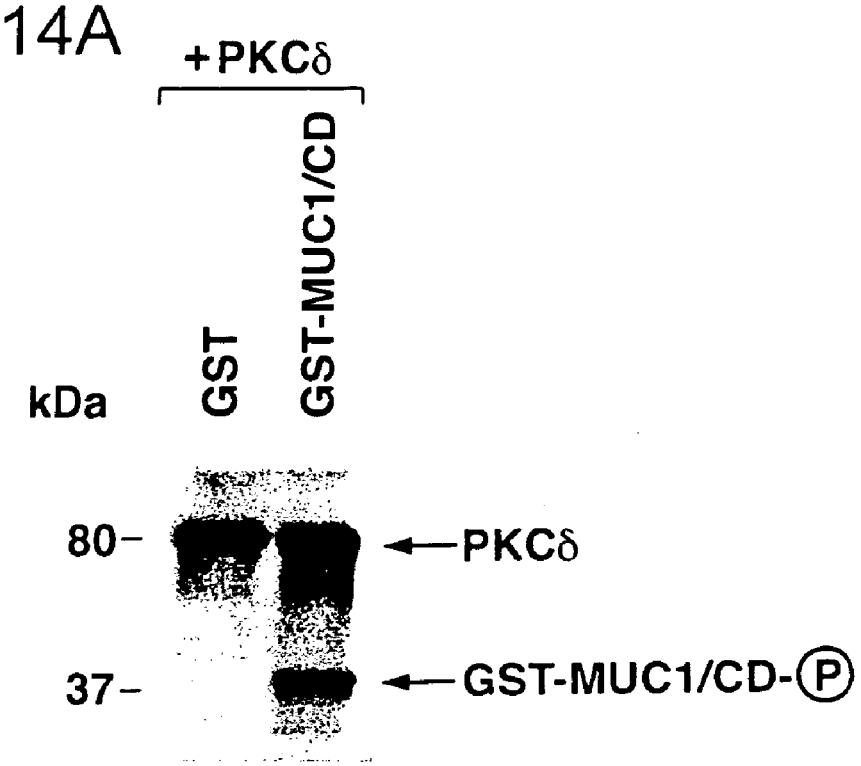

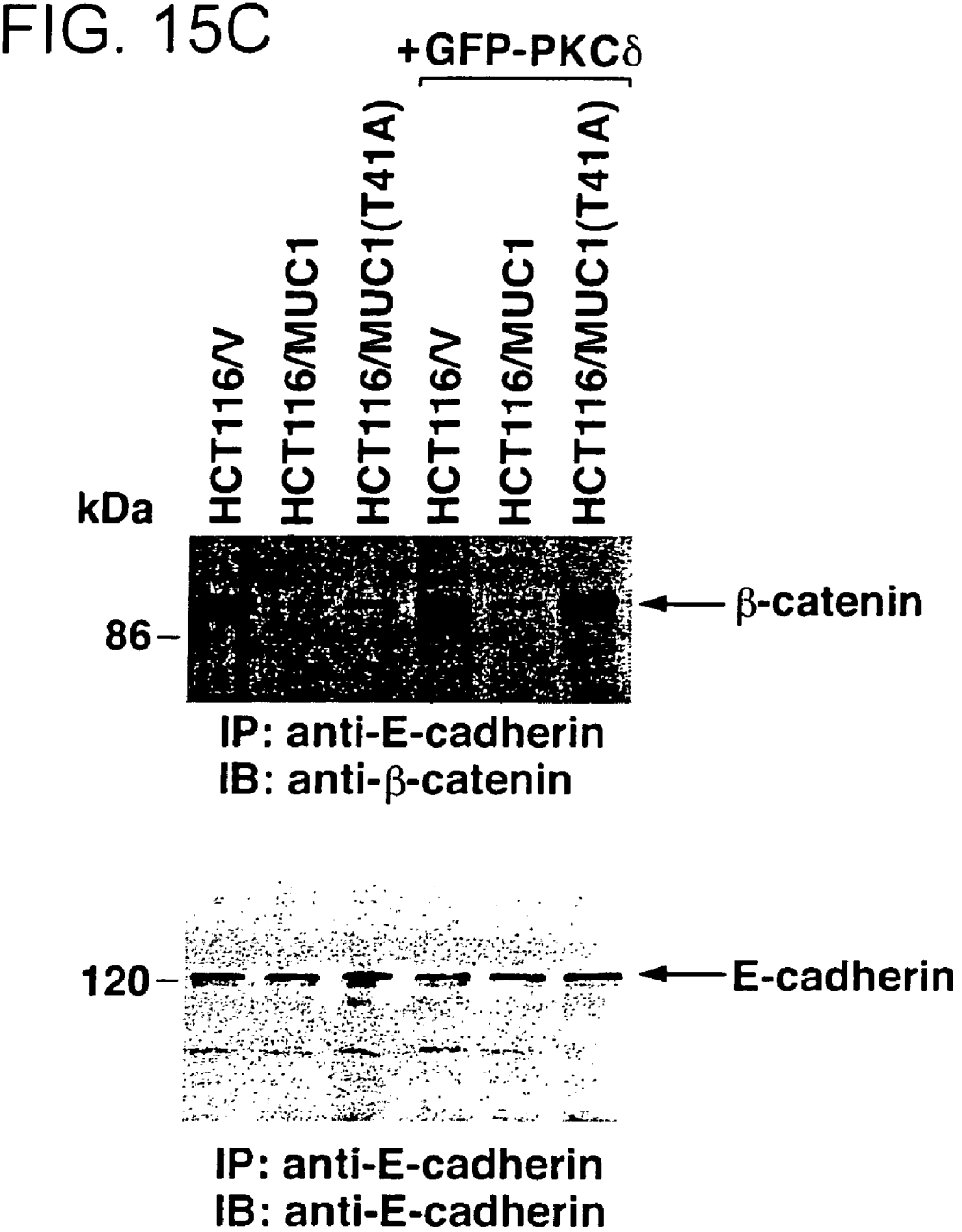

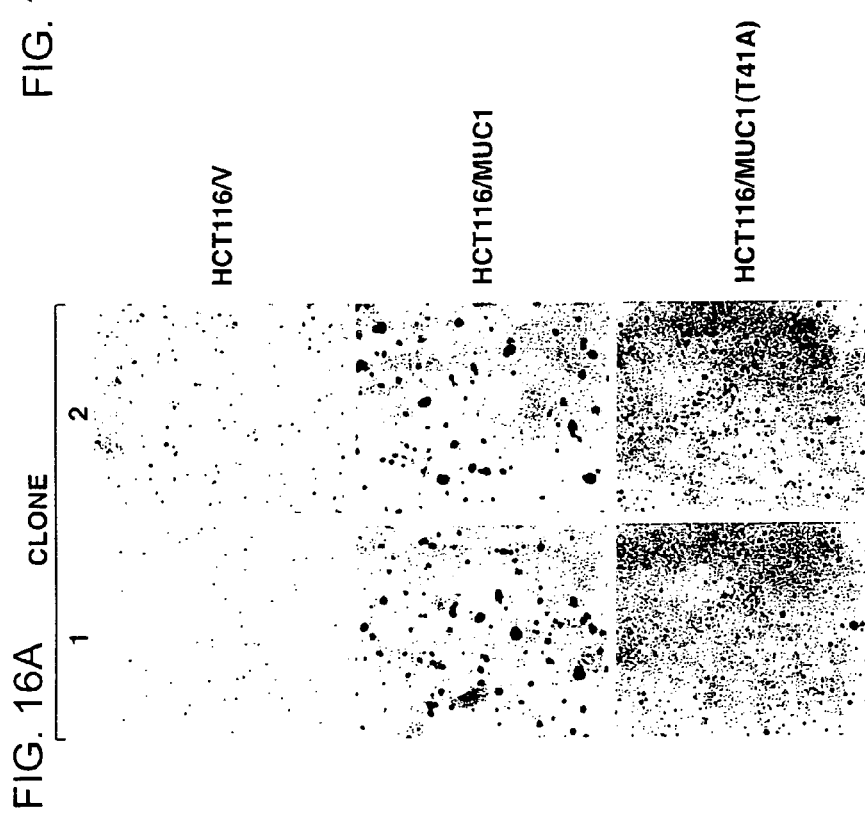
FIG. 16A
FIG. 16B
FIG. 16C

SEQUENCE LISTING

<160> NUMBER OF SEQ ID NOS: 25

<210> SEQ ID NO 1
<211> LENGTH: 72
<212> TYPE: PRT
<213> ORGANISM: Homo sapiens

<400> SEQUENCE: 1

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
    50                  55                  60

Val Ala Ala Thr Ser Ala Asn Leu
65                  70

<210> SEQ ID NO 2
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 2

Asp Arg Ser Pro Phe Glu Lys Val Ser
1               5

<210> SEQ ID NO 3
<211> LENGTH: 27
<212> TYPE: DNA
<213> ORGANISM: Homo sapiens

<400> SEQUENCE: 3
gatcgtagcc cctatgagaa ggtttct                                        27

<210> SEQ ID NO 4
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 4
gatcgtagcc cctttgagaa ggtttct                                        27

<210> SEQ ID NO 5
<211> LENGTH: 43
<212> TYPE: PRT
<213> ORGANISM: Homo sapiens

<400> SEQUENCE: 5

Cys Gln Cys Arg Arg Lys Asn Tyr Gly Gln Leu Asp Ile Phe Pro Ala
1               5                   10                  15

```
Arg Asp Thr Tyr His Pro Met Ser Glu Tyr Pro Thr Tyr His Thr His
         20                  25                  30

Gly Arg Tyr Val Pro Pro Ser Ser Thr Asp Arg
         35                  40

<210> SEQ ID NO 6
<211> LENGTH: 50
<212> TYPE: PRT
<213> ORGANISM: Homo sapiens

<400> SEQUENCE: 6

Met Ser Glu Tyr Pro Thr Tyr His Thr His Gly Arg Tyr Val Pro Pro
  1               5                  10                  15

Ser Ser Thr Asp Arg Ser Pro Tyr Glu Lys Val Ser Ala Gly Asn Gly
                 20                  25                  30

Gly Ser Ser Leu Ser Tyr Thr Asn Pro Ala Val Ala Ala Thr Ser Ala
             35                  40                  45

Asn Leu
    50

<210> SEQ ID NO 7
<211> LENGTH: 10
<212> TYPE: PRT
<213> ORGANISM: Homo sapiens

<400> SEQUENCE: 7

Met Ser Glu Tyr Pro Thr Tyr His Thr His
  1               5                  10

<210> SEQ ID NO 8
<211> LENGTH: 11
<212> TYPE: PRT
<213> ORGANISM: Homo sapiens

<400> SEQUENCE: 8

Gly Arg Tyr Val Pro Pro Ser Ser Thr Asp Arg
  1               5                  10

<210> SEQ ID NO 9
<211> LENGTH: 5
<212> TYPE: PRT
<213> ORGANISM: Homo sapiens

<400> SEQUENCE: 9

Ser Thr Asp Arg Ser
  1               5

<210> SEQ ID NO 10
<211> LENGTH: 10
<212> TYPE: PRT
<213> ORGANISM: Homo sapiens

<400> SEQUENCE: 10

Ser Ala Gly Asn Gly Gly Ser Ser Leu Ser
  1               5                  10

<210> SEQ ID NO 11
<211> LENGTH: 4
<212> TYPE: PRT
<213> ORGANISM: Homo sapiens

<400> SEQUENCE: 11
```

```
Tyr Glu Lys Val
 1

<210> SEQ ID NO 12
<211> LENGTH: 8
<212> TYPE: PRT
<213> ORGANISM: Homo sapiens

<400> SEQUENCE: 12

Asp Arg Ala Pro Tyr Glu Lys Val
 1               5

<210> SEQ ID NO 13
<211> LENGTH: 8
<212> TYPE: PRT
<213> ORGANISM: Homo sapiens

<400> SEQUENCE: 13

Ser Thr Asp Arg Ser Pro Tyr Glu
 1               5

<210> SEQ ID NO 14
<211> LENGTH: 4
<212> TYPE: PRT
<213> ORGANISM: Artificial Sequence
<220> FEATURE:
<223> OTHER INFORMATION: synthetically generated peptide

<400> SEQUENCE: 14

Phe Glu Lys Val
 1

<210> SEQ ID NO 15
<211> LENGTH: 5
<212> TYPE: PRT
<213> ORGANISM: Artificial Sequence
<220> FEATURE:
<223> OTHER INFORMATION: synthetically generated peptide

<400> SEQUENCE: 15

Ser Ala Asp Arg Ser
 1               5

<210> SEQ ID NO 16
<211> LENGTH: 8
<212> TYPE: PRT
<213> ORGANISM: Homo sapiens

<400> SEQUENCE: 16

Pro Ser Ser Thr Asp Arg Ser Pro
 1               5

<210> SEQ ID NO 17
<211> LENGTH: 8
<212> TYPE: PRT
<213> ORGANISM: Artificial Sequence
<220> FEATURE:
<223> OTHER INFORMATION: synthetically generated peptide

<400> SEQUENCE: 17

Pro Ser Ser Ala Asp Arg Ser Pro
 1               5

<210> SEQ ID NO 18
<211> LENGTH: 8
<212> TYPE: PRT
```

```
<213> ORGANISM: Artificial Sequence
<220> FEATURE:
<223> OTHER INFORMATION: synthetically generated peptide

<400> SEQUENCE: 18

Pro Ser Ser Thr Asp Arg Ala Pro
 1               5

<210> SEQ ID NO 19
<211> LENGTH: 8
<212> TYPE: PRT
<213> ORGANISM: Artificial Sequence
<220> FEATURE:
<223> OTHER INFORMATION: synthetically generated peptide

<400> SEQUENCE: 19

Pro Ser Ala Thr Asp Arg Ser Pro
 1               5

<210> SEQ ID NO 20
<211> LENGTH: 8
<212> TYPE: PRT
<213> ORGANISM: Artificial Sequence
<220> FEATURE:
<223> OTHER INFORMATION: synthetically generated peptide

<400> SEQUENCE: 20

Pro Ser Ala Thr Asp Arg Ala Pro
 1               5

<210> SEQ ID NO 21
<211> LENGTH: 24
<212> TYPE: DNA
<213> ORGANISM: Homo sapiens

<400> SEQUENCE: 21
cctagcagta ccgatcgtag cccc                                              24

<210> SEQ ID NO 22
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 22
cctagcagtg ccgatcgtag cccc                                              24

<210> SEQ ID NO 23
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 23
cctagcagta ccgatcgtgc gccc                                              24

<210> SEQ ID NO 24
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 24
```

```
cctagcgcga ccgatcgtag cccc                                          24
```

<210> SEQ ID NO 25
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 25

```
cctagcgcga ccgatcgtgc gccc                                          24
```

US 7,745,109 B2

REGULATION OF CELL GROWTH BY MUC1

This application claims priority of U.S. application Ser. No. 10/032,786, filed Dec. 26, 2001, which claims priority of U.S. Provisional Application No. 60/257,590, filed Dec. 22, 2000, and U.S. Provisional Application No. 60/308,307, filed Jul. 27, 2001.

TECHNICAL FIELD

This invention relates to regulation of cell growth, and more particularly to regulation of the growth of cancers.

BACKGROUND

The DF3/MUC1 gene encodes a high molecular weight membrane-associated glycoprotein with a mucin-like external domain. The MUC1 glycoprotein is expressed on the apical borders of secretory epithelial cells and aberrantly at high levels over the entire surface of breast, prostate, lung and other types of carcinoma cells [Kufe et al.(1984) Hybridoma 3:223-232; Perey et al. (1992) Cancer Res. 52:2563-2568]. Estimates indicate that over 500,000 new tumors overexpressing MUC1 are diagnosed each year.

SUMMARY

The inventors have discovered that MUC1 binds via its cytoplasmic domain (CD) to c-Src, epidermal growth factor receptor (EGF-R), $p120^{ctn}$ (p120), and protein kinase C$\delta$ (PKC$\delta$). In addition, they have shown that c-Src, EGF-R, and PKC$\delta$ phosphorylate the CD of MUC1, that phosphorylation of MUC1 by these kinases leads to enhanced binding of $\beta$-catenin to MUC1, and that phosphorylation by EGF-R leads to enhanced binding of c-Src to MUC1. The invention thus features methods for identifying compounds that inhibit (a) binding to MUC1 of tumor progressors (e.g., $\beta$-catenin, p120, c-Src, EGF-R, and PKC$\delta$); and (b) phosphorylation of MUC1 by tumor progressors (e.g., c-Src, EGF-R, and PKC$\delta$). The invention also includes a method for identifying a compound that enhances binding to and phosphorylation of MUC1 by glycogen synthase kinase 3$\beta$ (GSK3$\beta$). In addition, the invention features methods for inhibiting expression of MUC1 and tumor progressors in cells and methods for inhibiting binding of MUC1 to $\beta$-catenin in cells.

More specifically, the invention features a method of identifying a compound that inhibits binding of MUC1 to a tumor progressor. The method involves: (a) providing a MUC1 test agent; (b) providing a tumor progressor test agent that binds to the MUC1 test agent; (c) contacting the MUC1 test agent with the tumor progressor test agent in the presence of a test compound; and (d) determining whether the test compound inhibits binding of the MUC1 test agent to the tumor progressor test agent. The tumor progressor test agent can be, for example, a c-Src test agent, a $p120^{ctn}$ test agent, an epidermal growth factor receptor (EGF-R) test agent, a $\beta$-catenin test agent, or a protein kinase C$\delta$ (PKC$\delta$) test agent. The contacting can be carried out in a cell-free system or it can occur in a cell.

Another aspect of the invention is a method of identifying a compound that enhances binding of MUC1 to glycogen synthase kinase 3$\beta$ (GSK3$\beta$). The method involves: (a) providing a MUC1 test agent; (b) providing a GSK3$\beta$ test agent that binds to the MUC1 test agent; (c) contacting the MUC1 test agent with the GSK3$\beta$ test agent in the presence of a test compound; and (d) determining whether the test compound enhances binding of the MUC1 test agent to the GSK3$\beta$ test agent. The contacting can be carried out in a cell-free system or it can occur in a cell.

Also featured by the invention is an in vitro method of inhibiting expression of MUC1 or a tumor progressor in a cell that expresses MUC1. The method involves: (a) identifying a cell as expressing MUC1; and (b) treating the cell in vitro with an antisense oligonucleotide that hybridizes to a MUC1 transcript or to a tumor progressor transcript, wherein the antisense oligonucleotide inhibits expression of MUC1 or the tumor progressor in the cell. The tumor progressor can be, for example, $\beta$-catenin, c-Src, $p120^{ctn}$, EGF-R, or PKC$\delta$. The cell can be a cancer cell, e.g., a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. The cell can be treated with the antisense oligonucleotide itself or the treating step can be accomplished by introduction into the cell of a nucleic acid comprising a transcriptional regulatory element (TRE) (e.g., the DF3 enhancer) operably linked to a nucleic acid sequence that is transcribed in the cell into the antisense oligonucleotide.

Another embodiment of the invention is an in vitro method of inhibiting binding of MUC1 to $\beta$-catenin in a cell that expresses MUC1. The method involves: (a) identifying a cell as expressing MUC1; and (b) treating the cell in vitro with a compound that inhibits: (i) the binding of a tumor progressor to the cytoplasmic domain of MUC1; or (ii) phosphorylation of the cytoplasmic domain of MUC1 by a tumor progressor. The tumor progressor can be any of those listed above and the compound can a peptide fragment of (a) MUC1 or (b) the tumor progressor. The peptide fragment of MUC1 can be a peptide fragment of the cytoplasmic domain of MUC1, e.g., a peptide fragment with an amino acid sequence that is or contains SEQ ID NO:7. The cell can be a cancer cell, e.g., any of the cancer cells listed above. The cell can be treated with the compound itself or, where the compound is a polypeptide, the treating step can be accomplished by introduction into the cell of a nucleic acid comprising a TRE (e.g., the DF3 enhancer) operably linked to a nucleic acid sequence encoding the polypeptide.

Another aspect of the invention is a method of identifying a compound that inhibits phosphorylation of MUC1 by a tumor progressor. The method involves: (a) providing a MUC1 test agent; (b) providing a tumor progressor test agent that phosphorylates the MUC1 test agent; (c) contacting the MUC1 test agent with the tumor progressor test agent in the presence of a test compound; and (d) determining whether the test compound inhibits phosphorylation of the MUC1 test agent by the tumor progressor test agent. The tumor progressor test agent can be any of those listed above and the contacting can be carried out in a cell-free system or it can occur in a cell.

The invention also embodies an in vivo method of inhibiting binding of MUC1 to $\beta$-catenin in a cancer cell that expresses MUC1. The method involves: (a) identifying a subject as having a cancer that expresses MUC1; and (b) administering to the subject a compound or, where the compound is a polypeptide, a nucleic acid comprising a nucleic acid sequence encoding the polypeptide. The compound is one that inhibits (i) binding of a tumor progressor to the cytoplasmic domain of MUC1 or (ii) phosphorylation of the cytoplasmic domain of MUC1 by a tumor progressor. The subject can be a human patient and the cancer cell can be any of those listed above.

Also featured by the invention is an in vivo method of inhibiting expression of MUC1 or a tumor progressor in a cancer cell that expresses MUC1. The method involves: (a) identifying a subject as having a cancer that expresses MUC1; and (b) administering to the subject an antisense oligonucleotide or a nucleic acid comprising a TRE operably linked to a nucleic acid sequence that encodes the antisense oligonucleotide. The antisense oligonucleotide (i) hybridizes to a MUC1 transcript or to a tumor progressor transcript and (ii) inhibits expression of MUC1 or the tumor progressor in the cell. The subject can be a human patient and the cancer cell can be any of those listed above.

"Polypeptide" and "protein" are used interchangeably and mean any peptide-linked chain of amino acids, regardless of length or post-translational modification. The MUC-1, tumor progressor, or GSK3β text agents used in any of the methods of the invention can be wild-type or can have one or more (e.g., one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

As used herein, a "tumor progressor" is (a) β-catenin or (b) a polypeptide that binds to and/or phosphorylates one or more amino acid residues (e.g., tyrosine or threonine residues) in the cytoplasmic domain of MUC1 so as to enhance binding of β-catenin to MUC1. Tumor progressors include, for example, β-catenin, p120, c-Src, EGF-R, and PKCδ. Another tumor progressor of interest is ErbB2.

As used herein, a "tumor progressor test agent" is (a) the full-length (mature or immature) wild-type tumor progressor, (b) a fragment of the tumor progressor that is shorter than the full-length tumor progressor, or (c) (a) or (b) but with one or more (see above) conservative substitutions. Tumor progressor test agents other than full-length wild-type tumor progressors will have at least 50% (e.g., at least 50%, at least 60%, at least 70%, at least 80%, at least 90%, at least 95%, at least 98%, at least 99%, at least 99.5%, or 100% or more) of the ability of the full-length wild-type tumor progressor to bind to, or to phosphorylate, the cytoplasmic domain of MUC1. Tumor progressor test agents include, for example, β-catenin test agents, p120 test agents, c-Src test agents, EGF-R test agents, and PKCδ test agents.

As used herein, a "MUC1 test agent" is (a) full-length (mature or immature) wild-type MUC1, (b) a fragment of MUC1 that is shorter than full-length mature MUC1, or (c) (a) or (b) but with one or more (see above) conservative substitutions. Fragments of MUC1 include those that contain all or part of the CD of MUC1 and, either none, all, or part of the rest of the mature MUC1 molecule. MUC1 test agents other than full-length wild-type MUC1 will have at least 50% (e.g., at least 50%, at least 60%, at least 70%, at least 80%, at least 90%, at least 95%, at least 98%, at least 99%, at least 99.5%, or 100% or more) of the ability of full-length mature wild-type MUC1 to bind to, or be phosphorylated by the action of, the tumor progressor test agent of choice or by a GSK3β test agent.

As used herein, a "GSK3β test agent" is (a) the full-length wild-type GSK3β, (b) a fragment of GSK3β that is shorter than full-length GSK3β, or (c) (a) or (b) but with one or more (see above) conservative substitutions. GSK3β test agents other than full-length wild-type GSK3β will have at least 50% (e.g., at least 50%, at least 60%, at least 70%, at least 80%, at least 90%, at least 95%, at least 98%, at least 99%, at least 99.5%, or 100% or more) of the ability of full-length wild-type GSK3β to bind to, or to phosphorylate, the cytoplasmic domain of MUC1.

As used herein, "operably linked" means incorporated into a genetic construct so that expression control sequences effectively control expression of a coding sequence of interest.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can also be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., inhibiting the growth of cancer cells, will be apparent from the following description, from the drawings and from the claims.

DESCRIPTION OF DRAWINGS

FIG. 1A is a pair of photographs of immunoblots. A lysate from ZR-75-1 breast cancer cells was immunoprecipitated with control mouse IgG (left lane in both panels), antibody specific for MUC1 ("anti-MUC1"; middle lane of left panel), or antibody specific for c-Src ("anti-c-Src"; middle lane of right panel). The immunoprecipitates were subjected to immunoblot analysis with anti-c-Src (left panel) or anti-MUC1 (right panel). An aliquot of the lysate not subjected to immunoprecipitation was also analyzed by immunoblot analysis ("Lysate"; right lane of both panels). The positions of c-Src and MUC1 on the immunoblots are indicated.

FIG. 1B is a photograph of an immunoblot. Purified, recombinant MUC1/CD (cytoplasmic domain of MUC1) was incubated alone ("MUC-1/CD"), with glutathione-S-transferase (GST) ("MUC1/CD+GST"), GST fused to the SH2 domain of c-Src ("MUC1/CD+GST-Src SH2"), or GST fused to the SH3 domain of c-Src ("MUC1/CD+GST-Src SH3"). Proteins precipitated from these mixtures with glutathione-Sepharose 4B™ beads were subjected to immunolot analysis with an antibody specific for MUC1/CD ("anti-MUC1/CD"). The position on the immunoblot of MUC1/CD is indicated.

FIG. 1C is a photograph of an immunoblot (left panel) and a photograph of a Coomassie blue-stained sodium dodecyl sulfate polyacrylamide gel electrophoresis (SDS-PAGE) gel (right panel). Purified recombinant MUC1/CD (cytoplasmic domain of MUC1) was incubated alone ("MUC-1/CD (Input)"), with glutathione-S-transferase (GST) ("MUC1/CD+GST"), GST fused to the SH3 domain of c-Src ("MUC1/CD+GST-Src SH3"), or GST fused to the SH3 domain of c-Src in which amino acids 90-92 were deleted ("MUC1/CD+GST-Src SH3De90/92"). Proteins precipitated from these mixtures with glutathione-Sepharose 4B™ beads were subjected to immunoblot (IB) analysis with anti-MUC1/CD ("IB: anti-MUC1/CD"). The position of MUC1/CD on the immunoblot is indicated. The SDS-PAGE gel used for the immunoblot analysis was stained with Coomassie blue to assess loading of wild-type ("GST-Src SH3") and mutant ("GST-Src SH3De90/92") SH3 domains onto the gel.

FIG. 2A is a table showing the components of two phosphorylation reaction mixtures (top panel) and an autoradiogram of a SDS-PAGE gel of the two phosphorylation reaction mixtures (bottom panel). The positions of phosphorylated (P in a circle) c-Src and MUC1/CD on the autoradiogram are indicated.

FIG. 2B is a schematic representation of the MUC1 molecule showing the structure of wild-type and a mutant form of MUC1/CD. The sequence of amino acids 42-50 of the wild-type ("MUC1/CD (WT)") (SEQ ID NO:1) and mutant ("MUC1/CD (Y46F)") (SEQ ID NO:2) MUC1 CD and the nucleotide sequences of cDNA encoding wild-type (SEQ ID NO:3) and mutant (SEQ ID NO:4) are shown. Numbers indicate amino acid positions in MUC1/CD (SEQ ID NO:1). TR, tandem repeat domain; TM, transmembrane domain; CD, cytoplasmic domain.

FIG. 2C is: a table showing the components of three phosphorylation reaction mixtures (top panel); an autoradiogram of an SDS-PAGE gel of the three phosphorylation reaction mixtures (middle panel); and a photograph of a Coomassie blue stained-SDS-PAGE gel (bottom panel). The positions of phosphorylated (P in a circle) c-Src and MUC1/CD in the autoradiogram are indicated. The SDS-PAGE gel used to generate the autoradiogram was stained with Coomassie blue to assess loading of MUC1/CD onto the gel.

FIG. 2D is a table showing the substrates and presence or absence of ATP in four phosphorylation reaction mixtures (top panel), and two photographs of immunoblot analyses of the phosphorylation reaction mixtures (middle and bottom panels). The immunoblot depicted in the middle panel was stained with anti-MUC1/CD ("IB: anti-MUC1/CD"). The immunoblot depicted in the bottom panel was stained with an antibody specific for phosphotyrosine residues ("IB: anti-P-Tyr"). The positions on the immunoblots of MUC1 and phosphorylated (P in a circle) MUC1/CD are indicated.

FIG. 4A is a pair of photographs of immunoblots. Above the top panel is shown the components of eight phosphorylation reaction mixtures. The proteins in the eight different reaction mixtures were incubated with either GST or GST fused to β-catenin ("GST-β-Cat"). The resulting mixtures were incubated with glutathione-Sepharose 4B™ beads. Proteins precipitated by the beads were subjected to immunoblot analysis with anti-MUC1/CD ("IB: anti-MUC1/CD") (top panel) or antibody specific for β-catenin ("IB: anti-catenin") (bottom panel). The positions of MUC1/CD and β-catenin ("β-Cat") on the immunoblots are indicated.

FIG. 4B is a series of three photographs of immunoblots. ZR-75-1 breast cancer cells were transiently transfected with a control expression vector ("ZR-75-1/Vector") or an expression vector containing cDNA encoding c-Src ("ZR-75-1/c-Src"). Lysates from these cells were immunoprecipitated (IP) with either normal mouse IgG ("IgG") or anti-MUC1 ("IP: anti-MUC1"). These immunoprecipitates as well as unprecipitated lysate ("Lysate") from the cells transfected with the c-Src-expressing vector were subjected to immunoblot analysis with anti-c-Src ("IB: anti-c-Src") (top panel) or anti-P-Tyr ("IB: anti-P-Tyr") (middle panel), or anti-β-Cat (bottom panel). The positions of c-Src, phosphorylated (P in a circle) MUC1, and β-catenin ("β-Cat") on the immunoblots are indicated.

FIG. 4C is a series of three photographs of immunoblots. 293 cells were transiently transfected with: an expression vector containing cDNA encoding MUC1 ("293/MUC1"); an expression vector containing cDNA encoding MUC1 and an expression vector encoding c-Src ("293/MUC1+c-Src"); or an expression vector containing cDNA encoding MUC1 with the tyrosine residue at position 46 of the CD mutated to phenylalanine and an expression vector encoding c-Src ("293/MUC1(Y46F)+c-Src"). Lysates from these cells were immunoprecipitated with either normal mouse IgG ("IgG") or anti-MUC1 ("IP: anti-MUC1"). The immunoprecipitates as well as unprecipitated lysate ("Lysate") from the cells transfected with the c-Src-expressing vector were subjected to immunoblot analysis with anti-c-Src ("IB: anti-c-Src") (top panel) or anti-P-Tyr ("IB: anti-P-Tyr") (middle panel), or anti-β-Cat (bottom panel). The positions of c-Src, phosphorylated (P in a circle) MUC1, and β-catenin ("β-Cat") on the immunoblots are indicated.

FIG. 5A is pair of photographs of immunoblots. Lysates of ZR-75-1 breast cancer cells were immunoprecipitated ("IP") with anti-MUC1 ("anti-MUC1") or control IgG ("IgG"). The resulting immunoprecipitates and unprecipitated lysate were subjected to immunoblot analysis with antibody specific for p120 ("IB: anti-p120") (top panel) or anti-MUC1 ("IB: anti-MUC1") (bottom panel). The positions of p120 and MUC1 on the immunoblots are indicated.

FIG. 5B is pair of photographs of immunoblots. Lysates of ZR-75-1 breast cancer cells were immunoprecipitated ("IP") with anti-p120 ("anti-p120") or control IgG ("IgG"). The immunoprecipitates and unprecipitated lysate were subjected to immunoblot analysis with anti-p120 ("IB: anti-p120") (bottom panel) or anti-MUC1 ("IB: anti-MUC1") (top panel). The positions of p120 and MUC1 on the immunoblots are indicated.

FIG. 6A is a schematic representation of the structure of wild-type MUC1 ("MUC1") and MUC1 lacking its cytoplasmic domain ("MUC1/dCD"). TR, tandem repeat domain; TM, transmembrane domain; CD, cytoplasmic domain.

FIG. 6B is: a table indicating the vectors and the amounts (in μg) of expression vectors used to transiently transfect five aliquots of 293 cells (top panel); and three photographs of immunoblots. The vectors used were a control expression vector ("Vector"), an expression vector containing a cDNA sequence encoding MUC1 ("MUC1"), an expression vector containing a cDNA sequence encoding MUC1/dCD ("MUC1/dCD"), and an expression vector containing a cDNA sequence encoding p120. Forty-eight hours after transfection, the five transfected cell populations were lysed. An aliquot of each lysate was immunoprecipitated with anti-MUC1 ("IP: anti-MUC1"), and the immunoprecipitate was subjected to immunoblot analysis with anti-p120 ("IB: anti-p120") (top immunoblot). Aliquots of each lysate were subjected directly to immunoblot analysis with anti-MUC1 ("IB: anti-DF3-E") (middle immunoblot) or anti-p120 ("IB: anti-p120") (bottom immunoblot). The positions of MUC1, MUC1/dCD, and p120 on the immunoblots are indicated.

FIG. 6C is a photograph of an immunoblot. Purified recombinant MUC1/CD was incubated with GST ("GST") or GST fused to p120 ("GST-p120"). The resulting mixtures were incubated with glutathione-Sepharose 4B™ beads, and proteins precipitated by the beads were subjected to immunoblot analysis with anti-MUC1/CD. The position of MUC1/CD on the immunoblot is indicated.

FIG. 7A is a depiction of the amino acid sequences of MUC1/CD (SEQ ID NO:1) (top sequence), the N-terminal region of MUC1/CD ("N-MUC1/CD") (SEQ ID NO:5) (middle sequence), and the C-terminal region of MUC1/CD ("C-MUC1/CD") (SEQ ID NO:6) (bottom sequence). The numbers indicate amino acid positions in MUC1/CD (SEQ ID NO:1). The β-catenin-binding site is boxed. The GSK3β-binding and phophorylation site is singly underlined and the p120-binding site is doubly underlined.

FIG. 7B is a photograph of an immunoblot. In the table above the immunoblot is indicated which of GST and GST-p120 was incubated with either MUC1/CD, N-MUC1/CD, or C-MUC1/CD recombinant protein. Four samples containing the indicated mixtures of proteins were subjected to immunoblot analysis with anti-MUC1/CD ("IB: anti-MUC1/CD").

FIG. 7C is a pair of photographs of immunoblots. In the table above the immunoblots is indicated the mixtures of MUC1/CD, GST-p120, and GST which were incubated in the absence of inhibitor peptide (first and fourth lanes of both immunoblots) or in the presence of either a peptide with the amino acid sequence MSEYPTYHTH (SEQ ID NO:7) or a peptide with the amino acid sequence GRYVPPSSTDR (SEQ ID NO:8). The four mixtures were incubated with glutathione-Sepharose 4B™ beads and proteins precipitated by the beads were subjected to immunoblot analysis with anti-MUC1/CD ("IB: anti-MUC1/CD") (top immunoblot) or anti-p120 ("IB: anti-p120") (top immunoblot). The positions of MUC1/CD and p120 on the immunoblots are indicated.

FIG. 8A is a series of photographs of immunoblots. 293 cells were transiently transfected with a control expression vector ("Vector") or an expression vector containing a cDNA sequence encoding wild-type MUC1 ("MUC1"). Solubilized cytoplasmic ("Cyto") and nuclear ("Nuc") fractions were prepared from the transfected cells and subjected to immunoblot analysis with anti-p120 ("IB: anti-p120") (top two immunoblots), anti-MUC1 ("IB: anti-MUC1") (middle two immunoblots), or an antibody specific for actin ("IB: anti-actin") (bottom two immunoblots). The positions of p120, MUC1, and actin on the immunoblots are indicated.

FIG. 8B is a series of photographs of immunoblots. MDA-MB-231 cells were transiently transfected with a control expression vector ("Vector") or an expression vector containing a cDNA sequence encoding wild-type MUC1 ("MUC1"). Solubilized cytoplasmic ("Cyto") and nuclear ("Nuc") fractions were prepared from the transfected cells and subjected to immunoblot analysis with anti-p120 ("IB: anti-p120") (top two immunoblots), anti-MUC1 ("IB: anti-MUC1") (middle two immunoblots), or an antibody specific for actin ("IB: anti-actin") (bottom two immunoblots). The positions of p120, MUC1, and actin on the immunoblots are indicated.

FIGS. 10A and 10B are a series photomicrographs of ZR-75-1 breast cancer cells that had been cultured in the absence ("–EGF"; FIG. 10A) or presence ("+EGF"; 10 ng/ml; FIG. 10B) of epidermal growth factor (EGF) for 5 min. The cells were double-stained with anti-EGF-R (labeled with a fluorophore emitting green fluorescence) or anti-MUC1 (labeled with a fluorophore emitting red fluorescence). In the left two panels green fluorescence ("anti-EGF-R") is visualized, in the middle two panels red fluorescence ("anti-MUC1") is visualized, and in the right two panels the green fluorescent images were overlaid on the red fluorescent images ("Overlay").

FIG. 12A is a series of five photographs of immunoblots and a Coomassie blue-stained SDS-PAGE gel. Purified recombinant wild-type MUC1/CD or purified recombinant mutant MUC1/CD (Y46F) were incubated with and without purified recombinant EGF-R and with and without ATP as indicated in the table at the top of the figure. Either GST-Src-SH2 (top three photographs) or GST-β-catenin (bottom two photographs) was added to these reaction mixtures. The reaction mixtures were incubated with glutathione-Sepharose 4B™ beads and proteins precipitated by the beads were subjected to immunoblot analysis with anti-P-Tyr ("IB: anti-P-Tyr") (first panel), anti-MUC1/CD ("IB: anti-MUC1/CD") (second and fourth panel), or anti-β-catenin ("IB: anti-β-catenin") (fifth panel). Equal loading of proteins to the lanes of SDS-PAGE gels is shown by the Coomassie blue-stained gel used for immunoblot analysis shown in the second panel and by the immunoblot shown in the fifth panel. The positions of phosphorylated MUC1/CD, MUC1/CD, GST-Src-SH2, and β-catenin on the immunoblots and the Coomassie blue-stained gel are indicated.

FIG. 12B is a series of three photographs of immunoblots. ZR-75-1 breast cancer cells that had been cultured in the absence ("ZR-75-1") or presence ("EGF"; 10 ng/ml) of EGF for 5 min were lysed and the lysates were immunoprecipitated ("IP") with anti-MUC1 ("anti-MUC1"). The immunoprecipitates were subjected to immunoblot analysis with anti-c-Src ("IB: anti-c-Src") (top immunoblot), antis -catenin ("IB: anti-β-catenin") (middle immunoblot), or anti-MUC1 ("IB: anti-MUC1") (bottom immunoblot). The positions of c-Src, β-catenin, and MUC1 on the immunoblots are indicated.

FIG. 12C is a series of three photographs of immunoblots. HCT116 cells were transiently transfected with: a control expression vector ("HCT116/Vector"; first two lanes of immunoblots); an expression vector containing a cDNA sequence encoding MUC1 ("HCT116/MUC1"; middle two lanes of immunoblots); or an expression vector containing a cDNA sequence encoding MUC1 with the tyrosine residue at position 46 of MUC1/CD mutated to phenylalanine ("HCT116/MUC1 (Y46F)"; last two lanes of immunoblots). The transfected cells were cultured in the absence (lanes indicated by the acronym for relevant transfected cells) or presence (lanes indicated by "+EGF"; 10 ng/ml) of EGF for 5 min. and then lysed. The lysates were immunoprecipitated ("IP") with anti-MUC1 ("anti-MUC1"). The immunoprecipitates were subjected to immunoblot analysis with anti-c-Src ("IB: anti-c-Src") (top immunoblot), anti-β-catenin ("IB: anti-β-catenin") (middle immunoblot), or anti-MUC1 ("IB: anti-MUC1") (bottom immunoblot). The positions of c-Src, β-catenin, and MUC-1 on the immunoblots are indicated.

FIG. 12D is a depiction of the amino acid sequence of MUC1/CD (SEQ ID NO:1). Tyrosine residues (Y) at positions 8, 20, 26, 35, and 46 are shown in bold and are underlined. The GSK3β-binding and phosphorylation site (STDRS; SEQ ID NO:9), the c-Src-binding sequence (YEKV; SEQ ID NO:11), and the β-catenin-binding sequence (SAGNGGSSLS; SEQ ID NO:10) are indicated.

FIG. 13B is a series of three photographs of immunoblots. A lysate from ZR-75-1 breast cancer cells was immunoprecipitated with control mouse IgG (left lane in all three panels) or anti-MUC1 ("anti-MUC1"; middle lane in all three panels). The immunoprecipitates were subjected to immunoblot analysis with antibody specific for protein kinase Cβ$_{II}$ (top panel) ("IB: anti-PKCβ$_{II}$"), antibody specific for protein kinase Cη (middle panel) ("IB: anti-PKCη"), or antibody specific for protein kinase Cμ (bottom panel) ("IB: anti-PKCμ"). An aliquot of the lysate not subjected to immunoprecipitation was also analyzed by immunoblot analysis ("Lysate"; right lane of all three panels). The positions of PKCβ$_{II}$, PKCη and PKCμ on the immunoblots are indicated.

FIG. 13D is a photograph of an immunoblot. Purified recombinant PKCδ ("PKCδ+") was incubated with GST or GST fused to MUC1/CD ("GST-MUC1/CD"). Proteins precipitated from these mixtures with glutathione-Sepharose 4B™ beads were subjected to immunoblot ("IB") analysis with anti-PKCδ ("IB: anti-PKCδ"). The position of PKCδ on the immunoblot is indicated.

FIG. 14A is a photograph of an autoradiogram. Purified recombinant PKCδ ("+PKCδ") was incubated with [γ–$^{32}$P] ATP and GST or GST-MUC1/CD. The reaction products were analyzed by SDS-PAGE and autoradiography. The positions of PKCδ and phosphorylated (P in a circle) GST-MUC1/CD on the autoradiogram are indicated.

FIG. 15C is a pair of photographs of immunoblots. HCT116 cells were stably transfected with: a control expression vector ("HCT116/V"); an expression vector containing a cDNA sequence encoding MUC1 ("HCT116/MUC1"); or an expression vector containing a cDNA sequence encoding MUC1 with the threonine residue at position 41 of MUC1/CD mutated to alanine ("HCT116/MUC1 (T41A)"). The left three lanes of the immunoblots contain material immunoprecipitated (as described below) from these transfected cells. The right three lanes of the immunoblots contain material immunoprecipitated (as described below) from cells transfected as described for the left three lanes but additionally transfected with an expression vector containing a cDNA sequence encoding GFP-PKCδ ("+GFP-PKCδ"). Lysates prepared from the transfected cells were immunoprecipitated with anti-E-cadherin ("IP: anti-E-cadherin") and the immunoprecipitates were subjected to immunoblot analysis with anti-β-catenin ("IB: anti-β-catenin") (top panel) or anti-E-cadherin ("IB: anti-E-cadherin") (bottom panel). The positions of β-catenin and E-cadherin on the immunoblots are indicated.

FIG. 16A is a series of photomicrographs. HCT116/V, HCT116/MUC1 and HCT116/MUC1(T41A) cells (see FIG. 15C) were incubated in soft agar for three weeks. The analysis was carried out on two independently selected clones ("1" and "2") of each transfectant cell line.

FIG. 16B is a bar graph showing the number of colonies obtained in three culture dishes of each of the transfectant clones shown in FIG. 16B. V-1, clone 1 of HCT116/V; V-2, clone 2 of HCT116/V; MUC1-1, clone 1 of HCT116/MUC1; MUC1-2, clone 2 of HCT116/MUC1; T41A-1, clone 1 of HCT116/MUC1(T41A); T41A-2, clone 2 of HCT116/ MUC1(T41A).

FIG. 16C is a depiction of the amino acid sequence of MUC1/CD (SEQ ID NO:1). The PKCδ phosphorylation site (T41), the GSK3β phosphorylation site (S44), the start of the EGF-R and c-Src SH2 binding motif (Y46), and the β-catenin binding site are indicated.

DETAILED DESCRIPTION

Figure 3A:
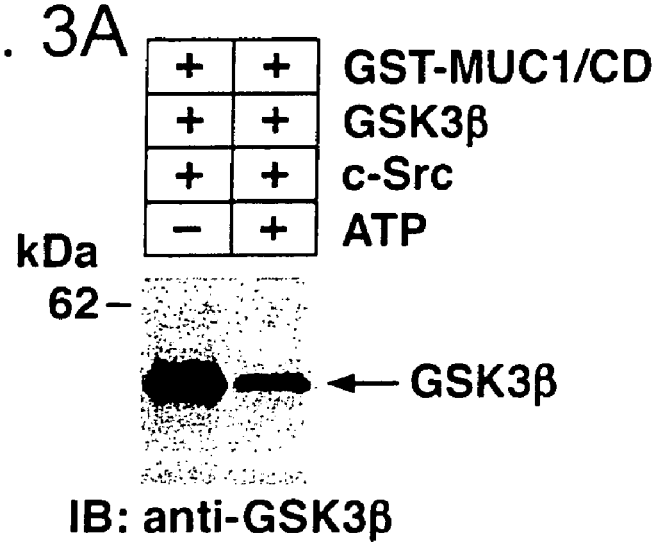
FIG. 3A is a table showing the components of two phosphorylation reaction mixtures (top panel) and a photograph of an immunoblot from an SDS-PAGE gel of the phosphorylation reaction mixtures (bottom panel). The immunoblot was stained with antibody specific for glycogen synthase kinase 3β (GSK3β) ("IB: anti-GSK3β"). The position of GSK3β on the immunoblot is shown.

The inventors have found that the tyrosine kinase c-Src binds via its SH3 domain to, and phosphorylates, the cytoplasmic domain (CD) of the human mucin molecule MUC1. In addition to other sites, c-Src phosphorylates a tyrosine residue in the a YEKV (SEQ ID NO:11) site in the CD of MUC1 (MUC1/CD), i.e., position 46 of SEQ ID NO:1. The SH2 domain of c-Src was found to bind to phosphorylated but not to unphosphorylated MUC1/CD. On the other hand, c-Src-mediated phosphorylation of MUC1/CD leads to decreased ability of MUC1/CD and glycogen synthase kinase 3β (GSK3β) to physically associate with each other. This observation was made both in cells and in a cell-free system.

It was previously shown that phosphorylation of MUC1 by GSK3β leads to decreased binding of β-catenin to MUC1 [Li et al. (1998) Mol. Cell Biol. 18:7216-7224]. The inventors have found that phosphorylation of MUC1 by c-Src leads to increased binding of β-catenin to MUC1/CD and that phosphorylation of the tyrosine residue in position 46 of the MUC1/CD (SEQ ID NO:1) is necessary for binding of β-catenin to MUC1/CD. These findings were obtained in cells and in a cell-free system.

The inventors also observed that the epidermal growth factor receptor (EGF-R) with tyrosine activity binds to and phosphorylates the CD of MUC1. Confocal microscopy experiments showed, before and after exposure of cells to epidermal growth factor (EGF), colocalization of MUC1 and EGF-R in the cell membrane. While the distribution was uniform in unstimulated cells, it was "patchy" in the cells stimulated with EGF. Phosphorylation of the CD of MUC1 by EGF-R occurs at, in addition to other sites, the tyrosine at position 46 of SEQ ID NO:1. Moreover, phosphorylation of the CD of MUC1 by EGF-R results in enhanced physical association between the MUC1 and both c-Src and β-catenin and this binding was, at least in part, dependent on the phosphorylation of tyrosine at position 46 of SEQ ID NO:1.

Experiments of the inventors showed moreover that the threonine kinase PKCδ binds to and phosphorylates the CD of MUC1. Furthermore, phosphorylation of the CD of MUC1 by PKCδ enhances binding of β-catenin to the CD of MUC1. This observation was made both in a cell-free system and in cells. Phosphorylation of threonine at position 41 of the CD domain (SEQ ID NO:1) of MUC1 by PKCδ seemed to be largely responsible for the enhanced binding of β-catenin to the CD of MUC1.

In addition, the inventors have also discovered that a member of the Armadillo repeat domain family, p120$^{ctn}$ (p120), associates with MUC1 via the CD of MUC1. Binding inhibition experiments indicate that p120 binds to the CD of MUC1 via a region of the CD of MUC1 that includes the amino acid sequence MSEYPTYHTH (SEQ ID NO:7). Expression of MUC1 in cells that do not naturally express it resulted in increased levels of p120 in the cell nuclei. It is likely that a complex of MUC1 and p120 is transported to the nucleus.

Expression of recombinant, wild-type MUC1 by HCT116 colon cancer cells was associated with decreased binding of β-catenin to E-cadherin. Moreover, expression of wild-type MUC1 by HCT116 cells resulted in increased anchorage-independent growth of the cells.

β-catenin binds to E-cadherin and, in the form of the resulting complex, is a component of the adherens junctions of mammalian epithelial cells. p120 also localizes to cell junctions. Thus, increased binding of β-catenin and/or p120 to MUC1 in cancer cells results in lower availability of β-catenin and/or p120 to be components of cell junctions and this, in turn, results in decreased avidity of cancer cell-to-cancer cell adhesion, and hence enhanced metastatic potential of relevant cancer cells. This concept is strongly supported by the above-mentioned experiments showing that expression of wild-type (but not mutant) MUC1 is associated with decreased binding of β-catenin to E-cadherin.

In addition, both β-catenin and p120 are involved in gene activation. In view of the fact that both β-catenin and p120 appear to be transported to the nucleus in the form of complexes with MUC1 subsequent to their binding of MUC1, binding of either to MUC1 can lead to enhanced gene activation and consequent enhanced tumor growth.

Thus, binding of β-catenin and /or p120 to MUC1 can increase tumor progression (by both increased cancer cell growth and metastatic potential). Moreover, in view of (1) the ability of c-Src, EGF-R, and PKCδ to bind to MUC1 and, by phosphorylation of MUC1, to enhance binding of β-catenin to MUC1 and (2) the ability of EGF-R to bind to MUC1 and, by phosphorylation of MUC1, regulate binding of c-Src to MUC1, c-Src, EGF-R, and PKCδ are likely to be indirectly involved in enhancing cancer cell progression. In contrast, since phosphorylation of MUC1 by GSK3β leads to decreased binding of β-catenin to MUC1, GSK3β likely inhibits cancer cell progression.

The inventors have demonstrated oncogenic activity of MUC1 in that normal 3Y1 mouse fibroblasts transfected with and expressing cDNA encoding MUC1 formed tumors when injected into nude mice. In addition, the role of MUC1 in enhancing cancer cell growth is shown by the fact that, as mentioned above, expression of wild-type MUC1 by HCT116 cells resulted in increased anchorage-independent growth of the cells.

Methods of Screening for Compounds

The invention provides in vitro methods for identifying compounds (small molecules or macromolecules) that: (a) inhibit binding of tumor progressors (e.g., β-catenin, p120, c-Src, EGF-R, or PKCδ) to MUC1; (b) enhance binding of GSK3β to MUC1; and (c) inhibit phosphorylation by tumor progressors (e.g., c-Src, EGF-R, or PKCδ).

These methods can be performed using: (a) isolated MUC1 test agents, tumor progressor test agents, and GSK3β test agents; or (b) cells expressing a MUC1 test agent and one or more of the tumor progressor test agents and/or a GSK3β test agent.

The term "isolated" as applied to the above-listed polypeptide test agents refers to a polypeptide or a peptide fragments which either has no naturally-occurring counterpart or has been separated or purified from components which naturally accompany it, e.g., in tissues such as pancreas, liver, spleen, ovary, testis, muscle, joint tissue, neural tissue, gastrointestinal tissue or tumor tissue, or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a test agent is at least 80%, more preferably at least 90%, and most preferably at least 99%, by dry weight, the test agent. Since a polypeptide that is chemically synthesized is, by its nature, separated from the components that naturally accompany it, a synthetic polypeptide test agent is "isolated."

An isolated polypeptide test agent can be obtained, for example, by extraction from a natural source (e.g., from tissues); by expression of a recombinant nucleic acid encoding the polypeptide; or by chemical synthesis. A polypeptide test agent that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

Prior to testing, any of the test agents can undergo modification, e.g., phosphorylation or glycosylation by methods known in the art. Phosphorylation increases the binding of some the tumor progressors (e.g., c-Src and β-catenin) to the MUC1 CD.

In methods of screening for compounds that inhibit or enhance binding of isolated MUC1 to an isolated tumor progressor or isolated GSK3δ, respectively, a MUC1 test agent is contacted with a tumor progressor test agent or a GSK3β test agent in the presence of one or more concentrations of a test compound and binding between the two test agents in the presence and absence of the test compound is detected or measured. In such assays neither of the test agents need be detectably labeled. For example, by exploiting the phenomenon of surface plasmon resonance, the MUC1 test agent can be bound to a suitable solid substrate and the tumor progressor (or GSK3β) test agent exposed to the substrate-bound MUC1 test agent in the presence and absence of the compound of interest. Binding of the tumor progressor (or GSK3β) test agent to the MUC1 test agent on the solid substrate results in a change in the intensity of surface plasmon resonance that can be detected qualitatively or quantitatively by an appropriate instrument, e.g., a Biacore apparatus (Biacore International AB, Rapsgatan, Sweden). It will be appreciated that the experiment can be performed in reverse, i.e., with the tumor progressor (or GSK3β) test agent bound to the solid substrate and the MUC1 test agent added to it in the presence of the test compound.

Moreover, assays to test for inhibition or enhancement of binding to MUC1 can involve the use, for example, of: (a) a single MUC1-specific "detection" antibody that is detectably labeled; (b) an unlabeled MUC1-specific antibody and a detectably labeled secondary antibody; or (c) a biotinylated MUC1-specific antibody and detectably labeled avidin. In addition, combinations of these approaches (including "multi-layer" assays) familiar to those in the art can be used to enhance the sensitivity of assays. In these assays, the tumor progressor (or GSK3β) test agent can be immobilized on a solid substrate such as a nylon or nitrocellulose membrane by, for example, "spotting" an aliquot of a sample containing the test agent onto a membrane or by blotting onto a membrane an electrophoretic gel on which the sample or an aliquot of the sample has been subjected to electrophoretic separation. The substrate-bound test agent is then exposed to the MUC1 test agent in the presence and absence of the test compound. After incubating the resulting mixture for a period of time and at temperature optimized for the system of interest, the presence and/or amount of MUC1 test agent bound to the tumor progressor (or GSK3β) test on the solid substrate is then assayed using a detection antibody that binds to the MUC1 test agent and, where required, appropriate detectably labeled secondary antibodies or avidin. It will be appreciated that instead of binding the tumor progressor (or GSK3β) test agent to the solid substrate, the MUC1 test agent can be bound to it. In this case binding of the tumor progressor (or GSK3β) test agent to the substrate-bound MUC1 is tested by obvious adaptions of the method described above for substrate-bound tumor progressor (or GSK3β) test agent.

The invention also features "sandwich" assays. In these sandwich assays, instead of immobilizing test agents on solid substrates by the methods described above, an appropriate test agent can be immobilized on the solid substrate by, prior to exposing the solid substrate to the test agent, conjugating a second ("capture") test agent-specific antibody (polyclonal or mAb) to the solid substrate by any of a variety of methods known in the art. The test agent is then bound to the solid substrate by virtue of its binding to the capture antibody conjugated to the solid substrate. The procedure is carried out in essentially the same manner described above for methods in which the appropriate test agent is bound to the solid substrate by techniques not involving the use of a capture antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either (a) a mAb that binds to an epitope that is either completely physically separated from or partially overlaps with any of the epitopes to which the capture polyclonal antibody binds; or (b) a polyclonal antibody that binds to epitopes other than or in addition to that to which the capture polyclonal antibody binds. Assays which involve the use of a capture and a detection antibody include sandwich ELISA assays, sandwich Western blotting assays, and sandwich immunomagnetic detection assays.

Suitable solid substrates to which the capture antibody can be bound include, without limitation, the plastic bottoms and sides of wells of microtiter plates, membranes such as nylon or nitrocellulose membranes, polymeric (e.g., without limitation, agarose, cellulose, or polyacrylamide) beads or particles.

Methods of detecting and/or for quantifying a detectable label depend on the nature of the label and are known in the art. Appropriate labels include, without limitation, radionuclides (e.g., $^{125}I$, $^{131}I$, $^{35}S$, $^{3}H$, $^{32}P$, or $^{14}C$), fluorescent moieties (e.g., fluorescein, rhodamine, or phycoerythrin), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, colorimeters, fluorometers, luminometers, and densitometers.

Candidate compounds can also be tested for their ability to inhibit or enhance binding of MUC1 to a tumor progressor (or GSK3β) in cells. The cells can either naturally express an appropriate MUC1 test agent and/or tumor progressor (or GSK3β) test agent of interest or they can recombinantly express either or both test agents. The cells can be normal or malignant and of any histological type, e.g., without limitation, epithelial cells, fibroblasts, lymphoid cells, macrophages/monocytes, granulocytes, keratinocytes, or muscle cells. Suitable cell lines include those recited in the examples, e.g., breast cancer or fibroblast cell lines. The test compound can be added to the solution (e.g., culture medium) containing the cells or, where the compound is a protein, the cells can recombinantly express it. The cells can optionally also be exposed to a stimulus of interest (e.g., a growth factor such as EGF) prior to or after exposure of the cells to the compound. Following incubation of cells expressing the test agents of interest in the absence or presence (optionally at various concentrations), physical association between the test agents can be determined microscopically using appropriately labeled antibodies specific for both test agents, e.g., by confocal microscopy. Alternatively, the cells can be lysed under non-dissociating conditions and the lysates tested for the presence of physically associated test agents. Such methods include adaptions of those described using isolated test agents. For example, an antibody specific for one of the two test agents (test agent 1) can be bound to a solid substrate (e.g., the bottom and sides of the well of a microtiter plate or a nylon membrane). After washing away unbound antibody, the solid substrate with bound antibody is contacted with the cell lysate. Any test agent 1 in the lysate, bound or not bound to the second test agent (test agent 2), will bind to the antibody specific for test agent 1 on the solid substrate. After washing away unbound lysate components, the presence of test agent 2 (bound via test agent 1 and the antibody specific for test agent 1 to the solid substrate) is tested for using a detectably labeled antibody (see above) specific for test agent 2. Alternatively, test agent 1 can be immunoprecipitated with an antibody specific for test agent 1 and the immunoprecipitated material can be subjected to electrophoretic separation (e.g., by polyacrylamide gel electrophoresis performed under non-dissociating conditions). The electrophoretic gel can then be blotted onto a membrane (e.g., a nylon or a nitrocellulose membrane) and any test agent 2 on the membrane detected and/or measured with a detectably labeled antibody (see above) specific for test agent 2 by any of the above-described methods. It is understood that in the above-described assays, test agent 1 can be either the MUC1 test agent or the tumor progressor (or GSK3β) test agent or vice versa.

The invention also relates to using MUC1 test agents and/or tumor progressor test agents to predict or design compounds that can interact with MUC1 and/or tumor progressors and potentially thereby inhibit the ability of MUC1 to interact with an appropriate tumor progressor. One of skill in the art would know how to use standard molecular modeling or other techniques to identify small molecules that would bind to appropriate sites on MUC1 and/or tumor progressors. One such example is provided in Broughton (1997) Curr. Opin. Chem. Biol. 1, 392-398. One can use similar molecular modeling methods to predict or design compounds that would, by binding to appropriate sites (e.g., allosteric sites) on either molecule, enhance the binding of MUC1 to GSK3β.

The invention also provides methods to test for the ability of a compound to inhibit phosphorylation of MUC1 by a tumor progressor. Since binding of a tumor progressor with kinase activity to MUC1 is generally necessary for phosphorylation to occur, the above described methods to test for the ability of compound to inhibit the physical interaction between MUC1 and a tumor progressor are informative as to whether the test compound will inhibit phosphorylation of MUC1 by the tumor progressor. However assays to test directly for inhibition of phosphorylation can also be performed. As for the binding inhibition/enhancement assays, methods to test for inhibition of phosphorylation can also be carried out using isolated test agents or test agents in cells.

When using isolated test agents, two test agents (i.e., a MUC1 test agent and a tumor progressor test agent with kinase activity, e.g., c-Src, EGF-R, or PKCδ) of interest, the test compound (optionally at a variety of concentrations), and source of phosphate ions (e.g., ATP) are mixed. The reaction mixture is incubated under conditions readily determinable by one of skill in the art and the presence of phosphate groups on MUC1 can tested for by any of a variety of methods known in the art. The MUC1 test agent (free or complexed with the tumor progressor agent) can be separated (e.g., by immunoprecipitation, electrophoretically, or by any suitable chromatographic method known in the art) from the reaction mixture and the presence of phosphate groups on the MUC1 test agent detected by any of a variety of methods known in the art. For example, if some or all the molecules of the source of phosphate ions (e.g., ATP) include a radionuclide (e.g., $^{32}$P) in the phosphate ion, the phosphate groups on the separated MUC1 test agent can be detected and/or measured using a radioactivity or scintillation counter. Alternatively the reaction mixture (with or without immunoprecipitation) can be separated by electrophoresis (e.g., sodium dodecyl sulfate polyacrylamide gel electrophoresis (SDS-PAGE)) and the electrophoretic gel can be exposed to x-ray film. Phosphorylation of the relevant MUC1 test agent is evidenced by the presence of a dark band at an appropriate position (defined by the molecular weight of the MUC1 test agent) on the x-ray film. The degree of phosphorylation of the MUC1 test agent bands can be quantitated by densitometry.

In other methods, the source of phosphate ions (e.g., ATP) need not contain a radionuclide. In this case, the reaction mixture, or the MUC1 tested agent separated (e.g., by immunoprecipitation) from the reaction mixture, can be subjected to electrophoresis. Phosphorylated versus non-phosphorylated MUC1 test agent can be discriminated purely on the basis of mobility shift. The more phosphate groups on a polypeptide, the slower the polypeptide migrates. Alternatively, the electrophoretic gel can be blotted onto a membrane and stained with an antibody specific for the phosphorylated amino acid of interest; such amino acids include tyrosine, threonine, and serine. In yet another method, MUC1 separated from the reaction mixture (e.g., by immunoprecipitation or acid precipitation) can be digested with proteolytic enzymes and the resulting product subjected to, for example, mass spectroscopy or thin layer chromatography. Other methods for detecting and/or measuring phosphorylation of proteins are known in the art.

When inhibition of phosphorylation is tested in cells, the cells can be as described for testing for inhibition of binding. The test mixture can contain an exogenous source of phosphate ions (e.g., ATP) or intracellular stores of appropriate molecules can be relied upon. Where it is desired to detect phosphate groups on a MUC1 test agent radiometrically, naturally an exogenous source of radiolabelled phosphate (e.g., [$^{32}$P]-ATP) is added to the reaction mixture. As for the binding inhibition assays, the test compound can be added to the solution containing the cells or the cells can express it recombinantly.

A candidate compound whose presence requires at least 1.5 fold (e.g., 2-fold, 4-fold, 6-fold, 10-fold, 100-fold, 1000-fold, 10,000 fold, or 100,000-fold) more of a given MUC1 test agent to achieve a defined arbitrary level of binding to a fixed amount of a tumor progressor test agent than is achieved in the absence of the compound can be useful for inhibiting the interaction between MUC1 and the relevant tumor progressor, and thus can be useful as a cancer therapeutic agent. Alternatively, a candidate compound whose presence requires at least 1.5 fold (e.g., 2-fold, 4-fold, 6-fold, 10-fold, 100-fold, 1000-fold, 10,000 fold, or 100,000-fold) more of a given tumor progressor test agent to achieve a defined arbitrary level of binding to a fixed amount of a MUC1 test agent than is achieved in the absence of the compound can be useful for inhibiting the interaction between MUC1 and the relevant tumor progressor, and thus can be useful as a cancer therapeutic agent.

In addition, a candidate compound whose presence requires at least 1.5 fold (e.g., 2-fold, 4-fold, 6-fold, 10-fold, 100-fold, 1000-fold, 10,000 fold, or 100,000-fold) less of a given MUC1 test agent to achieve a defined arbitrary level of binding to a fixed amount of a GSK3β test agent than is achieved in the absence of the compound can be useful for enhancing the interaction between MUC1 and GSK3β, and thus can be useful as a cancer therapeutic agent. Alternatively, a candidate compound whose presence requires at least 1.5 fold (e.g., 2-fold, 4-fold, 6-fold, 10-fold, 100-fold, 1000-fold, 10,000 fold, or 100,000-fold) less of a given GSK3β test agent to achieve a defined arbitrary level of binding to a fixed amount of a MUC1 test agent than is achieved in the absence of the compound can be useful for enhancing the interaction between MUC1 and GSK3β, and thus can be useful as a cancer therapeutic agent.

Moreover, a candidate compound whose presence requires at least 1.5 fold (e.g., 2-fold, 4-fold, 6-fold, 10-fold, 100-fold, 1000-fold, 10,000 fold, or 100,000-fold) more of a given tumor progressor test agent to achieve a defined arbitrary level of phosphorylation of a MUC1 test agent (under the conditions of the relevant assay) than is achieved in the absence of the compound can be useful for inhibiting phosphorylation of MUC1 by the relevant tumor progressor, and thus can be useful as a cancer therapeutic agent.

Methods of Inhibiting Binding of MUC1 to β-catenin in a Cell

The invention features a method of inhibiting binding of MUC1 to β-catenin in cell. The method involves introducing into the cell a compound that inhibits: (a) the binding of a tumor progressor to the MUC1 (e.g., to the MUC1 cytoplasmic domain; and/or (b) phosphorylation of MUC1 (e.g., in the cytoplasmic domain of MUC1). Prior to introduction of the compound into the cell, the cell (or another cancer cell from the subject from which the cell to be treated was obtained) can optionally be tested for MUC1 expression. This can be done by testing for expression of either MUC1 protein or MUC1 mRNA by any of a wide variety of methods known in the art.

The compound can be one identified by the methods described above. Compounds useful for this method include those that: (a) inhibit binding between MUC1 and a tumor progressor (and thus also inhibit phosphorylation of MUC1 by the tumor progressor where tumor progressor has kinase activity); and (b) those that do not necessarily inhibit binding of a tumor progressor but inhibit phosphorylation of MUC1 by the tumor progressor.

Examples of compounds in category (a) are peptide fragments of the CD of MUC1 that bind to tumor progressors (e.g., a peptide fragment containing or consisting of the amino acid sequence MSEYPTYHTH (SEQ ID NO:7)) and fragments of tumor progressors (substantially lacking kinase activity or lacking the ability to effect phosphorylation of the tyrosine residue at position 46 of the CD of MUC1 (SEQ ID NO:1)) that bind MUC1. An appropriate fragment of the CD of MUC1 can be one containing or consisting of the amino acid sequence YEKV (SEQ ID NO:11) (e.g., a peptide containing or consisting of the amino acid sequence DRAPYEKV; SEQ ID NO:12). Peptides containing the YEKV amino acid sequence can contain up to 50 (e.g., one, two, three, four, five, six, seven, eight, nine, ten, 12, 15, 18, 20, 25, 30, 35, 40, 45, or 50) MUC1 residues or unrelated residues on either end or on both ends of the YEKV sequence. Any MUC1 peptides to be used as inhibitors of tumor progressor binding can optionally have any phosphorylation-susceptible amino acid residues phosphorylated. Appropriate fragments of tumor progressors include peptides containing, or consisting of, all or part of SH2 and/or the SH3 domains of c-Src.

Examples of compounds in category (b) include dominant suppressor molecules which can be either fragments of the tumor progressors of any length but shorter than the full-length, mature, wild-type tumor progressors and lacking one or more kinase domains that the tumor progressors may have or having amino acids necessary for kinase function substituted so as to substantially ablate kinase activity in the fragments. Alternatively, such dominant suppressors can contain or be a full-length, mature or immature tumor progressor (or the mature tumor progressor but containing some signal peptide amino acids) but having amino acids necessary for kinase function substituted so that the fragment substantially lacks kinase activity. Compounds derived from tumor progressors and substantially lacking kinase activity will have at least five-fold (e.g., at least five-fold, at least 10-fold, at least 20-fold, at least, 40-fold, at least, 100-fold, at least 1,000-fold, at least 10,000-fold, at least 100,000-fold, or at least $10^6$-fold) lower kinase activity than the corresponding full-length, mature, wild-type tumor progressor; the compound will preferably have no detectable kinase activity. Another example of a compound in category (b) is a fragment of the CD of MUC1 containing sites (e.g., one or more residues such as the tyrosine at position 46 of SEQ ID NO:1 or the threonine at position 41 of SEQ ID NO:1) susceptible to phosphorylation by a tumor progressor. An example of such a compound is the peptide described above containing or consisting of the amino acid sequence YEKV (SEQ ID NO:11). Another example of such a compound is a peptide (derived from the CD of MUC1) containing or consisting of the amino acid sequence STDRS (SEQ ID NO:9) (e.g., a peptide containing or consisting of the amino acid sequence STDRSPYE (SEQ ID NO:13)). Such a peptide can contain up to 50 (e.g., one, two, three, four, five, six, seven, eight, nine, ten, 12, 15, 18, 20, 25, 30, 35, 40, 45, or 50) MUC1 residues or unrelated residues on either end or on both ends of the STDRS amino acid sequence.

Methods of designing, making, and testing such compounds for the appropriate binding-inhibitory and/or phosphorylation-inhibitory activity are known to those in the art.

Cells to which the method of the invention can be applied include generally any cell that expresses MUC1. Such cells include normal cells, such as any normal epithelial cell, or a cancer cell whose proliferation it is desired to inhibit and/or whose ability to adhere to neighboring cells it is desired to enhance. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell.

The methods can be performed in vitro, in vivo, or ex vivo. In vitro application of appropriate compounds can be useful, for example, in basic scientific studies of tumor cell biology, e.g., studies on the mechanism of action of MUC1 and/or the tumor progressors listed herein in promoting tumor cell growth and/or metastasis. In addition, the compounds that are inhibitory can be used as "positive controls" in methods to identify additional compounds with inhibitory activity (see above). In such in vitro methods, cells expressing MUC1 and one or more of the tumor progressors, can be incubated for various times with the inhibitory compound(s) at a variety of concentrations. Other incubation conditions known to those in art (e.g., temperature, or cell concentration) can also be varied. Inhibition of binding and/or phosphorylation can be tested by methods such as those disclosed herein.

The methods of the invention will preferably be in vivo or ex vivo.

Compounds that inhibit binding between MUC1 and a tumor progressor and/or inhibit phosphorylation of MUC1 by a tumor progressor are generally useful as cancer cell (e.g., breast cancer cell) proliferation-inhibiting or metastasis-inhibiting therapeutics. They can be administered to mammalian subjects (e.g., human breast cancer patients) alone or in conjunction with other drugs and/or radiotherapy. As used herein, a compound that is "therapeutic" is a compound that causes a complete abolishment of the symptoms of a disease or a decrease in the severity of the symptoms of the disease. "Prevention" should mean that symptoms of the disease (e.g., cancer) are essentially absent.

When the methods are applied to subjects with cancer, prior to administration of a compound, the cancer can optionally be tested for MUC1 expression (MUC1 protein or MUC1 mRNA expression) by methods known in the art. Such methods can be performed in vitro on cancer cells obtained from a subject. Alternatively, in vivo imaging techniques using, for example, radiolabeled antibodies specific for MUC1 can be performed. In addition, body fluids (e.g., blood or urine) from subjects with cancer can be tested for elevated levels of MUC1 protein or MUC1 protein fragments.

These methods of the invention can be applied to a wide range of species, e.g., humans, non-human primates, horses, cattle, pigs, sheep, goats, dogs, cats, rabbits, guinea pigs, hamsters, rats, and mice.

In Vivo Approaches

In one in vivo approach, a compound that inhibits binding of MUC1 to a tumor progressor or phosphorylation of MUC1 by a tumor progressor (see above) is administered to a subject. Generally, the compounds of the invention will be suspended in a pharmaceutically-acceptable carrier (e.g., physiological saline) and administered orally or by intravenous infusion, or injected subcutaneously, intramuscularly, intrathecally, intraperitoneally, intrarectally, intravaginally, intranasally, intragastrically, intratracheally, or intrapulmonarily. They can also be delivered directly to tumor cells, e.g., to a tumor or a tumor bed following surgical excision of the tumor, in order to kill any remaining tumor cells. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01 µg/kg -1 g/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-,100-, 150-, or more fold). Encapsulation of the polypeptide in a suitable delivery vehicle (e.g., polymeric microparticles or implantable devices) may increase the efficiency of delivery, particularly for oral delivery.

Alternatively, where an inhibitory compound is a polypeptide, a polynucleotide containing a nucleic acid sequence encoding the polypeptide can be delivered to appropriate cells in a mammal. Expression of the coding sequence can be directed to any cell in the body of the subject. However, expression will preferably be directed to cells in the vicinity of the tumor cells whose proliferation it is desired to inhibit. Expression of the coding sequence can be directed to the tumor cells themselves. This can be achieved by, for example, the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73:479]. Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. Promoters of interest include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors, the adenoviral E1b minimal promoter, or the thymidine kinase minimal promoter. The DF3 enhancer can be particularly useful for expression of an inhibitory compound in cells that naturally express MUC1, for example, normal epithelial cells or malignant epithelial cells (carcinoma cells), e.g., breast cancer cells [see U.S. Pat. Nos. 5,565,334 and 5,874,415]. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Routes of administration can be any of those listed above.

Ex Vivo Approaches

An ex vivo strategy can involve transfecting or transducing cells obtained from the subject with a polynucleotide encoding a polypeptide that inhibit binding of MUC1 to a tumor progressor or phosphorylation of MUC1 by a tumor progressor. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the inhibitory polypeptide for as long as they survive in the subject. Alternatively, tumor cells, preferably obtained from the subject but potentially from an individual other than the subject, can be transfected or transformed by a vector encoding the inhibitory polypeptide. The tumor cells, preferably treated with an agent (e.g., ionizing irradiation) that ablates their proliferative capacity, are then introduced into the patient, where they secrete the polypeptide.

The ex vivo methods include the steps of harvesting cells from a subject, culturing the cells, transducing them with an expression vector, and maintaining the cells under conditions suitable for expression of the polypeptide that inhibits inhibit binding of MUC1 to a tumor progressor or phosphorylation of MUC1 by a tumor progressor These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can be selected, for example, for expression of the coding sequence or of a drug resistance gene. The cells may then be lethally irradiated (if desired) and injected or implanted into the patient.

Methods of Inhibiting Expression of MUC1 or a Tumor Progressor in a Cell

Also included in the invention are methods of inhibiting expression of MUC1 and/or a tumor progressor in cells. The method involves introducing into a cell (a) an antisense oligonucleotide or (b) a nucleic acid comprising a transcriptional regulatory element (TRE) operably linked to a nucleic sequence that is transcribed in the cell into an antisense RNA oligonucleotide. Prior to introduction of an antisense oligonucleotide into a cell, the cell (or another cancer cell from the subject from which the cell to be treated was obtained) can optionally be tested for expression of MUC1 as described above.

The antisense oligonucleotide and the antisense RNA hybridize to a MUC1 or a tumor progressor transcript and have the effect in the cell of inhibiting expression of MUC1 or a tumor progressor in the cell. Inhibiting expression of MUC1 or a tumor progressor in a cell can inhibit proliferation and/or enhance adhesion of the cell to neighboring cells. The method can thus be useful in inhibiting proliferation of a cancer cell and/or metastasis of a cancer cell and can thus be applied to the therapy of cancer.

Antisense compounds are generally used to interfere with protein expression either by, for example, interfering directly with translation of a target mRNA molecule, by RNAse-H-mediated degradation of the target mRNA, by interference with 5' capping of mRNA, by prevention of translation factor binding to the target mRNA by masking of the 5' cap, or by inhibiting of mRNA polyadenylation. The interference with protein expression arises from the hybridization of the antisense compound with its target mRNA. A specific targeting site on a target mRNA of interest for interaction with a antisense compound is chosen. Thus, for example, for modulation of polyadenylation a preferred target site on an mRNA target is a polyadenylation signal or a polyadenylation site. For diminishing mRNA stability or degradation, destabilizing sequences are preferred target sites. Once one or more target sites have been identified, oligonucleotides are chosen which are sufficiently complementary to the target site (i.e., hybridize sufficiently well under physiological conditions and with sufficient specificity) to give the desired effect.

With respect to this invention, the term "oligonucleotide" refers to an oligomer or polymer of RNA, DNA, or a mimetic of either. The term includes oligonucleotides composed of naturally-occurring nucleobases, sugars, and covalent internucleoside (backbone) linkages. The normal linkage or backbone of RNA and DNA is a 3' to 5' phosphodiester bond. The term also refers however to oligonucleotides composed entirely of, or having portions containing, non-naturally occurring components which function in a similar manner to the oligonucleotides containing only naturally-occurring components. Such modified substituted oligonucleotides are often preferred over native forms because of desirable properties such as, for example, enhanced cellular uptake, enhanced affinity for target sequence, and increased stability in the presence of nucleases. In the mimetics, the core base (pyrimidine or purine) structure is generally preserved but (1) the sugars are either modified or replaced with other components and/or (2) the inter-nucleobase linkages are modified. One class of nucleic acid mimetic that has proven to be very useful is referred to as protein nucleic acid (PNA). In PNA molecules the sugar backbone is replaced with an amide-containing backbone, in particular an aminoethylglycine backbone. The bases are retained and are bound directly to the aza nitrogen atoms of the amide portion of the backbone. PNA and other mimetics useful in the instant invention are described in detail in U.S. Pat. No. 6,210,289.

The antisense oligomers to be used in the methods of the invention generally comprise about 8 to about 100 (e.g., about 14 to about 80 or about 14 to about 35) nucleobases (or nucleosides where the nucleobases are naturally occurring).

The antisense oligonucleotides can themselves be introduced into a cell or an expression vector containing a nucleic sequence (operably linked to a TRE) encoding the antisense oligonucleotide can be introduced into the cell. In the latter case, the oligonucleotide produced by the expression vector is an RNA oligonucleotide and the RNA oligonucleotide will be composed entirely of naturally occurring components.

The methods of the invention can be in vitro or in vivo. In vitro applications of the methods can be useful, for example, in basic scientific studies on cell proliferation or cell adhesion. In such in vitro methods, appropriate cells (e.g., those expressing MUC1 and/or a tumor progressor), can be incubated for various lengths of time with (a) the antisense oligonucleotides or (b) expression vectors containing nucleic acid sequences encoding the antisense oligonucleotides at a variety of concentrations. Other incubation conditions known to those in art (e.g., temperature or cell concentration) can also be varied. Inhibition of MUC1 or tumor progressor expression can be tested by methods known to those in the art, e.g., methods such as those disclosed herein. However, the methods of the invention will preferably be in vivo.

The antisense methods are generally useful for cancer cell (e.g., breast cancer cell) proliferation-inhibiting and/or metastasis-inhibiting therapy. They can be administered to mammalian subjects (e.g., human breast cancer patients) alone or in conjunction with other drugs and/or radiotherapy. Prior to administration of an antisense oligonucleotide to a subject with cancer, the cancer can be tested for MUC1 expression as described above. Doses, formulations, routes of administration, vectors, and targeting are as described for in vivo approaches to inhibiting the binding of MUC1 to β-catenin in a cell. Naturally, the antisense oligonucleotides and expression vectors containing nucleic acid sequences encoding the antisense oligonucleotides will preferably be targeted to cells whose proliferation it is desired to inhibit.

The antisense methods of the invention can be applied to a wide range of species, e.g., humans, non-human primates, horses, cattle, pigs, sheep, goats, dogs, cats, rabbits, guinea pigs, hamsters, rats, and mice.

The invention also includes both in vivo and in vitro methods of inhibiting expression of MUC1 that involve the use of compounds (preferably small molecules) that inhibit transcription of the MUC1 gene or translation of MUC1 mRNA by non-antisense mechanisms. In such methods, the inhibitory compounds are either contacted in vitro with any of the cells disclosed herein or are administered to any of the subjects and by any of the doses and routes disclosed herein. Subjects will preferably be those with cancer, e.g., human cancer patients. While the invention is not limited by any particular mechanism of action, such compounds can be those that act by either inhibiting the binding and/or the activity of transcription factors or by altering the stability of MUC1 mRNA.

The invention is illustrated, not limited, by the following examples.

EXAMPLES

Example 1

Materials and Methods

Cell culture. Human ZR-75-1 breast carcinoma cells were grown in RPMI 1640 medium containing 10% heat-inactivated fetal bovine serum (HI-FBS), 100 Hg/ml streptomycin, 100 units/ml penicillin and 2 mM L-glutamine. 293 cells and HCT116 colon carcinoma cells were cultured in Dulbecco's modified Eagle's medium (DMEM) with 10% HI-FBS, 100 μg/ml streptomycin, and 100 units/ml penicillin.

In certain studies, cells were cultured in medium with 0.1% HI-FBS for 24 h and then stimulated with 10 ng/ml EGF (Calbiochem-Novabiochem, San Diego, Calif.) for 5 min at 37° C.

Lysate preparation. Subconfluent cells were disrupted on ice in lysis buffer (50 mM Tris-HCl, pH 7.6, 150 mM NaCl, 0.1% NP-40, 10 mg/ml leupeptin, 10 mg/ml aprotinin, 1 mM phenylmethylsulfonyl fluoride and 1 mM dithiothreitol) for 30 min. Lysates were cleared by centrifugation at 14,000×g for 20 min.

Immunoprecipitation and immunoblotting. Equal amounts of protein from cell lysates were incubated with normal mouse or rabbit IgG, monoclonal antibody (mAb) DF3 specific for the MUC1 glycoprotein (anti-MUC1), antibody specific for the c-Src protein (anti-c-Src) (Upstate Biotechnology, Lake Placid, N.Y.), antibody specific for EGF-R (anti-EGF-R) (Santa Cruz Biotechnology, Santa Cruz, Calif.), antibody specific for E-cadherin (anti-E-cadherin) (Santa Cruz Biotechnology), or antibody specific for PKCδ (anti-PKCδ) (Santa Cruz Biotechnology), for 2 h at 4° C. The immune complexes were precipitated with protein G agarose. After washing three times with lysis buffer, the immunoprecipitates were separated by sodium dodecyl sulfate (SDS)-polyacrylamide gel electrophoresis (PAGE) and transferred to nitrocellulose membranes. The immunoblots were probed with 500 ng/ml anti-MUC1, 1 mg/ml anti-c-Src anti-EGF-R, antibody specific for phospho-tyrosine residues (anti-P-Tyr; RC2OH; Transduction Laboratories, San Diego, Calif.) or antibody specific for B-catenin (anti-β-catenin; Zymed Laboratories, Inc., San Francisco, Calif.). Binding of these antibodies was detected with horseradish peroxidase-conjugated secondary antibodies and chemiluminescence (New Life Sciences Products, Inc., Boston, Mass.).

In other studies, lysates of ZR-75-1 cells were subjected to immunoprecipitation with either anti-MUC1 or antibody specific for p120 (anti-p120; Transduction Laboratories). Mouse IgG was used as a control. Immunoprecipitates and unprecipitated lysates were analyzed by immunoblotting with anti-p120 or anti-MUC1.

Preparation of MUC1 mutants. The MUC1/CD(Y46F) and MUC1(Y46F) mutants were generated using site-directed mutagenesis by changing Tyr-46 of a fragment of MUC1 composed of the MUC1 cytoplasmic domain of wild-type MUC1 (MUC1/CD) and full-length wild-type MUC1, respectively, to Phe. Other mutant materials referred to below were generated similarly by standard procedures.

In vitro phosphorylation. Purified wild-type and mutant MUC1/CD proteins were incubated with 1.5 units purified c-Src polypeptide (Oncogene Research Products, Cambridge, Mass.), 0.1 unit of purified EGF-R (Calbiochem-Novabiochem Co., San Diego, Calif.), or 1.0 unit purified PKCδ (Pan Vera) in 20 μl kinase buffer (20 mM Tris-HCl, pH 7.6, 10 mM $MgCl_2$, 5 mM dithiothreitol). The reaction was initiated by addition of 10 μCi [γ–$^{32}$P] ATP. After incubation for 15 min at 30° C., the reaction was stopped by addition of sample buffer and boiling for 5 min. Phosphorylated proteins were separated by SDS-PAGE and analyzed by autoradiography.

Binding studies. Purified wild-type and mutant MUC1/CD proteins were incubated with 1.5 units c-Src in the presence or absence of 200 mM ATP for 30 min at 30° C. Glutathione S-transferase (GST), GST fused to c-Src (GST-c-Src), GST fused to the SH3 domain of c-Src (GST-Src-SH3), GST fused to a mutated form of c-Src SH3 in which amino acids 90-92 are deleted (GST-Src-SH3De90/92) [Shiue et al. (1995) J. Biol. Chem. 270: 10498-10502] (provided by Dr. J. Brugge, Harvard Medical School), GST fused to the SH2 domain of c-Src (GST-Src-SH2), or GST fused to β-catenin (GST-β-catenin) was bound to glutathione beads. The beads were then added to the phosphorylation reaction mixture (described above) which was incubated for 1 h at 4° C. After washing, the proteins were subjected to SDS-PAGE and immunoblot analysis with antibody specific for the CD of MUC1 (anti-MUC1/CD) or anti-P-Tyr. In other studies, GST fused to the CD of MUC1 (GST-MUC1/CD) bound to glutathione beads was incubated with 1.5 units c-Src in the presence and absence of 200 μM ATP for 30 min at 30° C. before adding 0.1 mg purified GSK3β (New England Biolabs) and incubating for an additional 1 h. Precipitated proteins were analyzed by immunoblotting with antibody specific for GSK3β (anti-GSK3β).

In other studies, GST, GST-MUC1/CD or GST-MUC1/CD mutants bound to glutathione beads were incubated with purified recombinant PKCδ (PanVera, Madison, Wis.). The adsorbates were analyzed by immunoblotting with anti-PKCδ. In addition, purified His-tagged wild-type and mutant MUC1/CD proteins were incubated with 1.0 unit of PKCδ (Calbiochem-Novabiochem) in the absence and presence of 200 uM ATP for 30 min at 30□C. GST or GST-β-catenin bound to glutathione beads was then added, and the reaction was incubated for 1 h at 4□C. The precipitated proteins were subjected to immunoblot analysis with anti-MUC1/CD (antibody specific for the CD of MUC1).

Transient transfection studies. ZR-75-1 or 293 cells were transiently transfected with the pCMV expression vector without an expressible insert, pCMV containing a MUC1 encoding nucleotide sequence (pCMV-MUC1) or pCMV containing a c-Src encoding nucleotide sequence (pCMV-c-Src) (provided by Dr. R. Rickles, ARIAD Pharmaceuticals, Inc., Cambridge, Mass.) using electroporation methods. Efficiency of transient transfections ranged from 40-50% for ZR-75-1 cells and 70-80% for 293 cells. Cell lysates were prepared at 48 h after transfection.

MUC-1 non-expressing 293 cells or MDA-MB-231 cells were transfected with expression vectors containing either no expressible insert (pCMV), a cDNA sequence encoding MUC1 (pCMV-MUC1), a cDNA sequence encoding MUC1 with its CD deleted pCMV-MUC1/dCD) or a cDNA sequence encoding p120 (pCMV-p120). The cells were harvested 48 h after transfection and lysates were prepared from them.

Full-length wild-type MUC1 containing 40 tandem repeats was excised from pCMV-MUC1 [Li et al. (2001) J. Biol. Chem. 276:6061-6064] by Nde1 and EcoRI digestion and integrated into the Nde1/EcoRI site of the mammalian expression vector pIRESpuro2 (Clontech, Palo Alto, Calif.). The pIRESpuro2-MUC1(Y46F) mutant vector was constructed by insertion of 3'-terminal region from pCMV-MUC1(Y46F) [Li et al. (2001) J. Biol. Chem. 276:6061-6064] into pIRESpuro2-MUC1 deleted at the 3'-terminal region of MUC1 by Bsu36I. Thus, the insert in pIRESpuro2-MUC1(Y46F) encoded full-length MUC1 with the tyrosine residue at position 46 of the MUC-1 CD mutated to phenylalanine.

An expression vector (pIRESpuro2-MUC1-(T41A)) containing a cDNA sequence encoding MUC1 with threonine at position 41 of the CD mutated to an alanine residue was produced. Expression vectors were also generated by cloning into the pEGFP-C1 plasmid cDNA sequences encoding (a) wild-type PKCδ (pEGFP-PKCδ) or (b) PKCδ with the lysine residue at position 378 mutated to an arginine residue (pEFP-PKCδ(K378R).

293 cells or HCT116 cells were transiently or stably transfected with pcDNA3.1/EGF-R (containing a cDNA insert encoding EGF-R) pIRESpuro2-MUC1, pIRESpuro2-MUC1 (Y46F), pIRESpuro2-MUC1(T41A), pEGFP-PKCδ and/or pEGFP-PKCδ(K378R) by lipofectamine (Life Technologies Inc., Rockville, Md.). Cell lysates were prepared 48 h after transfection. Transfection efficiency ranged from 70-80% for 293 cells and 60-70% for HCT116 cells.

Stable transfectants were selected in the presence of 0.4 mg/ml of puromycin (Calbiochem-Novabiochem Co, San Diego, Calif.).

Immunofluorescence microscopy. ZR-75-1 cells were fixed with 4% paraformaldehyde for 10 min at room temperature (RT) and blocked with phosphate buffered saline (PBS) containing 5% fatty acid free BSA (Sigma, St. Louis, Mo.) and 5% normal goat serum (Jackson Immunoresearch Laboratories Inc., Westgrove, Pa.) (blocking buffer) for 45 min at room temperature. After incubation with anti-MUC1 (1:400) and rabbit anti-EGF-R (1:100) in blocking buffer for 14 h at 40° C., the cells were washed with PBS and incubated with fluorescein-conjugated anti-rabbit IgG (1:100) or Texas Red-conjugated anti-mouse IgG antibody (1:200) (Jackson Immunoresearch Laboratories Inc., Westgrove, Pa.) for 45 min at room temperature. The cells were then mounted onto glass cover slips using the slow-fade mounting kit (Molecular Probes, Eugene, Oreg.) and analyzed by confocal microscopy (inverted Zeiss LSM 510). Images were captured at 0.6 nm increments along the Z axis under 63× magnification and converted to composite images by ImageSpace 3.10 software (Molecular Dynamics, Sunnyvale, Calif.).

Example 2

MUC1 Binds to c-Src

To determine whether MUC1 forms a complex with c-Src, anti-MUC1 immunoprecipitates from lysates of human ZR-75-1 cells were analyzed by immunoblotting with anti-c-Src. The results demonstrate that c-Src coprecipitates with MUC1 (FIG. 1A, left panel). In the reciprocal experiment, analysis of anti-c-Src immunoprecipitates by immunoblotting with anti-MUC1 confirmed the association of MUC1 and c-Src (FIG. 1A, right panel). To assess whether the binding is direct, purified hexahistidine tagged MUC1 cytoplasmic domain (His-MUC1/CD) was incubated with a GST fusion protein that contains the c-Src SH3 domain. Analysis of the adsorbate to glutathione beads by immunoblotting with anti-MUC1/CD demonstrated binding of MUC1/CD to GST-Src SH3, and not GST or a GST-Src SH2 fusion protein (FIG. 1B). As an additional control, His-MUC1/CD was incubated with a GST fusion protein containing a mutated c-Src SH3 domain (GST-Src SH3De90/92). The finding that MUC1/CD binds to wild-type c-Src SH3, but not the mutant, supported a direct interaction between MUC1 and c-Src (FIG. 1C).

Example 3 c-Src Phosphorylates the Cytoplasmic Domain of MUC1

To determine whether MUC1/CD is a substrate for c-Src, MUC1/CD was incubated with purified c-Src and $[\gamma-^{32}P]$ ATP. Analysis of the reaction products by SDS-PAGE and autoradiography demonstrated c-Src-mediated phosphorylation of MUC1/CD (FIG. 2A). Previous studies have demonstrated that GSK3β phosphorylates MUC1/CD on Ser at a DRSPYEKV site (SEQ ID NO:12) [Li et al. (1998) Mol. Cell. Biol. 18: 7216-7224]. As the YEKV (SEQ ID NO:11) sequence represents a consensus for c-Src phosphorylation, MUC1/CD was generated with a FEKV (SEQ ID NO:14) mutation (i.e., a Y to F mutation at the first amino acid of the YEKV sequence) mutation (FIG. 2B). Incubation of MUC1/CD(Y46F) with c-Src demonstrated a decrease in phosphorylation as compared to that found with wild-type MUC1/CD (FIG. 2C). These findings indicate that c-Src phosphorylates the YEKV site as well as other sites in MUC1/CD. As the c-Src SH2 domain interacts with a preferred pYEEI sequence [Songyang et al. (1993) Cell 72: 767-778], c-Src-mediated phosphorylation of YEKV in MUC1/CD provides a potential site for c-Src SH2 binding. To determine whether the c-Src SH2 domain binds to phosphorylated MUC1/CD, MUC1/CD was incubated with c-Src and ATP and then assessed binding to GST-Src SH2. The results demonstrate that GST-Src SH2 associates with phosphorylated, but not unphosphorylated, MUC1/CD (FIG. 2D). Moreover, compared to MUC1/CD, there was substantially less binding of GST-Src SH2 to the MUC1/CD(Y46F) mutant that had been incubated with c-Src and ATP (FIG. 2D). These results support c-Src-mediated phosphorylation of MUC1/CD and thereby a direct interaction of phosphorylated MUC1/CD with the c-Src SH2 domain.

Example 4

Interaction of c-Src with MUC1 Inhibits Binding of GSK3β to MUC1

Figure 3B:
FIG. 3B is a pair of photographs of immunoblots. ZR-75-1 breast cancer cells were transiently transfected with a control expression vector ("ZR-75-1/Vector") or an expression vector containing cDNA encoding c-Src ("ZR-75-1/c-Src"). Lysates from these cells were immunoprecipitated ("IP") with anti-MUC1 ("IP: anti-MUC1"). Lysate from the cells transfected with the vector expressing c-Src was also immunoprecipitated with normal mouse IgG ("IgG"). These immunoprecipitates as well as unprecipitated lysate ("Lysate") from the cells transfected with the c-Src-expressing vector were subjected to immunoblot analysis with anti-c-Src ("IB: anti-c-Src") (top panel) or anti-GSK3β ("IB: anti-GSK3β") (bottom panel). The positions of IgG, c-Src, and GSK3β on the immunoblots are indicated.

As the c-Src phosphorylation site on MUC1/CD resides next to the binding and phosphorylation site for GSK3β [Li et al. (1998) Mol. Cell. Biol. 18: 7216-7224] an experiment was performed to test whether the interaction of MUC1/CD with c-Src affects that with GSK3β. GST-MUC1/CD was incubated with c-Src and ATP before addition of GSK3β. Analysis of proteins precipitated with glutathione-beads demonstrated that c-Src-mediated phosphorylation of MUC1/CD is associated with a decrease in binding of MUC1/CD and GSK3β (FIG. 3A). To assess the effects of c-Src on the interaction of MUC1/CD and GSK3β in vivo, ZR-75-1 cells were transfected to express the empty vector or c-Src. Anti-MUC1 immunoprecipitates were analyzed by immunoblotting with anti-GSK3β. The results demonstrate that c-Src decreases the interaction of MUC1 and GSK3β in vivo (FIG. 3B). These findings indicate that GSK3β interacts with MUC1/CD by a c-Src-dependent mechanism.

Example 5

Phosphorylation of MUC1 Cytoplasmic Domain by c-Src Increases Binding of β-catenin to MUC1

Phosphorylation of MUC1 by GSK3β decreases binding of MUC1 to β-catenin in vitro and in cells [Li et al. (1998) Mol. Cell. Biol. 18: 7216-7224]. To determine if c-Src-mediated phosphorylation of MUC1 affects the interaction of MUC1 with β-catenin, MUC1/CD was incubated with c-Src and ATP. Phosphorylated and unphosphorylated MUC1/CD were then incubated with GST or GST-β-catenin. Similar studies were performed with the MUC1/CD(Y46F) mutant. Analysis of proteins bound to glutathione beads by immunoblotting with anti-MUC1/CD demonstrated that c-Src-mediated phosphorylation of MUC1/CD increases binding of MUC1/CD to GST-β-catenin (FIG. 4A). By contrast, there was no detectable binding of phosphorylated or unphosphorylated MUC1/CD to GST (FIG. 4A). Studies performed with MUC1/CD(Y46F) demonstrated that c-Src-dependent phosphorylation of the YEKV site on MUC1/CD is necessary for the formation of MUC1/CD-β-catenin complexes (FIG. 4A). To assess whether c-Src affects the interaction of MUC1 and β-catenin in vivo, MUC1-positive ZR-75-1 cells were transfected with pCMV or pCMV-c-Src. Anti-MUC1 immunoprecipitates prepared from the transfected cells were subjected to immunoblot analysis with anti-c-Src, anti-P-Tyr (antibody specific for phosphotyrosine residues) and anti-β-catenin. The results demonstrate that c-Src associates with MUC1 in cells and induces tyrosine phosphorylation of MUC1 (FIG. 4B). In addition, c-Src expression induced the interaction of MUC1 and β-catenin (FIG. 4B). To extend these findings, MUC1-negative 293 cells [Li et al. (1998) Mol. Cell. Biol. 18: 7216-7224] were transfected to express MUC1 or MUC1 (Y46F) in which the CD YEKV site (SEQ ID NO:11) has been mutated to FEKV (SEQ ID NO:14). While there was no apparent binding of MUC1 to endogenous c-Src, cotransfection of MUC1 and c-Src was associated with detectable MUC1-c-Src complexes. Cotransfection of MUC1 and c-Src was also associated with increased tyrosine phosphorylation of MUC1 and binding of MUC1 and c-Src (FIG. 4C). By contrast, cotransfection of MUC1(Y46F) and c-Src resulted in little binding of c-Src to MUC1(Y46F) (FIG. 4C). Moreover, there was little if any tyrosine phosphorylation of MUC1(Y46F) (FIG. 4C). Importantly, cotransfection of MUC1, but not MUC1(Y46F), with c-Src induced the binding of MUC1 and β-catenin (FIG. 4C). These findings demonstrate that c-Src-mediated phosphorylation of the MUC1 YEKV site increases the interaction of MUC1 and β-catenin in cells.

Example 6 p120 Binds to the Cytoplasmic Domain of MUC1

To determine whether MUC1 associates with p120, anti-MUC1 immunoprecipitates from ZR-75-1 cells were subjected to immunoblot analysis with anti-p120. The results demonstrate that p120 coprecipitates with MUC1 (FIG. 5A). By contrast, there was no detectable p120 in the control immunoprecipitates prepared with mouse IgG (FIG. 5A). In the reciprocal experiment, analysis of anti-p120 immunoprecipitates by immunoblotting with anti-MUC1 confirmed the association of MUC1 and p120 (FIG. 5B). These findings supported an interaction of the MUC1 transmembrane protein and p120.

To further define the interaction between MUC1 and p120, MUC1-negative 293 cells [Li et al. (1998). Mol. Cell. Biol., 18, 7216-7224.] were transfected with vectors expressing MUC1 or MUC1 with its cytoplasmic domain deleted (MUC1/dCD) (FIG. 6A). Immunoblot analysis of anti-MUC1 immunoprecipitates with anti-p120 demonstrated coprecipitation of MUC1 and p120 (FIG. 6B). By contrast, there was no detectable association of p120 and MUC1/dCD (FIG. 6B). These findings indicated that p120 interacts with the MUC1/CD. To determine whether the association is direct, purified MUC1/CD was incubated with GST or a GST-p120 fusion protein. The adsorbates were analyzed by immunoblotting with anti-MUC1. The demonstration that MUC1/CD binds to GST-p120 and not to GST supported a direct interaction (FIG. 6C).

To identify the site in MUC1/CD that binds to p120, full-length MUC1/CD and the N- and C-terminal fragments (FIG. 7A) were incubated with purified GST-p120. Precipitation with glutathione beads and analysis of the precipitates by immunoblotting with anti-MUC1/CD demonstrated binding of p120 to full-length MUC1/CD and both fragments (FIG. 7B). These results suggested that p120 binds to a site in the region common to the N- and C-terminal fragments. To further localize the site, two peptides from the overlapping region were prepared. Incubation of the peptides with MUC1/CD and GST-p120 demonstrated that MSEYPTYHTH (SEQ ID NO:7), but not GRYVPPSSTDR (SEQ ID NO:8), inhibits the formation of MUC1-p120 complexes (FIG. 7C). These findings indicate that p120 interacts with the MSEYPTYHTH site (SEQ ID NO:7) in MUC1.

Example 7

MUC1 Expression Results in Increased Levels of Nuclear p120

To assess the functional significance of the MUC1-p120 interaction, MUC1-negative 293 cells were transfected to express MUC1 and then assayed for distribution of p120 in the cytoplasm and nucleus. The results demonstrate that expression of MUC1 has little if any effect on p120 levels in the cytoplasmic fraction (FIG. 8). By contrast, MUC1 expression was associated with increased levels of p120 in the nucleus (FIG. 8A). Compared to actin (as a control), nuclear p120 was increased nearly 5-fold by expression of MUC1 in 293 cells. To extend these findings, MUC1-negative MDA-MB-231 breast cancer cells were transfected to express MUC1. Immunoblot analysis demonstrated that MUC1 has no apparent effect on expression of p120 in the cytoplasm, but increases nuclear p120 levels by over 3-fold (FIG. 8B). Similar results were obtained in three separate experiments. These findings demonstrate that MUC1 regulates the nuclear expression of p120.

Example 8

MUC1 Associates with EGF-R

Figure 9A:
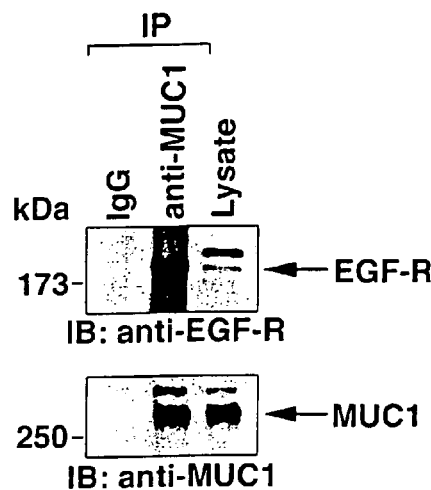
FIG. 9A is a pair of photographs of immunoblots. ZR-75-1 breast cancer cells were lysed and the lysate was immunoprecipitated ("IP") with normal IgG ("IgG") or anti-MUC1 ("anti-MUC1"). The immunoprecipitates and aliquots of the lysate that had not been immunoprecipitated ("Lysate") were subjected to immunoblot analysis with an antibody specific for epidermal growth factor receptor (EGF-R) ("IB: anti-EGF-R") (top immunoblot) or anti-MUC1 ("IB: anti-MUC1") (bottom immunoblot). The positions of EGF-R and MUC1 on the immunoblots are indicated.
Figure 9B:
FIG. 9B is a pair of photographs of immunoblots. ZR-75-1 breast cancer cells were lysed and the lysate was immunoprecipitated ("IP") with normal IgG ("IgG") or anti-EGF-R ("anti-EGF-R"). The immunoprecipitates and aliquots of the lysate that had not been immunoprecipitated ("Lysate") were subjected to immunoblot analysis with an antibody specific for epidermal growth factor receptor (EGF-R) ("IB: anti-EGF-R") (bottom immunoblot) or anti-MUC1 ("IB: anti-MUC1") (top immunoblot). The positions of EGF-R and MUC1 on the immunoblots are indicated.
Figure 9C:
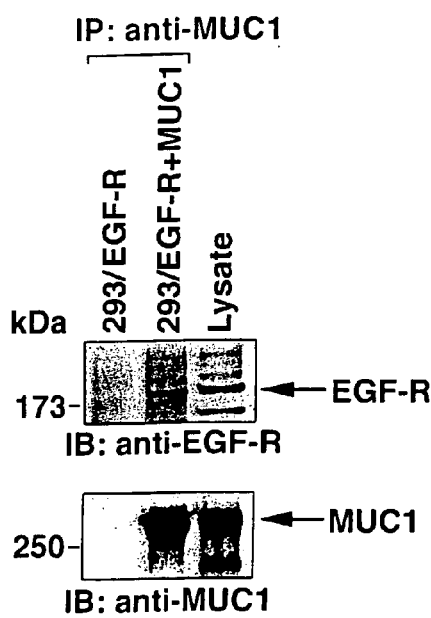
FIG. 9C is a pair of photographs of immunoblots. 293 cells were transiently transfected with either an expression vector containing a cDNA sequence encoding EGF-R ("293/EGF-R") or with an expression vector containing a cDNA sequence encoding EGF-R and an expression vector containing a cDNA sequence encoding MUC1 ("293/EGF-R+MUC1"). The transfected cells were lysed and the lysates were immunoprecipitated ("IP") with anti-MUC1 ("anti-MUC1"). The immunoprecipitates and an aliquot of the lysate of the cells transfected with vectors encoding both EGF-R and MUC1 that had not been immunoprecipitated were subjected to immunoblot analysis with anti-EGF-R ("IB: anti-EGF-R") (top immunoblot) or anti-MUC1 ("IB: anti-MUC1") (bottom immunoblot). The positions of EGF-R and MUC-1 on the immunoblots are indicated.
Figure 9D:
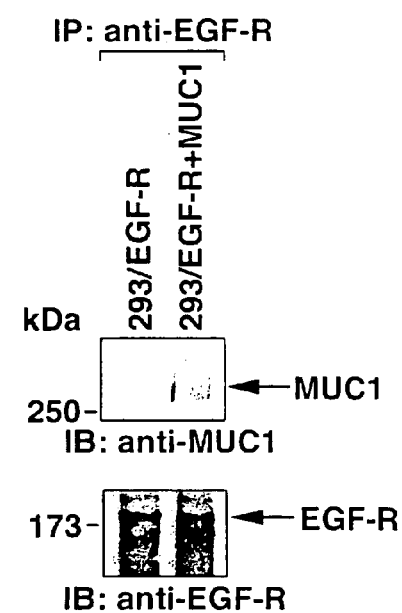
FIG. 9D is a pair of photographs of immunoblots. 293 cells were transiently transfected with: an expression vector containing a cDNA sequence encoding EGF-R ("293/EGF-R"); or with an expression vector containing a cDNA sequence encoding EGF-R and an expression vector containing a cDNA sequence encoding MUC1 ("293/EGF-R+MUC1"). The transfected cells were lysed and the lysates were immunoprecipitated ("IP") with anti-EGF-R ("anti-EGF-R"). The immunoprecipitates were subjected to immunoblot analysis with anti-EGF-R ("IB: anti-EGF-R") (bottom immunoblot) or anti-MUC1 ("IB: anti-MUC1") (top immunoblot). The positions of EGF-R and MUC-1 on the immunoblots are indicated.

To determine whether MUC1 forms a complex with EGF-R, anti-MUC1 immunoprecipitates from lysates of human ZR-75-1 cells were analyzed by immunoblotting with anti-EGF-R. The results demonstrate that EGF-R coprecipitates with MUC1 (FIG. 9A). There was no detectable EGF-R in immunoprecipitates prepared with control IgG (FIG. 9A). In the reciprocal experiment, analysis of anti-EGF-R immunoprecipitates with anti-MUC1 confirmed that EGF-R associates with MUC1 (FIG. 9B). To extend these findings, 293 cells, which express low levels of EGF-R and do not express MUC1 [Li et al. (1998) Mol. Cell. Biol. 18:7216-7224] were transfected to express EGF-R and MUC1. Immunoblot analysis with anti-EGF-R of anti-MUC1 immunoprecipitates demonstrated coprecipitation of EGF-R with MUC1 (FIG. 9C). Similar results were obtained when anti-EGF-R immunoprecipitates were analyzed by immunoblotting with anti-MUC1 (FIG. 9D). These findings demonstrate that MUC1 constitutively associates with EGF-R.

Example 9

Colocalization of EGF-R and MUC1 to the Cell Membrane

To assess the subcellular localization of MUC1 and EGF-R, confocal microscopy was performed with ZR-75-1 cells stained with rabbit anti-EGF-R and mouse anti-MUC1 antibodies. In control ZR-75-1 cells, EGF-R was distributed uniformly over the cell membrane (FIG. 10A, left). Similar findings were obtained for the distribution of MUC1 (FIG. 10A, middle). Overlay of the EGF-R (red) and MUC1 (green) signals supported colocalization (red+green–>yellow) (FIG. 10A, right). Following EGF stimulation, the EGF-R was found to be clustered in patches at the cell membrane (FIG. 10B, left). An identical pattern was observed for MUC1 (FIG. 10B, middle). Moreover, overlay of the signals showed that EGF-R and MUC1 colocalize in clusters at the cell membrane (FIG. 10B, right). Analysis of the control and EGF-stimulated cells by coimmunoprecipitation studies demonstrated no detectable difference in the association between EGF-R and MUC1 (data not shown). These findings and those obtained in coprecipitation studies demonstrate that MUC1 and EGF-R associate constitutively at the cell membrane.

Example 10

EGF-R Phosphorylates MUC1 in vitro and in vivo

Figure 11A:
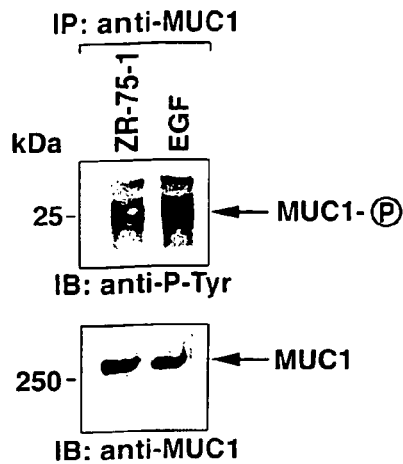
FIG. 11A is a pair of photographs of immunoblots. ZR-75-1 breast cancer cells that had been cultured in the absence ("ZR-75-1") or presence ("EGF"; 10 ng/ml) of EGF for 5 min were lysed and the lysates were immunoprecipitated ("IP") with anti-MUC1 ("anti-MUC1"). The immunoprecipitates were subjected to immunoblot analysis with anti-P-Tyr ("IB: anti-P-Tyr") (top immunoblot) or anti-MUC1 ("IB: anti-MUC1") (bottom immunoblot). The positions of phosphorylated (P in a circle) MUC1 and MUC1 on the immunoblots are indicated.
Figure 11B:
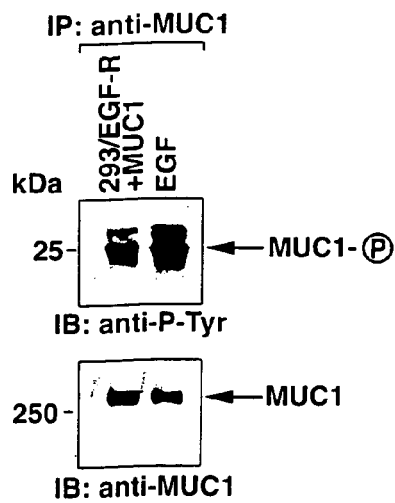
FIG. 11B is a pair of photographs of immunoblots. 293 cells were transiently transfected with an expression vector containing a cDNA sequence encoding EGF-R and an expression vector containing a cDNA sequence encoding MUC1 ("293/EGF-R+MUC1"). The transfected cells were cultured in the absence ("ZR-75-1") or presence ("EGF"; 10 ng/ml) of EGF for 5 min. and then lysed. The lysates were immunoprecipitated ("IP") with anti-MUC1 ("anti-MUC1"). The immunoprecipitates were subjected to immunoblot analysis with anti-P-Tyr ("IB: anti-P-Tyr") (top immunoblot) or anti-MUC1 ("IB: anti-MUC1") (bottom immunoblot). The positions of phosphorylated MUC1 and MUC-1 on the immunoblots are indicated.
Figure 11C:
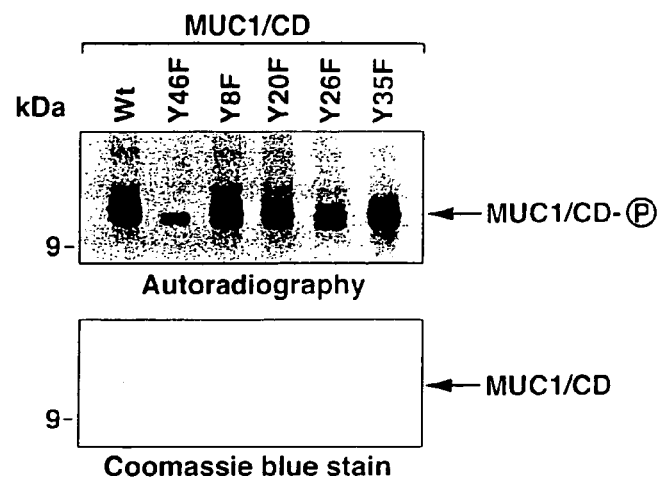
FIG. 11C is a photograph of an autoradiogram (top panel) and a Coomassie blue-stained SDS-PAGE gel (bottom panel). Purified recombinant wild-type ("Wt") and mutant MUC1/CD proteins (see below) were incubated with purified recombinant EGF-R and [γ−$^{32}$P] ATP. The reaction products were analyzed by SDS-PAGE and autoradiography (top panel). The gel used for autoradiography was also stained with Coomassie blue in order to assess the relative levels of protein loading onto the gel (bottom panel). The mutant MUC1/CD proteins had tyrosine residues at positions 46 ("Y46F"), 8 ("Y8F"), 20 ("Y20F"), 26 ("Y26F"), and 35 ("Y35F") of MUC1/CD (SEQ ID NO:1) mutated to phenylalanine.
Figure 11D:
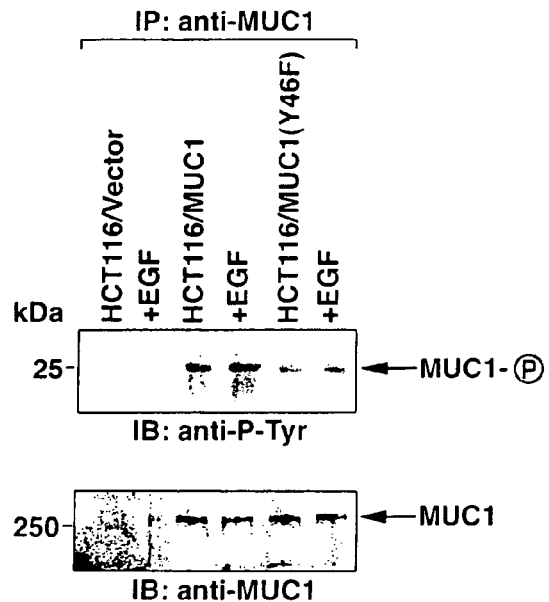
FIG. 11D is a pair of photographs of immunoblots. HCT116 cells were transiently transfected with: a control expression vector ("HCT116/Vector"; first two lanes of immunoblots); an expression vector containing a cDNA sequence encoding MUC1 ("HCT116/MUC1"; middle two lanes of immunoblots); or an expression vector containing a cDNA sequence encoding MUC1 with the tyrosine residue at position 46 of MUC1/CD mutated to phenylalanine ("HCT116/MUC1 (Y46F)"; last two lanes of immunoblots). The transfected cells were cultured in the absence (lanes indicated by the acronym for the relevant transfected cells) or presence (lanes indicated by "+EGF") of EGF (10 ng/ml) for 5 min. and then lysed. The lysates were immunoprecipitated ("IP") with anti-MUC1 ("anti-MUC1"). The immunoprecipitates were subjected to immunoblot analysis with anti-P-Tyr ("IB: anti-P-Tyr") (top immunoblot) or anti-MUC1 ("IB: anti-MUC1") (bottom immunoblot). The positions of phosphorylated (P in a circle) MUC1 and MUC-1 on the immunoblots are indicated.

To determine whether EGF-R phosphorylates MUC1, anti-MUC1 immunoprecipitates from control and EGF-stimulated ZR-75-1 cells were analyzed by immunoblotting with anti-P-Tyr. The results demonstrate a detectable level of tyrosine phosphorylated MUC1 in control cells (FIG. 11A). Moreover, EGF stimulation was associated with an increase in phosphorylation of MUC1 on tyrosine (FIG. 11A). EGF-induced tyrosine phosphorylation of MUC1 was also observed in 293 cells transfected to express EGF-R and MUC1 (FIG. 11B). The 72 amino acid MUC1 cytoplasmic domain (MUC1/CD) contains 7 tyrosines (see schema in FIG. 12D). To define potential sites of EGF-R phosphorylation, a MUC1 cytoplasmic domain fragment (MUC1/CD) was incubated with EGF-R and $[\gamma-^{32}P]ATP$. Analysis of the reaction products demonstrated that EGF-R phosphorylates MUC1/CD (FIG. 11C). Mutation of the Y8 site of MUC1/CD to F had no detectable effect on EGF-R-mediated phosphorylation of MUC1/CD (FIG. 11C). There was also no apparent effect on phosphorylation when the Y20, or Y35 sites, were mutated to F (FIG. 11C). By contrast, incubation of MUC1/CD(Y46F) with EGF-R was associated with a marked decrease in phosphorylation as compared to that found with wild-type MUC1/CD (FIG. 11C). Mutation of Y26 also resulted in decreased phosphorylation, but to a lesser extent than that obtained with Y46F (FIG. 11C). To determine whether the Y46 site is phosphorylated in cells, human HCT116 cells, which express EGF-R and not MUC1, were stably transfected to express the empty vector, wild-type MUC1 or the MUC1(Y46F) mutant. Analysis of anti-MUC1 immunoprecipitates with anti-P-Tyr demonstrated that EGF-mediated phosphorylation of MUC1 (Y46F) is decreased compared that obtained with wild-type MUC1 (FIG. 11D). These findings demonstrate that EGF-R phosphorylates MUC1 on Y46 in vitro and in cells.

Example 11

EGF-R Regulates Interaction of MUC1 with c-Src and β-catenin

To determine whether EGF-R-mediated phosphorylation regulates the interaction of MUC1 with c-Src and β-catenin, MUC1/CD was incubated with EGF-R and ATP and then binding to GST-Src SH2 and GST-β-catenin was assessed. Immunoblot analysis of adsorbates to glutathione beads with anti-MUC1/CD showed that GST-Src SH2 binds to MUC1/CD EGF-R after phosphorylation (FIG. 12A). In addition, compared to MUC1/CD, there was substantially less binding of GST-Src SH2 to the MUC1/CD(Y46F) mutant that had been incubated with EGF-R and ATP (FIG. 12A). Similar findings were obtained for binding of GST-β-catenin (FIG. 12A). To assess whether EGF-R-mediated phosphorylation of MUC1 induces binding of MUC1 to c-Src and β-catenin in cells, anti-MUC1 immunoprecipitates from ZR-75-1 cells were analyzed by immunoblotting with anti-c-Src or anti-β-catenin. Analysis of lysates from control ZR-75-1 cells demonstrated a low but detectable interaction of MUC1 with c-Src and β-catenin (FIG. 12B). In concert with the in vitro results, stimulation of ZR-75-1 cells with EGF induced the interaction of MUC1 with c-Src and β-catenin (FIG. 12B). To confirm involvement of the MUC1 Y46 site, HCT116 cells stably expressing wild-type MUC1 or MUC1(Y46F) were stimulated with EGF. Immunoblot analysis of anti-MUC1 immunoprecipitates with anti-c-Src demonstrated that, compared to wild-type MUC1, there was less EGF-induced binding of MUC1(Y46F) to c-Src (FIG. 12C). Similar findings were obtained for β-catenin (FIG. 12C). These results show that EGF-R-mediated phosphorylation of MUC1 Y46 induces the interaction of MUC1 with c-Src and β-catenin.

Example 12

MUC1 Binds Directly to PKCδ

Figure 13A:
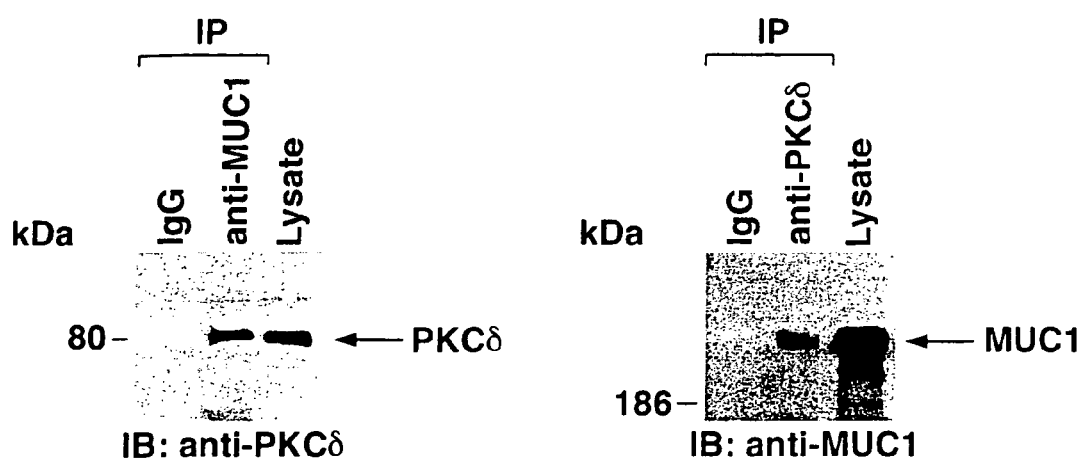
FIG. 13A is a pair of photographs of immunoblots. A lysate of ZR-75-1 breast cancer cells was immunoprecipitated with control mouse IgG (left lane in both panels), anti-MUC1 ("anti-MUC1"; middle lane, left panel), or antibody specific for PKCδ ("anti-PKCδ"; middle lane, right panel). The immunoprecipitates were subjected to immunoblot analysis with anti-PKCδ (left panel) ("IB: anti-PKCδ") or anti-MUC1 (right panel) ("IB: anti-MUC1"). An aliquot of the lysate not subjected to immunoprecipitation was also analyzed by immunoblot analysis ("Lysate"; right lane of both panels). The positions of PKCδ and MUC1 on the immunoblots are indicated.
Figure 13C:
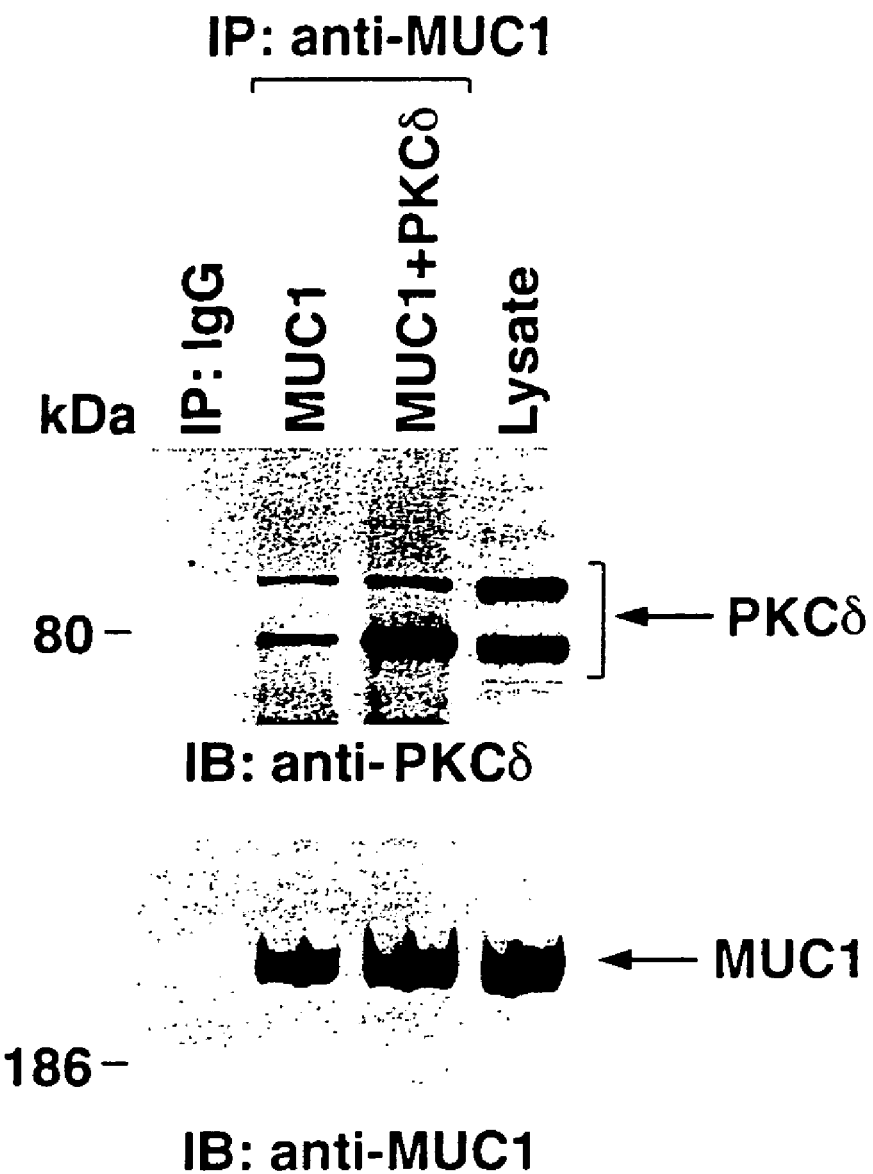
FIG. 13C is a pair of photographs of immunoblots. 293 cells were transiently transfected with: an expression vector containing a cDNA sequence encoding MUC1 ("MUC1"); or with an expression vector containing a cDNA sequence encoding MUC1 and an expression vector containing a cDNA sequence encoding PKCδ ("MUC1+PKCδ"). The transfected cells were lysed and the lysates were immunoprecipitated ("IP") with mouse IgG ("IP: IgG") (first lane of both panels) or anti-MUC1 ("IP: anti-MUC1") (second and third lanes of both panels). The immunoprecipitates were subjected to immunoblot analysis with anti-PKCδ ("IB: anti-PKCδ") (top panel) or anti-MUC1 ("IB: anti-MUC1") (bottom panel). An aliquot of the lysate not subjected to immunoprecipitation was also analyzed by immunoblot analysis ("Lysate"; fourth lane of both panels). The positions of PKCδ and MUC-1 on the immunoblots are indicated.

To determine whether MUC1 associates with PKCδ, lysates from human ZR-75-1 cells were subjected to immunoimmunoprecipitation with anti-MUC1 and, as a control, normal IgG. Immunoblot analysis of the immunoprecipitates with anti-PKCδ demonstrated the presence of MUC1-PKCδ complexes (FIG. 13A, left). In the reciprocal experiment, immunoblot analysis of anti-PKCδ immunoprecipitates with anti-MUC1 confirmed that MUC1 associates with PKCδ (FIG. 13A, right). By contrast, there was no detectable interaction between MUC1 and three other protein kinase C molecules, i.e., PKCβ$_{II}$, PKCη and PKCμ (FIG. 13B). To extend these findings, 293 cells, which do not express for MUC1, were transfected to express MUC1 or MUC1 and PKCδ. Immunoblot analysis of anti-MUC1 immunoprecipitates with anti-PKCδ demonstrated binding of MUC1 with endogenous PKCδ (FIG. 13C). Moreover, coexpression of MUC1 and PKCδ resulted in increased formation of MUC1-PKCδ complexes (FIG. 13C). To assess whether binding is direct, GST or a GST fusion protein containing the MUC1 CD (GST-MUC1/CD) was incubated with recombinant PKCδ. Adsorbates to glutathione beads were subjected to immunoblot analysis with anti-PKCδ. The finding that PKCδ binds to GST-MUC1/CD and not to GST alone supported a direct interaction (FIG. 13D).

Example 13

PKCδ Phosphorylates Threonine at Position 41 of the CD of MUC1

Figure 14B:
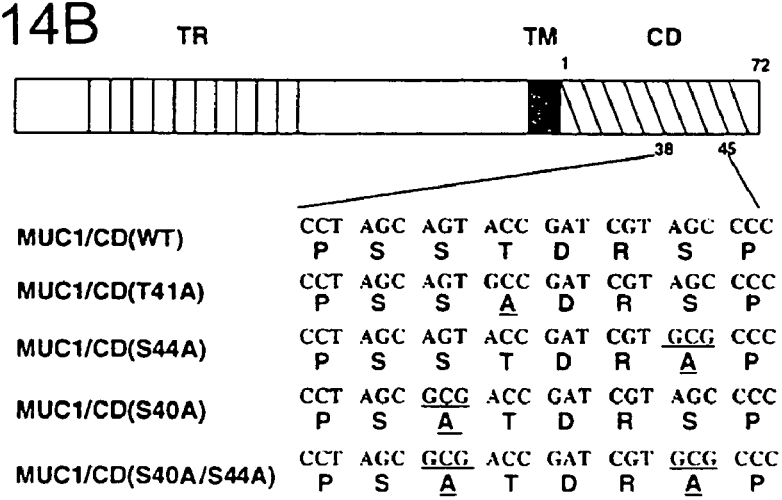
FIG. 14B is a schematic representation of the structure of wild-type MUC1 and a depiction of the sequences of amino acids 38-45 of MUC1/CD as they occur in: wild-type MUC1 ("MUC1/CD (WT)") (SEQ ID NO:16); MUC1 in which the threonine residue at position 41 of MUC1/CD is mutated to alanine ("MUC1/CD(T41A)") (SEQ ID NO:17); MUC1 in which the serine residue at position 44 of MUC1/CD is mutated to alanine ("MUC1/CD(S44A)") (SEQ ID NO:18); MUC1 in which the serine residue at position 40 of MUC1/CD is mutated to alanine ("MUC1/CD(S40A)") (SEQ ID NO:19); and MUC1 in which the serine residue at position 40 and the serine residue at position 44 of MUC1/CD are mutated to alanine ("MUC1/CD (S40A/S44A)") (SEQ ID NO:20). Also indicated above each of these amino acid sequences are the nucleotide sequences encoding the amino acid sequences (SEQ ID NOS:21-25). The numbers indicate amino acid positions in MUC1/CD (SEQ ID NO:1). TR, tandem repeat domain; TM, transmembrane domain; CD, cytoplasmic domain.
Figure 14C:
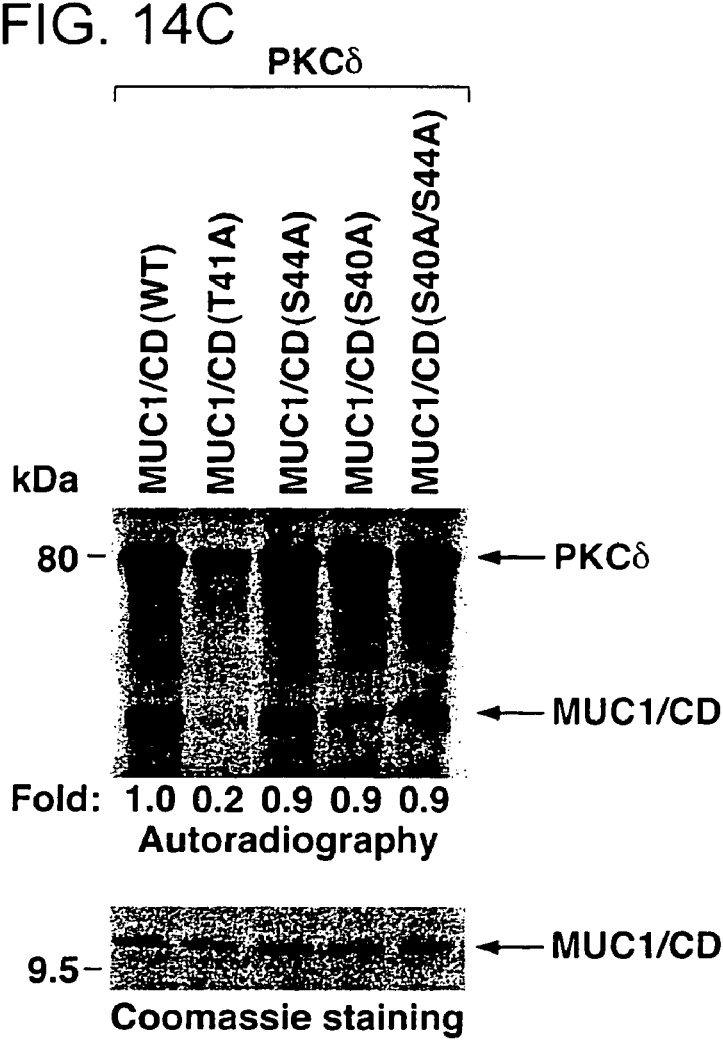
FIG. 14C is a photograph of an autoradiogram (top panel) and a Coomassie blue-stained SDS-PAGE gel (bottom panel). Purified recombinant PKCδ was incubated with wild-type MUC1/CD or one of four mutant MUC1/CD proteins (containing the mutations indicated in FIG. 14B) and [γ–$^{32}$P] ATP. The reaction products were analyzed by SDS-PAGE and autoradiography (top panel). The gel used for autoradiography was also stained with Coomassie blue in order to assess relative levels of protein loading onto the gel. The positions of PKCδ and MUC1/CD on the autoradiogram and the Coomassie blue-stained SDS-PAGE gel are indicated.
Figure 14D:
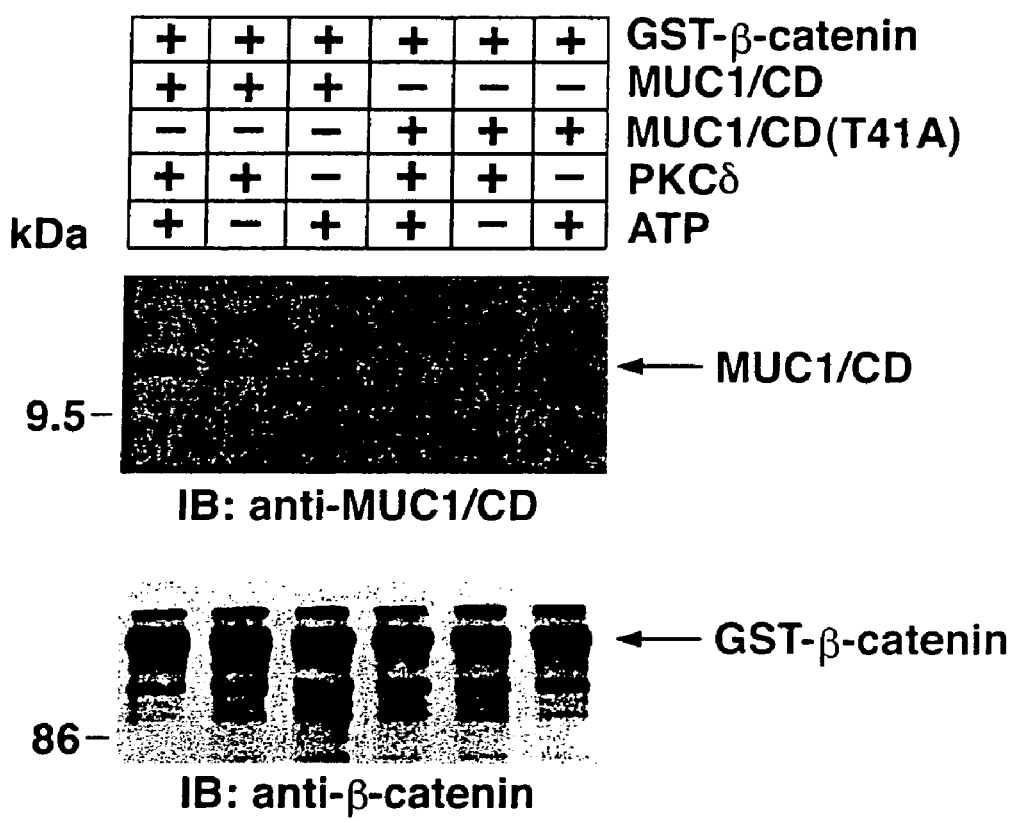
FIG. 14D is a pair photographs of immunoblots. The table above the top immunoblot indicates the presence ("+") or absence ("−") of various components [PKCδ, ATP, wild type MUC1/CD ("MUC1/CD+PKCδ"), and mutant MUC1/CD (T41A) ("MUC1/CD(T41A)+PKCδ")] of a series of six phosphorylation reaction mixtures. As indicated in the table, GST-β-catenin was added to all the reaction mixtures after completion of the phosphorylation reaction. The reaction mixtures were then incubated with glutathione-Sepharose 4B™ beads and proteins precipitated by the beads were subjected to immunoblot analysis with anti-MUC1/CD ("IB: anti-MUC1/CD") (top panel) or anti-PKCδ ("IB: anti-PKCδ") (bottom panel).

To determine whether MUC1/CD is a substrate for PKCδ, purified His-MUC1/CD was incubated with recombinant PKCδ and [γ–$^{32}$P]ATP. Analysis of the reaction products by SDS-PAGE and autoradiography demonstrated phosphorylation of MUC1 CD (FIG. 14A). A STDRS site (SEQ ID NO:9) in MUC1/CD conforms to the preferred S/T-X-K/R motif for PKC phosphorylation. The T residue in the STDRS sequence is at position 41 in the CD of MUC1 (i.e., in SEQ ID NO:1). To determine whether STDRS is phosphorylated by PKCδ, this site in MUC1/CD was mutated to SA41DRS (SEQ. ID NO:15) (FIG. 14B). PKCδ-mediated phosphorylation of MUC1/CD(T41A) was attenuated compared to that obtained with wild-type MUC1/CD (FIG. 14B). By contrast, phosphorylation of MUC1 by PKCδ was unaffected by S to A mutations of either or both of the flanking serines (FIG. 14B). Previous studies have shown that phosphorylation of the MUC1/CD S44 site by GSK3β decreases the interaction between MUC1/CD and β-catenin. To assess the effects of PKCδ-mediated phosphorylation of MUC1/CD, MUC1/CD was incubated with PKCδ in the presence and absence of ATP. After phosphorylation of MUC1/CD, GST or GST-β-catenin was added to the reaction mixture which were further incubated for 1 h at 4° C. Proteins precipitated with glutathione beads were analyzed by immunoblotting with anti-MUC1/CD. MUC1/CD binds to GST-β-catenin and not GST. Preincubation of MUC1/CD with PKCδ and ATP was associated a higher level of MUC1/CD binding to GST-β-catenin than that obtained in the absence of PKCδ or ATP (FIG. 14D). By contrast, preincubation of MUC1/CD(T41A) with PKCδ and ATP had no detectable effect on binding of MUC1/CD (T41A) to β-catenin (FIG. 14D). These findings demonstrate that PKCδ phosphorylates MUC1/CD on T41 and thereby increases binding of MUC1/CD and β-catenin.

Example 14

PKCδ Regulates the Interaction of MUC1 with β-catenin in Cells

Figure 15A:
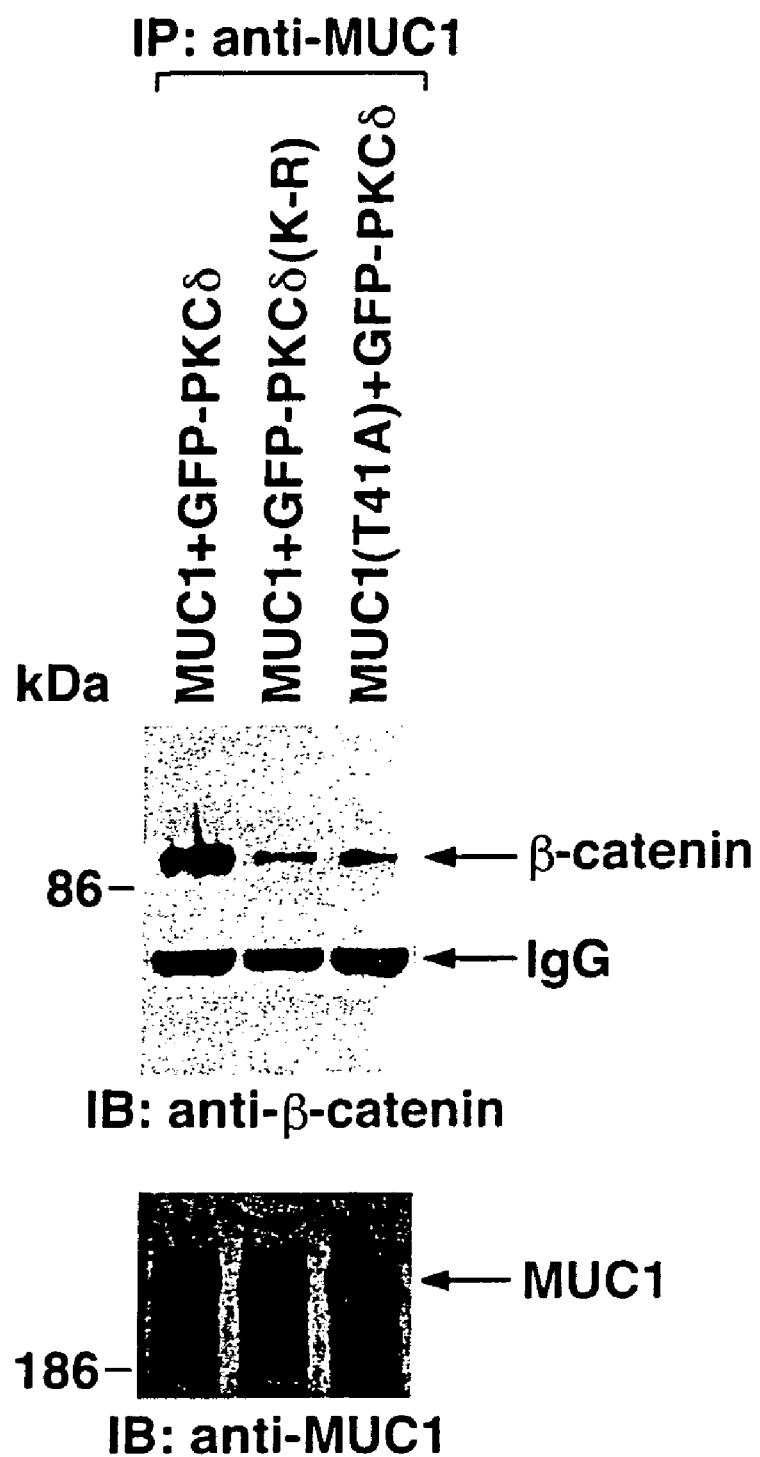
FIG. 15A is a pair of photographs of immunoblots. 293 cells were transiently transfected with: an expression containing cDNA encoding MUC1 and an expression vector encoding green fluorescent protein (GFP) fused to PKCδ ("MUC1+ GFP-PKCδ"); an expression vector containing cDNA encoding MUC1 and an expression vector encoding GFP fused to the kinase-inactive PKCδ mutant PKCδ(K378R) ("MUC1+GFP-PKCδ(K-R)"); or an expression vector containing cDNA encoding MUC1 with the threonine residue at position 41 of the CD mutated to alanine and an expression vector encoding GFP fused to PKCδ ("MUC1(T41A)+GFP-PKCδ"). Lysates from these cells were immunoprecipitated with anti-MUC1 ("IP: anti-MUC1"). The immunoprecipitates were subjected to immunoblot analysis with anti-β-catenin ("IB: anti-β-catenin") (top panel) or anti-MUC1 ("IB: anti-MUC1") (bottom panel). The positions of β-catenin, IgG, and MUC1 on the immunoblots are indicated.
Figure 15B:
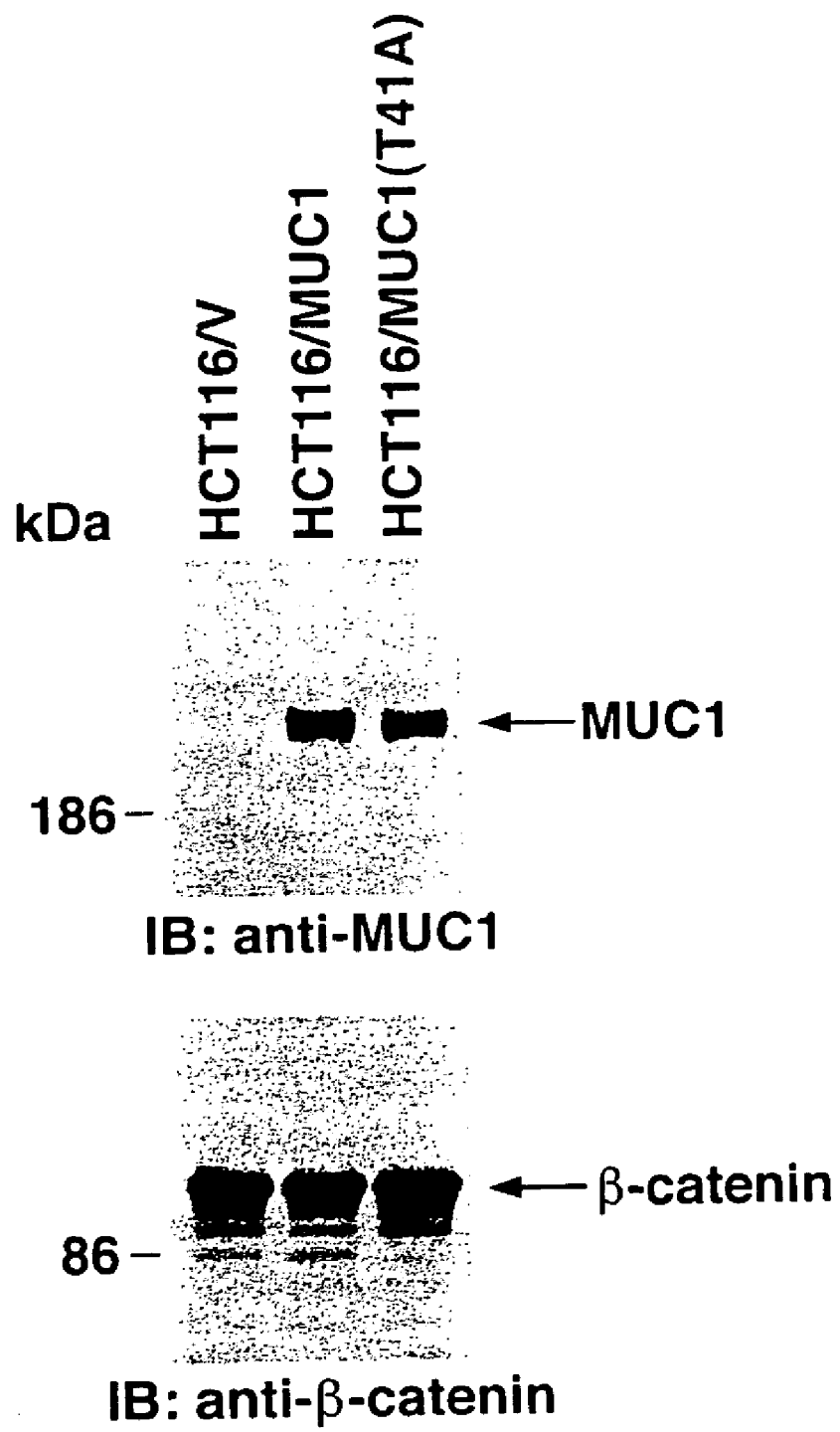
FIG. 15B is a pair of photographs of immunoblots. HCT116 cells were stably transfected with: a control expression vector ("HCT116/V"); an expression vector containing a cDNA sequence encoding MUC1 ("HCT116/MUC1"); or an expression vector containing a cDNA sequence encoding MUC1 with the threonine residue at position 41 of MUC1/CD mutated to alanine ("HCT116/MUC1 (T41A)"). Lysates prepared from the transfected cells were immunoprecipitated with anti-MUC1 and the immunoprecipitates were subjected to immunoblot analysis with anti-MUC1 ("IB: anti-MUC1") (top panel) or anti-β-catenin ("IB: anti-β-catenin"). The positions of MUC-1 and β-catenin on the immunoblots are indicated.

To determine whether PKCδ regulates the interaction between MUC1 and β-catenin in cells, transfection studies were performed in MUC1-non-expressing 293 cells. After transfection of vectors expressing MUC1 and green fluorescent protein (GFP) fused to PKCδ (GFP-PKCδ) or GFP fused to the kinase-inactive PKCδ(K378R) mutant (GFP-PKCδ(K-R)), lysates were subjected to immunoprecipitation with anti-MUC1. Immunoblot analysis of the immunoprecipitates with anti-β-catenin demonstrated that PKCδ increases the interaction between MUC1 and β-catenin; this was not seen in cells transfected with GFP-PKCδ(K378R) encoding cDNA (FIG. 15A). In concert with these results, GFP-PKCδ had little (if any) effect on binding of β-catenin to the MUC1(T41A) mutant (FIG. 15A). To extend the analysis, MUC1-non-expressing HCT116 cells were transfected to stably express a control vector, or with wild-type MUC1- or MUC1(T41A)-expressing vectors to create the HCT116V, HCT116/MUC1, and HCT116/MUC1(T41A) transfected clones, respectively (FIG. 15B). Anti-MUC1 immunoprecipitates from HCT116/V, HCT116/MUC1 and HCT116/MUC1(T41A) cells were subjected to immunoblotting with anti-β-catenin. These results demonstrate that MUC1, but not MUC1(T41A), binds to β-catenin (FIG. 15B). When these cells were transfected to express GFP-PKCδ, immunoblot analysis of anti-MUC1 immunoprecipitates with anti-β-catenin demonstrated that PKCδ induces binding of β-catenin to wild-type MUC1 and not the MUC1(T41A) mutant (FIG. 15B). Transfection with an PKCδ(K378R)-encoding expression vector had no apparent effect on induction of MUC-β-catenin complexes (data not shown). These findings demonstrate that phosphorylation of MUC1 T41 by PKCδ induces binding of MUC1 and β-catenin. To determine whether expression of the MUC1 (T41A) mutant affects binding of β-catenin to E-cadherin, anti-E-cadherin immunoprecipitates were analyzed by immunoblotting with anti-β-catenin. Expression of wild-type MUC1 was associated with decreased binding of E-cadherin and β-catenin (FIG. 15C). By contrast, expression of MUC1 (T41A) had less of an effect on the interaction of E-cadherin and β-catenin than did wild-type MUC1 (in HCT116/MUC1 cells) (FIG. 15C). Similar results were obtained after transfection of with an expression vector containing a nucleic acid sequence encoding GFP-PKCδ (FIG. 15C). These findings demonstrate that PKCδ regulates the interaction between MUC1 and β-catenin in cells and thereby binding of E-cadherin with β-catenin.

Example 15

Effects of MUC1 on Anchorage-Independent Growth are Abrogated by the T41A Mutation To assess the functional significance of the interaction between MUC1 and PKCδ, HCT116/V, HCT116/MUC1 and HCT116/MUC1(T41A) cells were plated for anchorage-independent growth in soft agar. The wild-type MUC1 transfectants formed colonies that were substantially larger than those obtained with HCT116/V cells (FIG. 16A). By contrast, expression of MUC1(T41A) was associated with the formation of colonies that were similar to those found with control HCT116/V cells (FIG. 16A). Similar results were obtained with independently selected clones of the transfected cells (FIG. 16A). The number of colonies obtained with HCT116/MUC1 cells was also higher than those found for HCT116/V and HCT116/MUC1(T41A) cells (FIG. 16B). These findings demonstrate that expression of wild-type MUC1 contributes to anchorage-independent growth and that mutation of the PKCδ phosphorylation site in the CD of MUC1 abrogates this effect.

A number of embodiments of the invention have been described. Nevertheless, it will be understood that various modifications may be made without departing from the spirit and scope of the invention. Accordingly, other embodiments are within the scope of the following claims.

What is claimed is:

1. A method of identifying a compound that inhibits binding of MUC1 to a tumor progressor, the method comprising:
   (a) providing a MUC1 test agent, wherein the MUC1 test agent comprises a phosphorylated YEKV site;
   (b) providing a tumor progressor test agent that has increased binding to the phosphorylated MUC1 test agent as compared to a MUC1 test agent that does not comprise a phosphorylated YEKV site;
   (c) contacting the phosphorylated MUC1 test agent with the tumor progressor test agent in the presence of a test compound; and
   (d) determining whether the test compound inhibits binding of the phosphorylated MUC1 test agent to the tumor progressor test agent.

2. The method of claim 1, wherein the tumor progressor test agent is a c-Src test agent.

3. The method of claim 1, wherein the tumor progressor test agent is a p120$^{ctn}$ test agent.

4. The method of claim 1, wherein the tumor progressor test agent is an epidermal growth factor receptor (EGF-R) test agent.

5. The method of claim 1, wherein the tumor progressor test agent is a β-catenin test agent.

6. The method of claim 5, wherein the MUC1 test agent comprises SEQ ID NO:1 phosphorylated at Y46.

7. The method of claim 5, wherein providing a phosphorylated MUC1 test agent comprises combining a MUC1 test agent, a tumor progressor test agent with kinase activity, and ATP, wherein a MUC1 test agent phosphorylated at a YEKV site is formed.

8. The method of claim 7, wherein the tumor progressor test agent with kinase activity is c-src, EGF-R, or PKCδ.

9. The method of claim 1, wherein the tumor progressor test agent is a protein kinase Cδ (PKCδ) test agent.

10. The method of claim 1, wherein the contacting is carried out in a cell-free system.

11. The method of claim 1, wherein the contacting occurs in a cell.

12. The method of claim 11, wherein the cell is a cancer cell.

13. The method of claim 12, wherein the cancer cell expresses MUC1.

14. The method of claim 12, wherein the cancer cell is a breast cancer cell, a lung cancer cell, a colon cancer cell, a pancreatic cancer cell, a renal cancer cell, a stomach cancer cell, a liver cancer cell, a bone cancer cell, a hematological cancer cell, a neural tissue cancer cell, a melanoma cell, an ovarian cancer cell, a testicular cancer cell, a prostate cancer cell, a cervical cancer cell, a vaginal cancer cell, or a bladder cancer cell.

15. The method of claim 1, wherein the test compound is a peptide fragment of the tumor progressor.

16. The method of claim 15, wherein the tumor progressor test agent is a c-Src test agent.

17. The method of claim 15, wherein the tumor progressor test agent is a p120$^{ctn}$ test agent.

18. The method of claim 15, wherein the tumor progressor test agent is an epidermal growth factor receptor (EGF-R) test agent.

19. The method of claim 15, wherein the tumor progressor test agent is a β-catenin test agent.

20. The method of claim 15, wherein the tumor progressor test agent is a protein kinase Cδ (PKCδ) test agent.

21. The method of claim 15, wherein the contacting is carried out in a cell-free system.

22. The method of claim 15, wherein the contacting occurs in a cell.

23. The method of claim 1, wherein the MUC1 test agent comprises SEQ ID NO:1.

* * * * *

UNITED STATES PATENT AND TRADEMARK OFFICE
CERTIFICATE OF CORRECTION

PATENT NO. : 7,745,109 B2
APPLICATION NO. : 10/733212
DATED : June 29, 2010
INVENTOR(S) : Donald W. Kufe Page 1 of 1

It is certified that error appears in the above-identified patent and that said Letters Patent is hereby corrected as shown below:

In title page, item (62) Related U.S. Application Data, insert
--Division of application No. 10/032,786, filed on Dec. 26, 2001, now abandoned.

Provisional application No. 60/257,590, filed on Dec. 22, 2000.

Provisional application No. 60/308,307, filed on Jul. 27, 2001.--.

Signed and Sealed this

Second Day of November, 2010

David J. Kappos
*Director of the United States Patent and Trademark Office*